US009617569B2

(12) United States Patent
Song et al.

(10) Patent No.: US 9,617,569 B2
(45) Date of Patent: Apr. 11, 2017

(54) GENETICALLY ENGINEERED YEAST CELL PRODUCING LACTATE INCLUDING ACETALDEHYDE DEHYDROGENASE, METHOD OF PRODUCING YEAST CELL, AND METHOD OF PRODUCING LACTATE USING THE SAME

(71) Applicant: Samsung Electronics Co., Ltd., Suwon-si, Gyeonggi-do (KR)

(72) Inventors: Jiyoon Song, Seoul (KR); Changduk Kang, Gwacheon-si (KR); Joonsong Park, Seoul (KR); Sungsoo Kim, Hwaseongi-si (KR); Youngkyoung Park, Seoul (KR); Sunghaeng Lee, Seoul (KR); Soyoung Lee, Daejeon (KR); Juyoung Lee, Daegu (KR); Kwangmyung Cho, Seongnam-si (KR); Wooyong Lee, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 19 days.

(21) Appl. No.: 14/542,275

(22) Filed: Nov. 14, 2014

(65) Prior Publication Data
US 2015/0140626 A1   May 21, 2015

(30) Foreign Application Priority Data

Nov. 15, 2013  (KR) .................. 10-2013-0139320
Sep. 1, 2014    (KR) .................. 10-2014-0115688

(51) Int. Cl.
| | | |
|---|---|---|
| *C12P 7/56* | (2006.01) | |
| *C12N 9/04* | (2006.01) | |
| *C12N 9/02* | (2006.01) | |
| *C12N 9/88* | (2006.01) | |
| *C12N 15/52* | (2006.01) | |
| *C12N 15/81* | (2006.01) | |

(52) U.S. Cl.
CPC .............. *C12P 7/56* (2013.01); *C12N 9/0006* (2013.01); *C12N 9/0008* (2013.01); *C12N 9/88* (2013.01); *C12N 15/52* (2013.01); *C12N 15/81* (2013.01); *C12Y 101/01028* (2013.01); *C12Y 101/02* (2013.01); *C12Y 102/0101* (2013.01); *C12Y 401/03039* (2013.01); *Y02P 20/52* (2015.11)

(58) Field of Classification Search
None
See application file for complete search history.

(56) References Cited

U.S. PATENT DOCUMENTS

| 8,293,940 B2 | 10/2012 | Lum et al. |
| 8,349,597 B2 | 1/2013 | Ito et al. |
| 8,415,136 B1 | 4/2013 | Gardner et al. |

FOREIGN PATENT DOCUMENTS

| JP | 63-185403 A | 8/1988 |
| JP | 06-238141 A | 8/1994 |
| KR | 10-2011-0076800 A | 7/2011 |
| KR | 10-2013-0049627 A | 5/2013 |
| WO | WO 2007/117282 A2 | 8/2007 |
| WO | WO 2007/106524 A2 | 9/2007 |
| WO | WO 2013/076144 A2 | 5/2013 |

OTHER PUBLICATIONS

Song et al. (2016) Metabolic Engineering 35, 38-45.*
Abbott et al., Metabolic engineering of *Saccharomyces cerevisiae* for production of carboxylic acids: current status and challenges, *FEMS Yeast Research*, 9: 1123-1136 (2009).
Ishida et al., The Effect of Pyruvate Decarboxylase Gene Knockout in *Saccharomyces cerevisiae* on L-Lactic Acid Production, *Bioscience Biotechnology Biochemistry*, 70(5): 1148-1153 (2006).
Okano et al., "Biotechnological production of enantiomeric pure lactic acid from renewable resources: recent achievements, perspectives, and limits", *Applied Microbiology Biotechnology*, 85: 413-423 (2010).
Ookubo et al., Improvement of L-Lactate Production by *CYB2* Gene Disruption in a Recombinant *Saccharomyces cerevisiae* Strain under Low pH Condition, *Bioscience Biotechnology Biochemistry*, 72(11): 3063-3066 (2008).
Sauer et al., "16 years research on lactic acid production with yeast—ready for the market?", *Biotechnology and Genetic Engineering Reviews*, 27: 229-256 (2010).
Tokuhiro et al., "Double mutation of the PDCI and ADHI genes improves lactate production in the yeast *Saccharomyces cerevisiae* expressing the bovine lactate dehyrogenase gene", *Applied Microbiology Biotechnology*, 82: 883-890 (2009).
European Patent Office, Extended Search Report in Application No. 14193136.0, dated Mar. 31, 2015, pp. 1-10.

* cited by examiner

*Primary Examiner* — Nashaat Nashed
(74) *Attorney, Agent, or Firm* — Leydig, Voit & Mayer, Ltd.

(57) ABSTRACT

Provided is a genetically engineered yeast cell with lactate production capacity, including an enzyme that catalyzes conversion of acetaldehyde to acetyl-CoA and an enzyme that catalyzes conversion of pyruvate to lactate, which activities are increased compared to a parent cell of the yeast cell, as well as a method of producing the genetically engineered yeast cell and method of producing lactate using the genetically engineered yeast cell.

17 Claims, 3 Drawing Sheets

SEQUENCE LISTING

```
<160> NUMBER OF SEQ ID NOS: 82

<210> SEQ ID NO 1
<211> LENGTH: 316
<212> TYPE: PRT
<213> ORGANISM: Escherichia coli

<400> SEQUENCE: 1

Met Ser Lys Arg Lys Val Ala Ile Ile Gly Ser Gly Asn Ile Gly Thr
  1               5                  10                  15

Asp Leu Met Ile Lys Ile Leu Arg His Gly Gln His Leu Glu Met Ala
             20                  25                  30

Val Met Val Gly Ile Asp Pro Gln Ser Asp Gly Leu Ala Arg Ala Arg
         35                  40                  45

Arg Met Gly Val Ala Thr Thr His Glu Gly Val Ile Gly Leu Met Asn
     50                  55                  60

Met Pro Glu Phe Ala Asp Ile Asp Ile Val Phe Asp Ala Thr Ser Ala
 65                  70                  75                  80

Gly Ala His Val Lys Asn Asp Ala Ala Leu Arg Glu Ala Lys Pro Asp
                 85                  90                  95

Ile Arg Leu Ile Asp Leu Thr Pro Ala Ala Ile Gly Pro Tyr Cys Val
            100                 105                 110

Pro Val Val Asn Leu Glu Ala Asn Val Asp Gln Leu Asn Val Asn Met
        115                 120                 125

Val Thr Cys Gly Gly Gln Ala Thr Ile Pro Met Val Ala Ala Val Ser
    130                 135                 140

Arg Val Ala Arg Val His Tyr Ala Glu Ile Ile Ala Ser Ile Ala Ser
145                 150                 155                 160

Lys Ser Ala Gly Pro Gly Thr Arg Ala Asn Ile Asp Glu Phe Thr Glu
```

```
                165                 170                 175
Thr Thr Ser Arg Ala Ile Glu Val Val Gly Ala Ala Lys Gly Lys
            180                 185                 190

Ala Ile Ile Val Leu Asn Pro Ala Glu Pro Pro Leu Met Met Arg Asp
            195                 200                 205

Thr Val Tyr Val Leu Ser Asp Glu Ala Ser Gln Asp Asp Ile Glu Ala
210                 215                 220

Ser Ile Asn Glu Met Ala Glu Ala Val Gln Ala Tyr Val Pro Gly Tyr
225                 230                 235                 240

Arg Leu Lys Gln Arg Val Gln Phe Glu Val Ile Pro Gln Asp Lys Pro
            245                 250                 255

Val Asn Leu Pro Gly Val Gly Gln Phe Ser Gly Leu Lys Thr Ala Val
            260                 265                 270

Trp Leu Glu Val Glu Gly Ala Ala His Tyr Leu Pro Ala Tyr Ala Gly
            275                 280                 285

Asn Leu Asp Ile Met Thr Ser Ser Ala Leu Ala Thr Ala Glu Lys Met
            290                 295                 300

Ala Gln Ser Leu Ala Arg Lys Ala Gly Glu Ala Ala
305                 310                 315

<210> SEQ ID NO 2
<211> LENGTH: 951
<212> TYPE: DNA
<213> ORGANISM: Escherichia coli

<400> SEQUENCE: 2
atgagtaagc gtaaagtcgc cattatcggt tctggcaaca ttggtaccga tctgatgatt      60
aaaattttgc gtcacggtca gcatctggag atggcggtga tggttggcat tgatcctcag     120
tccgacggtc tggcgcgcgc cagacgtatg ggcgtcgcca ccacccatga gggggtgatc     180
ggactgatga acatgcctga atttgctgat atcgacattg tatttgatgc gaccagcgcc     240
ggtgctcatg tgaaaaacga tgccgcttta cgcgaagcga accggatat  cgcttaatt     300 gacctgacgc ctgctgccat cggcccttac tgcgtgccgg tggttaacct cgaggcgaac     360
gtcgatcaac tgaacgtcaa catggtcacc tgcgcggcc aggccaccat tccaatggtg      420
gcggcagttt cacgcgtggc gcgtgttcat tacgccgaaa ttatcgcttc tatcgccagt     480
aaatctgccg gacctggcac gcgtgccaat atcgatgaat ttacgaaaac cacttcccga     540
gccattgaag tggtgggcgg cgcggcaaaa gggaaggcga ttattgtgct aacccagca     600 gagccaccgt tgatgatgcg tgacacggtg tatgtattga cgacgaagc ttcacaagat     660 gatatcgaag cctcaatcaa tgaaatggct gaggcggtgc aggcttacgt accgggttat     720
cgcctgaaac agcgcgtgca gtttgaagtt atcccgcagg ataaaccggt caattaccg      780 ggcgtggggc aattctccgg actgaaaaca gcggtctggc tggaagtcga aggcgcagcg     840
cattatctgc ctgcctatgc gggcaaccte gacattatga cttccagtgc gctggcgaca     900
gcggaaaaaa tggcccagtc actggcgcgc aaggcaggag aagcggcatg a              951

<210> SEQ ID NO 3
<211> LENGTH: 954
<212> TYPE: DNA
<213> ORGANISM: Artificial Sequence
<220> FEATURE:
<223> OTHER INFORMATION: Synthetic S. cevisiae optimized MhpF

<400> SEQUENCE: 3
```

```
atgtcaaagc gaaaagtagc tatcataggt tcaggtaata ttggtactga tttgatgatc    60
aaaatcctga gacatggcca gcacttggag atggccgtca tggttggtat cgacccacaa   120
tccgatggct tagctagagc taggagaatg ggtgttgcca caactcacga aggggttatt   180
ggcttaatga acatgccaga atttgcagac atcgatatag tttttgatgc tactagtgca   240
ggggcacatg tgaaaaacga cgcggcttta agagaagcca agccagatat tagattaatt   300
gatcttaccc ctgctgctat aggtccttac tgcgttcctg tagttaacct tgaagctaat   360
gtggaccagt tgaacgtgaa tatggttaca tgtggtggcc aagctaccat accaatggtt   420
gctgctgtct ctagagtggc cagagtacat tatgccgaga tcattgcgtc tatcgcatct   480
aagtctgccg gtcctggaac aagggctaac atcgatgagt tcactgagac aacctctaga   540
gctatcgaag tagtaggagg cgcagcaaaa ggtaaagcga tcattgtttt gaatcctgcc   600
gaaccacctt tgatgatgag agatacggtc tacgtgctat cagatgaagc ttcccaggat   660
gacattgaag ctagcattaa tgagatggca gaagccgttc aagcatacgt gccaggatat   720
agactcaaac aaagagtcca atttgaggtc attccacaag acaagccagt taatctccca   780
ggggtcggtc aattctcagg actaaaaact gctgtttggt tagaagtaga aggagctgct   840
cattacctac cagcctacgc cggtaatttg gatataatga catcttccgc tcttgcaaca   900
gcagaaaaga tggcacaaag tctggcccgt aaggcaggag aagcggcata ataa          954
```

<210> SEQ ID NO 4
<211> LENGTH: 75
<212> TYPE: DNA
<213> ORGANISM: Artificial Sequence
<220> FEATURE:
<223> OTHER INFORMATION: Synthetic primer 1

<400> SEQUENCE: 4

```
acaatatttc aagctatacc aagcatacaa tcaactatct catatacaat gggccgcaaa    60
ttaaagcctt cgagc                                                    75
```

<210> SEQ ID NO 5
<211> LENGTH: 75
<212> TYPE: DNA
<213> ORGANISM: Artificial Sequence
<220> FEATURE:
<223> OTHER INFORMATION: Synthetic primer 2

<400> SEQUENCE: 5

```
aatcataaga aattcgctta tttagaagtg tcaacaacgt atctaccaac gactaaaggg    60
aacaaaagct ggagc                                                    75
```

<210> SEQ ID NO 6
<211> LENGTH: 332
<212> TYPE: PRT
<213> ORGANISM: Pelodiscus sinensis japonicus

<400> SEQUENCE: 6

```
Met Ser Val Lys Glu Leu Leu Ile Gln Asn Val His Lys Glu Glu His
  1               5                  10                  15

Ser His Ala His Asn Lys Ile Thr Val Val Gly Val Gly Ala Val Gly
                 20                  25                  30

Met Ala Cys Ala Ile Ser Ile Leu Met Lys Asp Leu Ala Asp Glu Leu
             35                  40                  45

Ala Leu Val Asp Val Ile Glu Asp Lys Leu Arg Gly Glu Met Leu Asp
         50                  55                  60
```

```
Leu Gln His Gly Ser Leu Phe Leu Arg Thr Pro Lys Ile Val Ser Gly
 65                  70                  75                  80

Lys Asp Tyr Ser Val Thr Ala His Ser Lys Leu Val Ile Ile Thr Ala
                 85                  90                  95

Gly Ala Arg Gln Gln Glu Gly Glu Ser Arg Leu Asn Leu Val Gln Arg
            100                 105                 110

Asn Val Asn Ile Phe Lys Phe Ile Ile Pro Asn Val Val Lys Tyr Ser
        115                 120                 125

Pro Asp Cys Met Leu Leu Val Val Ser Asn Pro Val Asp Ile Leu Thr
130                 135                 140

Tyr Val Ala Trp Lys Ile Ser Gly Phe Pro Lys His Arg Val Ile Gly
145                 150                 155                 160

Ser Gly Cys Asn Leu Asp Ser Ala Arg Phe Arg Tyr Leu Met Gly Glu
                165                 170                 175

Lys Leu Gly Ile His Ser Leu Ser Cys His Gly Trp Ile Ile Gly Glu
            180                 185                 190

His Gly Asp Ser Ser Val Pro Val Trp Ser Gly Val Asn Val Ala Gly
        195                 200                 205

Val Ser Leu Lys Ala Leu Tyr Pro Asp Leu Gly Thr Asp Ala Asp Lys
    210                 215                 220

Glu His Trp Lys Glu Val His Lys Gln Val Val Asp Ser Ala Tyr Glu
225                 230                 235                 240

Val Ile Lys Leu Lys Gly Tyr Thr Ser Trp Ala Ile Gly Leu Ser Val
                245                 250                 255

Ala Asp Leu Ala Glu Thr Val Met Lys Asn Leu Arg Arg Val His Pro
            260                 265                 270

Ile Ser Thr Met Val Lys Gly Met Tyr Gly Val Ser Ser Asp Val Phe
        275                 280                 285

Leu Ser Val Pro Cys Val Leu Gly Tyr Ala Gly Ile Thr Asp Val Val
    290                 295                 300

Lys Met Thr Leu Lys Ser Glu Glu Glu Lys Leu Arg Lys Ser Ala
305                 310                 315                 320

Asp Thr Leu Trp Gly Ile Gln Lys Glu Leu Gln Phe
                325                 330

<210> SEQ ID NO 7
<211> LENGTH: 999
<212> TYPE: DNA
<213> ORGANISM: Pelodiscus sinensis japonicus

<400> SEQUENCE: 7
atgtccgtaa aggaactact tatacaaaac gtccataagg aggagcattc tcacgctcac      60
aataagataa cagttgtagg agtaggtgca gtaggtatgg catgtgctat ttcgatatta     120
atgaaagact tggctgatga actagccttg gttgatgtga ttgaggataa gttacgtgga     180
gaaatgttag atttgcaaca tggttcattg ttcttgagaa cccccaaaat tgtctcgggt     240
aaggattatt cagtcactgc tcattctaaa ctggttatca ttacagcagg tgcaagacag     300
caagaagggg agagcagact aaatctggtt caacgtaatg tcaacatctt caagtttatc     360
atcccgaacg tagtaaaata cagtccagac tgcatgtttc ttgttgtgag taatccagtt     420
gacatcttaa cctatgttgc gtggaaaatc agtgggtttc caaaacatag ggtgattggc     480
tcaggatgca accttgatag cgccaggttt aggtatctaa tgggagaaaa attaggtatt     540
cactccttat cttgtcatgg ctggataata ggcgaacatg gtgattcttc ggtacctgtt     600
```

```
tggtccgggg ttaatgtggc tggtgttagt ttaaaagcat tatatcctga cctgggtact      660
gatgccgata agaacattg gaaagaagtg cacaaacaag tggttgattc tgcttacgaa       720
gttattaaac ttaagggcta cacttcttgg gctataggtc tatcagtagc tgatttggca     780
gaaaccgtta tgaaaaattt aagaagagtc cacccaattt ccacgatggt caagggtatg    840
tacggtgtta gctctgacgt cttcttatct gttccttgtg ttttgggata tgcgggaatt    900
acagacgtcg tgaagatgac attgaaatca gaggaagagg aaaaactaag aaagtcagcc    960
gatactctgt ggggcattca aaaggaattg cagtttttaa                          999
```

<210> SEQ ID NO 8
<211> LENGTH: 5999
<212> TYPE: DNA
<213> ORGANISM: Artificial Sequence
<220> FEATURE:
<223> OTHER INFORMATION: Synthetic pJ1214-mhpF vector

<400> SEQUENCE: 8

```
atgcagctca gattctttgt ttgaaaaatt agcgctctcg cgttgcattt ttgttttaca      60
aaaatgaagc acagattctt cgttggtaaa atagcgcttt cgcgttgcat ttctgttctg    120
taaaaatgca gctcagattc tttgtttgaa aaattagcgc tctcgcgttg cattttgtt    180 ctacaaaatg aagcacagat gcttcgttca ggtggcactt tcggggaaa tgtgcgcgga    240 accctatttt gtttattttt ctaaatacat tcaaatatgt atccgctcat gagacaataa    300
ccctgatatt ggtcagaatt ggttaattgg ttgtaacact gaccctatt tgtttatttt     360 tctaaataca ttcaaatatg tatccgctca tgagacaata accctgataa atgcttcaat    420
aatattgaaa aaggaagaat atgagtattc aacatttccg tgtcgccctt attccctttt     480
ttgcggcatt ttgccttcct gttttgctc acccagaaac gctggtgaaa gtaaaagatg    540
ctgaagatca gttgggtgca cgagtgggtt acatcgaact ggatctcaac agcggtaaga    600
tccttgagag ttttcgcccc gaagaacgtt ttccaatgat gagcactttt aaagttctgc    660
tatgtggcgc ggtattatcc cgtattgacg ccgggcaaga gcaactcggt cgccgcatac    720
actattctca gaatgacttg gttgagtact caccagtcac agaaaagcat cttacggatg    780
gcatgacagt aagagaatta tgcagtgctg ccataaccat gagtgataac actgcggcca    840
acttacttct gacaacgatc ggaggaccga aggagctaac cgcttttttg cacaacatgg    900
gggatcatgt aactcgcctt gatcgttggg aaccggagct gaatgaagcc ataccaaacg    960
acgagcgtga caccacgatg cctgtagcga tggcaacaac gttgcgcaaa ctattaactg   1020
gcgaactact tactctagct tcccggcaac aattaataga ctggatggag gcggataaag   1080
ttgcaggacc acttctgcgc tcggcccttc cggctggctg gtttattgct gataaatccg   1140
gagccggtga gcgtggttct cgcggtatca tcgcagcgct ggggccagat ggtaagccct   1200
cccgtatcgt agttatctac acgacgggga gtcaggcaac tatggatgaa cgaaatagac   1260
agatcgctga gataggtgcc tcactgatta gcattggta actcatgacc aaaatccctt   1320
aacgtgagtt acgcgcgcgt cgttccactg agcgtcagac cccgtagaaa agatcaaagg   1380
atcttcttga tccttttttt ttctgcgcgt aatctgctgc ttgcaaacaa aaaaaccacc   1440
gctaccagcg gtggtttgtt tgccggatca agagctacca actctttttc cgaaggtaac   1500
tggcttcagc agagcgcaga taccaaatac tgttcttcta gtgtagccgt agttagccca   1560
ccacttcaag aactctgtag caccgcctac atacctcgct ctgctaatcc tgttaccagt   1620
```

-continued

```
ggctgctgcc agtggcgata agtcgtgtct taccgggttg gactcaagac gatagttacc    1680
ggataaggcg cagcggtcgg gctgaacggg gggttcgtgc acacagccca gcttggagcg    1740
aacgacctac accgaactga gatacctaca gcgtgagcta tgagaaagcg ccacgcttcc    1800
cgaagggaga aaggcggaca ggtatccggt aagcggcagg gtcggaacag gagagcgcac    1860
gagggagctt ccaggggaa acgcctggta tctttatagt cctgtcgggt ttcgccacct    1920
ctgacttgag cgtcgatttt tgtgatgctc gtcaggggg cggagcctat ggaaaaacgc     1980
cagcaacgcg gcctttttac ggttcctggc cttttgctgg ccttttgctc acatgttctt    2040
tcctgcgtta tcccctgatt ctgtggataa ccgtattacc gcctttgagt gagctgatac    2100
cgctcgggt cgtgcaggta tagcttcaaa atgtttctac tccttttta ctcttccaga      2160
ttttctcgga ctccgcgcat cgccgtacca cttcaaaaca cccaagcaca gcatactaaa    2220
tttcccctct ttcttcctct agggtgtcgt taattacccg tactaaaggt ttggaaaaga    2280
aaaaagtgac cgcctcgttt cttttcttc gtcgaaaaag gcaataaaaa tttttatcac     2340
gtttctttt cttgaaaatt tttttttttg attttttct ctttcgatga cctcccattg      2400
atatttaagt taataaacgg acttcaattt ctcaagtttc agtttcattt ttcttgttct    2460
attacaactt ttttactc ttgctcatta gaaagaaagc atagcaatct aatctaagtt      2520
taaaatgtca aagcgaaaag tagctatcat aggttcaggt aatattggta ctgatttgat    2580
gatcaaaatc ctgagacatg gccagcactt ggagatggcc gtcatggttg gtatcgaccc    2640
acaatccgat ggcttagcta gagctaggag aatgggtgtt gccacaactc acgaaggggt    2700
tattggctta atgaacatgc cagaatttgc agacatcgat atagtttttg atgctactag    2760
tgcaggggca catgtgaaaa acgacgcggc tttaagagaa gccaagccag atattagatt    2820
aattgatctt accctgctg ctataggtcc ttactgcgtt cctgtagtta accttgaagc     2880
taatgtggac cagttgaacg tgaatatggt tacatgtggt ggccaagcta ccataccaat    2940
ggttgctgct gtctctagag tggccagagt acattatgcc gagatcattg cgtctatcgc    3000
atctaagtct gccggtcctg gaacaagggc taacatcgat gagttcactg agacaacctc    3060
tagagctatc gaagtagtag gaggcgcagc aaaaggtaaa gcgatcattg ttttgaatcc    3120
tgccgaacca cctttgatga tgagagatac ggtctacgtg ctatcagatg aagcttccca    3180
ggatgacatt gaagctagca ttaatgagat ggcagaagcc gttcaagcat acgtgccagg    3240
atatagactc aaacaaagag tccaatttga ggtcattcca caagacaagc cagttaatct    3300
cccagggggtc ggtcaattct caggactaaa aactgctgtt tggttagaag tagaaggagc   3360
tgctcattac ctaccagcct acgccggtaa tttggatata atgacatctt ccgctcttgc    3420
aacagcagaa aagatggcac aaagtctggc ccgtaaggca ggagaagcgg cataataaat    3480
catgtaatta gttatgtcac gcttacattc acgccctccc ccacatccg ctctaaccga     3540
aaaggaagga gttagacaac ctgaagtcta ggtccctatt tattttttta tagttatgtt    3600
agtattaaga acgttattta tatttcaaat ttttctttt tttctgtaca gacgcgtgta    3660
cgcatgtaac attatactga aaaccttgct tgagaaggtt ttgggacgct cgaaggcttt    3720
aatttgcggc ccctcacctg cacgcaaaaa gcttttcaat tcaattcatc attttttttt    3780
tattcttttt tttgatttcg gtttctttga aattttttg attcggtaat ctccgaacag    3840
aaggaagaac gaaggaagga gcacagactt agattggtat atatacgcat atgtagtgtt    3900
gaagaaacat gaaattgccc agtattctta acccaactgc acagaacaaa accagcagg    3960
aaacgaagat aaatcatgtc gaaagctaca tataaggaac gtgctgctac tcatcctagt    4020
```

```
cctgttgctg ccaagctatt taatatcatg cacgaaaagc aaacaaactt gtgtgcttca    4080
ttggatgttc gtaccaccaa ggaattactg gagttagttg aagcattagg tcccaaaatt    4140
tgtttactaa aaacacatgt ggatatcttg actgattttt ccatggaggg cacagttaag    4200
ccgctaaagg cattatccgc caagtacaat tttttactct tcgaagatag aaaatttgct    4260
gacattggta atacagtcaa attgcagtac tctgcgggtg tatacagaat agcagaatgg    4320
gcagacatta cgaatgcaca cggtgtggtg ggcccaggta ttgttagcgg tttgaagcag    4380
gcggcagaag aagtaacaaa ggaacctaga ggccttttga tgttagcaga attgtcatgc    4440
aagggctccc tatctactgg agaatatact aagggtactg ttgacattgc gaaaagcgac    4500
aaagattttg ttatcggctt tattgctcaa agagacatgg gtggaagaga tgaaggttac    4560
gattggttga ttatgacacc cggtgtgggt ttagatgaca agggagatgc attgggtcaa    4620
cagtatagaa ccgtggatga tgttgtctct acaggatctg acattattat tgttggaaga    4680
ggactatttg caaagggaag ggatgctaag gtagagggtg aacgttacag aaaagcaggc    4740
tgggaagcat atttgagaag atgcggccag caaaactaaa aaactgtatt ataagtaaat    4800
gcatgtatac taaactcaca aattagagct tcaatttaat tatatcagtt attacccacg    4860
ctatgatcca atatcaaagg aaatgatagc attgaaggat gagactaatc caattgagga    4920
gtggcagcat atagaacagc taagggtag tgctgaagga agcatacgat accccgcatg    4980
gaatgggata atatcacagg aggtactaga ctaccttttca tcctacataa atagacgcat    5040
ataagtacgc atttaagcat aaacacgcac tatgccgttc ttctcatgta tatatatata    5100
caggcaacac gcagatatag gtgcgacgtg aacagtgagc tgtatgtgcg cagctcgcgt    5160
tgcattttcg gaagcgctcg ttttcggaaa cgctttgaag ttcctattcc gaagttccta    5220
ttctctagaa agtataggaa cttcagagcg cttttgaaaa ccaaaagcgc tctgaagtcg    5280
cactttcaaa aaaccaaaaa cgcaccggac tgtaacgagc tactaaaata ttgcgaatac    5340
cgcttccaca aacattgctc aaaagtatct ctttgctata tatctctgtg ctatatccct    5400
atataaccta cccatccacc tttcgctcct tgaacttgca tctaaactcg acctctacat    5460
tttttatgtt tatctctagt attactcttt agacaaaaaa attgtagtaa gaactattca    5520
tagagtgaat cgaaaacaat acgaaaatgt aaacatttcc tatacgtagt atatagagac    5580
aaaatagaag aaaccgttca taattttctg accaatgaag aatcatcaac gctatcactt    5640
tctgttcaca agtatgcgc aatccacatc ggtatagaat ataatcgggg atgcctttat    5700
cttgaaaaaa tgcacccgca gcttcgctag taatcagtaa acgcgggaag tggagtcagg    5760 cttttttat ggaagagaaa atagacacca aagtagcctt cttctaacct taacggacct    5820
acagtgcaaa aagttatcaa gagactgcat tatagagcgc acaaggaga aaaaagtaa     5880 tctaagatgc tttgttagaa aaatagcgct ctcgggatgc attttttgtag aacaaaaaag    5940 aagtatagat tctttgttgg taaaatagcg ctctcgcgtt gcatttctgt tctgtaaaa     5999
```

<210> SEQ ID NO 9
<211> LENGTH: 292
<212> TYPE: DNA
<213> ORGANISM: Artificial Sequence
<220> FEATURE:
<223> OTHER INFORMATION: Synthetic CCW12 promoter

<400> SEQUENCE: 9

```
ttcgcggcca cctacgccgc tatctttgca acaactatct gcgataactc agcaaatttt      60
```

```
gcatattcgt gttgcagtat tgcgataatg ggagtcttac ttccaacata acggcagaaa    120
gaaatgtgag aaaattttgc atcctttgcc tccgttcaag tatataaagt cggcatgctt    180
gataatcttt ctttccatcc tacattgttc taattattct tattctcctt tattctttcc    240
taacatacca agaaattaat cttctgtcat tcgcttaaac actatatcaa ta            292
```

<210> SEQ ID NO 10
<211> LENGTH: 955
<212> TYPE: DNA
<213> ORGANISM: Artificial Sequence
<220> FEATURE:
<223> OTHER INFORMATION: Synthetic PDC1 promoter

<400> SEQUENCE: 10

```
agggtagcct ccccataaca taaactcaat aaaatatata gtcttcaact tgaaaaagga     60
acaagctcat gcaaagaggt ggtacccgca cgccgaaatg catgcaagta acctattcaa    120
agtaatatct catacatgtt tcatgagggt aacaacatgc gactgggtga gcatatgttc    180
cgctgatgtg atgtgcaaga taacaagca agacagaaac taacttcttc ttcatgtaat    240
aaacacaccc cgcgtttatt tacctatctc taaacttcaa caccttatat cataactaat    300
atttcttgag ataagcacac tgcacccata ccttccttaa aaacgtagct tccagttttt    360
ggtggttctg gcttccttcc cgattccgcc cgctaaacgc ataattttgt tgcctggtgg    420
catttgcaaa atgcataacc tatgcattta aaagattatg tatgctcttc tgactttcg     480 tgtgatgagg ctcgtggaaa aaatgaataa tttatgaatt tgagaacaat tttgtgttgt    540
tacggtattt tactatggaa taatcaatca attgaggatt ttatgcaaat atcgtttgaa    600
tatttttccg acccttgag tacttttctt cataattgca taatattgtc cgctgcccgt     660
ttttctgtta gacggtgtct tgatctactt gctatcgttc aacaccacct tatttttctaa   720 ctatttttt tttagctcat ttgaatcagc ttatggtgat ggcacatttt tgcataaacc     780
tagctgtcct cgttgaacat aggaaaaaaa aatatataaa caaggctctt tcactctcct    840
tggaatcaga tttgggtttg ttcccttat tttcatattt cttgtcatat tcttttctca     900
attattatct tctactcata acctcacgca aaataacaca gtcaaatcaa tcaaa         955
```

<210> SEQ ID NO 11
<211> LENGTH: 401
<212> TYPE: DNA
<213> ORGANISM: Artificial Sequence
<220> FEATURE:
<223> OTHER INFORMATION: Synthetic TEF1 promoter

<400> SEQUENCE: 11

```
atagcttcaa aatgtttcta ctcctttttt actcttccag attttctcgg actccgcgca     60
tcgccgtacc acttcaaaac acccaagcac agcatactaa atttcccctc tttcttcctc    120
tagggtgtcg ttaattaccc gtactaaagg tttggaaaag aaaaaagaga ccgcctcgtt    180
tctttttctt cgtcgaaaaa ggcaataaaa atttttatca cgtttctttt tcttgaaaat    240
tttttttttg atttttttct ctttcgatga cctcccattg atatttaagt taataaacgg    300
tcttcaattt ctcaagtttc agtttcattt ttcttgttct attacaactt tttttacttc    360
ttgctcatta gaaagaaagc atagcaatct aatctaagtt t                        401
```

<210> SEQ ID NO 12
<211> LENGTH: 798
<212> TYPE: DNA
<213> ORGANISM: Artificial Sequence

```
<220> FEATURE:
<223> OTHER INFORMATION: Synthetic PGK1 promoter

<400> SEQUENCE: 12
ctttcctctt tttattaacc ttaattttta ttttagattc ctgacttcaa ctcaagacgc      60
acagatatta taacatctgc ataataggca tttgcaagaa ttactcgtga gtaaggaaag     120
agtgaggaac tatcgcatac ctgcatttaa agatgccgat ttgggcgcga atcctttatt    180
ttggcttcac cctcatacta ttatcagggc cagaaaaagg aagtgtttcc ctccttcttg     240
aattgatgtt accctcataa agcacgtggc ctcttatcga gaaagaaatt accgtcgctc     300
gtgatttgtt tgcaaaaaga acaaaactga aaaaacccag acacgctcga cttcctgtct     360
tcctattgat tgcagcttcc aatttcgtca cacaacaagg tcctagcgac ggctcacagg     420
ttttgtaaca agcaatcgaa ggttctggaa tggcgggaaa gggtttagta ccacatgcta     480
tgatgcccac tgtgatctcc agagcaaagt tcgttcgatc gtactgttac tctctctctt     540
tcaaacagaa ttgtccgaat cgtgtgacaa caacagcctg ttctcacaca ctctttttctt    600 ctaaccaagg gggtggttta gtttagtaga acctcgtgaa acttacattt acatatatat    660
aaacttgcat aaattggtca atgcaagaaa tacatatttg gtcttttcta attcgtagtt    720
tttcaagttc ttagatgctt tctttttctc tttttttacag atcatcaagg aagtaattat   780 ctactttta caacaaat                                                    798

<210> SEQ ID NO 13
<211> LENGTH: 31
<212> TYPE: DNA
<213> ORGANISM: Artificial Sequence
<220> FEATURE:
<223> OTHER INFORMATION: Synthetic primer 3

<400> SEQUENCE: 13
cgagctcttc gcggccacct acgccgctat c                                    31

<210> SEQ ID NO 14
<211> LENGTH: 32
<212> TYPE: DNA
<213> ORGANISM: Artificial Sequence
<220> FEATURE:
<223> OTHER INFORMATION: Synthetic primer

<400> SEQUENCE: 14
gctctagata ttgatatagt gtttaagcga at                                   32

<210> SEQ ID NO 15
<211> LENGTH: 27
<212> TYPE: DNA
<213> ORGANISM: Artificial Sequence
<220> FEATURE:
<223> OTHER INFORMATION: Synthetic Primer 5

<400> SEQUENCE: 15
cggccatggc gggagctcgc atgcaag                                         27

<210> SEQ ID NO 16
<211> LENGTH: 28
<212> TYPE: DNA
<213> ORGANISM: Artificial Sequence
<220> FEATURE:
<223> OTHER INFORMATION: Synthetic Primer 6

<400> SEQUENCE: 16
```
cgggatatca ctagtgagct cgctccgc                                        28

<210> SEQ ID NO 17
<211> LENGTH: 2321
<212> TYPE: DNA
<213> ORGANISM: Artificial Sequence
<220> FEATURE:
<223> OTHER INFORMATION: Synthetic HPH cassette

<400> SEQUENCE: 17
gccgggagag ctcgcatgca agtaacctat tcaaagtaat atctcataca tgtttcatga      60
gggtaacaac atgcgactgg gtgagcatat gttccgctga tgtgatgtgc aagataaaca     120
agcaaggcag aaactaactt cttcttcatg taataaacac ccccgcgtt tatttaccta      180
tctctaaact tcaacacctt atatcataac taatatttct tgagataagc acactgcacc    240
cataccttcc ttaaaaacgt agcttccagt ttttggtggt tccggcttcc ttcccgattc    300
cgcccgctaa acgcatattt tgttgcctg gtggcatttg caaaatgcat aacctatgca     360
tttaaaagat tatgtatgct cttctgactt ttcgtgtgat gaggctcgtg aaaaaatga    420
ataatttatg aatttgagaa caattttgtg ttgttacggt attttactat ggaataatca     480
atcaattgag gattttatgc aaatatcgtt tgaatatttt tccgaccctt tgagtacttt     540
tcttcataat tgcataatat tgtccgctgc ccctttttct gttagacggt gtcttgatct    600
acttgctatc gttcaacacc acctattttt ctaactattt tttttttagc tcatttgaat    660
cagcttatgg tgatggcaca ttttttgcata aacctagctg tcctcgttga acataggaaa   720
aaaaaatata taaacaaggc tctttcactc tccttgcaat cagatttggg tttgttccct   780
ttattttcat atttcttgtc atattccttt ctcaattatt attttctact cataacctca    840
cgcaaaataa cacagtcaaa tcctcgagat gaaaaagcct gaactcaccg cgacgtctgt    900
cgagaagttt ctgatcgaaa agttcgacag cgtctccgac ctgatgcagc tctcggaggg    960
cgaagaatct cgtgctttca gcttcgatgt aggagggcgt ggatatgtcc tgcgggtaaa   1020
tagctgcgcc gatggtttct acaaagatcg ttatgtttat cggcactttg catcggccgc   1080
gctcccgatt ccggaagtgc ttgacattgg ggaattcagc gagagcctga cctattgcat   1140
ctcccgccgt gcacagggtg tcacgttgca agacctgcct gaaaccgaac tgcccgctgt   1200
tctgcagccg gtcgcggagg ccatggatgc gatcgctgcg gccgatctta gccagacgag   1260
cgggttcggc ccattcggac cgcaaggaat cggtcaatac actacatggc gtgatttcat   1320
atgcgcgatt gctgatcccc atgtgtatca ctggcaaact gtgatggacg acaccgtcag   1380
tgcgtccgtc gcgcaggctc tcgatgagct gatgctttgg gccgaggact gccccgaagt   1440
ccggcacctc gtgcacgcgg atttcggctc aacaatgtc ctgacggaca atggccgcat    1500
aacagcggtc attgactgga gcgaggcgat gttcggggat tcccaatacg aggtcgccaa   1560
catcttcttc tggaggccgt ggttggcttg tatggagcag cagacgcgct acttcgagcg   1620
gaggcatccg gagcttgcag gatcgccgcg gctccgggcg tatatgctcc gcattggtct   1680
tgaccaactc tatcagagct tggttgacgg caatttcgat gatgcagctt gggcgcaggg   1740
tcgatgcgac gcaatcgtcc gatccggagc cgggactgtc gggcgtacac aaatcgcccg   1800
cagaagcgcg gccgtctgga ccgatggctg tgtagaagta ctcgccgata gtggaaaccg   1860
acgccccagc actcgtccgg atcgggagat gggggaggct aactgaggat ccgtagatac   1920
attgatgcta tcaatcaaga gaactggaaa gattgtgtaa ccttgaaaaa cggtgaaact   1980
tacgggtcca agattgtcta cagatttttcc tgatttgcca gcttactatc cttcttgaaa   2040

```
atatgcactc tatatctttt agttcttaat tgcaacacat agatttgctg tataacgaat    2100
tttatgctat tttttaaatt tggagttcag tgataaaagt gtcacagcga atttcctcac    2160
atgtagggac cgaattgttt acaagttctc tgtaccacca tggagacatc aaaaattgaa    2220
aatctatgga agatatgga cggtagcaac aagaatatag cacgagccgc ggagcgagct    2280
cggccgcact agtgatatcc cgcggccatg gcggccggga g                       2321
```

<210> SEQ ID NO 18
<211> LENGTH: 18
<212> TYPE: DNA
<213> ORGANISM: Artificial Sequence
<220> FEATURE:
<223> OTHER INFORMATION: Synthetic primer 7

<400> SEQUENCE: 18

```
tgctgtcttg ctatcaag                                                    18
```

<210> SEQ ID NO 19
<211> LENGTH: 19
<212> TYPE: DNA
<213> ORGANISM: Artificial Sequence
<220> FEATURE:
<223> OTHER INFORMATION: Synthetic Primer 8

<400> SEQUENCE: 19

```
caggaaagag ttactcaag                                                   19
```

<210> SEQ ID NO 20
<211> LENGTH: 20
<212> TYPE: DNA
<213> ORGANISM: Artificial Sequence
<220> FEATURE:
<223> OTHER INFORMATION: Synthetic Primer 9

<400> SEQUENCE: 20

```
atgtcaaagc gaaaagtagc                                                  20
```

<210> SEQ ID NO 21
<211> LENGTH: 20
<212> TYPE: DNA
<213> ORGANISM: Artificial Sequence
<220> FEATURE:
<223> OTHER INFORMATION: Synthetic Primer 10

<400> SEQUENCE: 21

```
atttattatg ccgcttctcc                                                  20
```

<210> SEQ ID NO 22
<211> LENGTH: 18
<212> TYPE: DNA
<213> ORGANISM: Artificial Sequence
<220> FEATURE:
<223> OTHER INFORMATION: Synthetic Primer 11

<400> SEQUENCE: 22

```
gaaacagcta tgaccatg                                                    18
```

<210> SEQ ID NO 23
<211> LENGTH: 32
<212> TYPE: DNA
<213> ORGANISM: Artificial Sequence
<220> FEATURE:
<223> OTHER INFORMATION: Synthetic Primer 12

<400> SEQUENCE: 23

```
gacatgacga gctcgaattg ggtaccggcc gc                                32
```

<210> SEQ ID NO 24
<211> LENGTH: 4173
<212> TYPE: DNA
<213> ORGANISM: Artificial Sequence
<220> FEATURE:
<223> OTHER INFORMATION: Synthetic pUC57-Ura3HA vector

<400> SEQUENCE: 24

```
gatgacggtg aaaacctctg acacatgcag ctcccggaga cggtcacagc ttgtctgtaa    60
gcggatgccg ggagcagaca gcccgtcag ggcgcgtcag cgggtgttgg cgggtgtcgg    120
ggctggctta actatgcggc atcagagcag attgtactga gagtgcacca tatgcggtgt   180
gaaataccgc acagatgcgt aaggagaaaa taccgcatca ggcgccattc gccattcagg   240
ctgcgcaact gttgggaagg cgatcggtg cgggcctctt cgctattacg ccagctggcg    300
aaaggggggat gtgctgcaag gcgattaagt tgggtaacgc cagggttttc ccagtcacga   360
cgttgtaaaa cgacggccag tgaattcgag ctcggtacct cgcgaatgca tctagatatc   420
ggatcccgac gagctgcacc gcggtggcgg ccgtatcttt acccatacg atgttcctga    480
ctatgcgggc tatccctatg acgtcccgga ctatgcagga tcctatccat atgacgttcc   540
agattacgct gctcagtgcg gccgcctgag agtgcaccat accacagctt tcaattcaa    600
ttcatcattt ttttttttatt cttttttttg atttcggttt ctttgaaatt ttttttgattc   660
ggtaatctcc gaacagaagg aagaacgaag gaaggagcac agacttagat tggtatatat   720
acgcatatgt agtgttgaag aaacatgaaa ttgcccagta ttcttaaccc aactgcacag   780
aacaaaaacc tgcaggaaac gaagataaat catgtcgaaa gctacatata aggaacgtgc   840
tgctactcat cctagtcctg ttgctgccaa gctatttaat atcatgcacg aaaagcaaac   900
aaacttgtgt gcttcattgg atgttcgtac caccaaggaa ttactggagt tagttgaagc   960
attaggtccc aaaatttgtt tactaaaaac acatgtggat atcttgactg attttttccat  1020
ggagggcaca gttaagccgc taaaggcatt atccgccaag tacaatttt tactcttcga   1080
agacagaaaa tttgctgaca ttggtaatac agtcaaattg cagtactctg cgggtgtata  1140
cagaatagca gaatgggcag acattacgaa tgcacgggt gtggtgggcc caggtattgt  1200
tagcggtttg aagcaggcgg cagaagaagt aacaaaggaa cctagaggcc ttttgatgtt  1260
agcagaattg tcatgcaagg gctccctatc tactggagaa tatactaagg gtactgttga  1320
cattgcgaag agcgacaaag attttgttat cggcttatt gctcaaagag acatgggtgg  1380
aagagatgaa ggttacgatt ggttgattat gacacccgt gtgggtttag atgcaagggg  1440
agacgcattg ggtcaacagt atagaaccgt ggatgatgtg gtctctacag atctgacat   1500
tattattgtt ggaagaggac tatttgcaaa gggaagggat gctaaggtag agggtgaacg  1560
ttacagaaaa gcaggctggg aagcatattt gagaagatgc ggccagcaaa actaaaaaac  1620
tgtattataa gtaaatgcat gtatactaaa ctcacaaatt agagcttcaa tttaattata  1680
tcagttatta ccctatgcgg tgtgaaatac cgcacagatg cgtaaggaga aataccgca   1740
tcaggaaatt gtagcggccg cgaatttgag cttatctttt acccatacga tgttcctgac  1800
tatgcgggct atccctatga cgtcccggac tatgcaggat cctatccata tgacgttcca  1860
gattacgcta ctagcggggg gcccggtgac gggcccgtcg actgcagagg cctgcatgca  1920
agcttggcgt aatcatggtc atagctgttt cctgtgtgaa attgttatcc gctcacaatt  1980
```

```
ccacacaaca tacgagccgg aagcataaag tgtaaagcct ggggtgccta atgagtgagc    2040
taactcacat taattgcgtt gcgctcactg cccgctttcc agtcgggaaa cctgtcgtgc    2100
cagctgcatt aatgaatcgg ccaacgcgcg gggagaggcg gtttgcgtat tgggcgctct    2160
tccgcttcct cgctcactga ctcgctgcgc tcggtcgttc ggctgcggcg agcggtatca    2220
gctcactcaa aggcggtaat acggttatcc acagaatcag gggataacgc aggaaagaac    2280
atgtgagcaa aaggccagca aaaggccagg aaccgtaaaa aggccgcgtt gctggcgttt    2340
ttccataggc tccgcccccc tgacgagcat cacaaaaatc gacgctcaag tcagaggtgg    2400
cgaaacccga caggactata aagataccag gcgtttcccc ctggaagctc cctcgtgcgc    2460
tctcctgttc cgaccctgcc gcttaccgga tacctgtccg cctttctccc ttcgggaagc    2520
gtggcgcttt ctcatagctc acgctgtagg tatctcagtt cggtgtaggt cgttcgctcc    2580
aagctgggct gtgtgcacga accccccgtt cagcccgacc gctgcgcctt atccggtaac    2640
tatcgtcttg agtccaaccc ggtaagacac gacttatcgc cactggcagc agccactggt    2700
aacaggatta gcagagcgag gtatgtaggc ggtgctacag agttcttgaa gtggtggcct    2760
aactacggct acactagaag aacagtattt ggtatctgcg ctctgctgaa gccagttacc    2820
ttcggaaaaa gagttggtag ctcttgatcc ggcaaacaaa ccaccgctgg tagcggtggt    2880
ttttttgttt gcaagcagca gattacgcgc agaaaaaaag gatctcaaga agatcctttg    2940
atcttttcta cggggtctga cgctcagtgg aacgaaaact cacgttaagg gattttggtc    3000
atgagattat caaaaaggat cttcacctag atccttttaa attaaaaatg aagttttaaa    3060
tcaatctaaa gtatatatga gtaaacttgg tctgacagtt accaatgctt aatcagtgag    3120
gcacctatct cagcgatctg tctatttcgt tcatccatag ttgcctgact ccccgtcgtg    3180
tagataacta cgatacggga gggcttacca tctggcccca gtgctgcaat gataccgcga    3240
gacccacgct caccggctcc agatttatca gcaataaacc agccagccgg aagggccgag    3300
cgcagaagtg gtcctgcaac tttatccgcc tccatccagt ctattaattg ttgccgggaa    3360
gctagagtaa gtagttcgcc agttaatagt ttgcgcaacg ttgttgccat tgctacaggc    3420
atcgtggtgt cacgctcgtc gtttggtatg gcttcattca gctccggttc caacgatca    3480
aggcgagtta catgatcccc catgttgtgc aaaaaagcgg ttagctcctt cggtcctccg    3540
atcgttgtca gaagtaagtt ggccgcagtg ttatcactca tggttatggc agcactgcat    3600
aattctctta ctgtcatgcc atccgtaaga tgcttttctg tgactggtga gtactcaacc    3660
aagtcattct gagaatagtg tatgcggcga ccgagttgct cttgcccggc gtcaatacgg    3720
gataataccg cgccacatag cagaacttta aaagtgctca tcattggaaa acgttcttcg    3780
gggcgaaaac tctcaaggat cttaccgctg ttgagatcca gttcgatgta acccactcgt    3840
gcacccaact gatcttcagc atcttttact ttcaccagcg tttctgggtg agcaaaaaca    3900
ggaaggcaaa atgccgcaaa aaagggaata agggcgacac ggaaatgttg aatactcata    3960
ctcttccttt ttcaatatta ttgaagcatt tatcagggtt attgtctcat gagcggatac    4020
atatttgaat gtatttagaa aaataaacaa atagggggttc gcgcacatt tccccgaaaa    4080
gtgccacctg acgtctaaga aaccattatt atcatgacat taacctataa aataggcgt    4140
atcacgaggc cctttcgtct cgcgcgtttc ggt                                 4173
```

<210> SEQ ID NO 25
<211> LENGTH: 62
<212> TYPE: DNA

```
<213> ORGANISM: Artificial Sequence
<220> FEATURE:
<223> OTHER INFORMATION: Synthetic Primer 13

<400> SEQUENCE: 25
gcttataaaa ctttaactaa taattagaga ttaaatcgct taaggtttcc cgactggaaa    60
gc                                                                   62

<210> SEQ ID NO 26
<211> LENGTH: 64
<212> TYPE: DNA
<213> ORGANISM: Artificial Sequence
<220> FEATURE:
<223> OTHER INFORMATION: Synthetic Primer 14

<400> SEQUENCE: 26
ctactcataa cctcacgcaa aataacacag tcaaatcaat caaaccagtc acgacgttgt    60
aaaa                                                                 64

<210> SEQ ID NO 27
<211> LENGTH: 20
<212> TYPE: DNA
<213> ORGANISM: Artificial Sequence
<220> FEATURE:
<223> OTHER INFORMATION: Synthetic Primer 15

<400> SEQUENCE: 27
ggacgtaaag ggtagcctcc                                                20

<210> SEQ ID NO 28
<211> LENGTH: 22
<212> TYPE: DNA
<213> ORGANISM: Artificial Sequence
<220> FEATURE:
<223> OTHER INFORMATION: Synthetic Primer 16

<400> SEQUENCE: 28
gaagcggacc cagacttaag cc                                             22

<210> SEQ ID NO 29
<211> LENGTH: 65
<212> TYPE: DNA
<213> ORGANISM: Artificial Sequence
<220> FEATURE:
<223> OTHER INFORMATION: Synthetic Primer 17

<400> SEQUENCE: 29
ccgaaatgat tccctttcct gcacaacacg agatctttca cgcatccagt cacgacgttg    60
taaaa                                                                65

<210> SEQ ID NO 30
<211> LENGTH: 65
<212> TYPE: DNA
<213> ORGANISM: Artificial Sequence
<220> FEATURE:
<223> OTHER INFORMATION: Synthetic Primer 18

<400> SEQUENCE: 30
aaagtagcct taaagctagg ctataatcat gcatcctcaa attctaggtt tcccgactgg    60
aaagc                                                                65

<210> SEQ ID NO 31
<211> LENGTH: 25
```

```
<212> TYPE: DNA
<213> ORGANISM: Artificial Sequence
<220> FEATURE:
<223> OTHER INFORMATION: Synthetic Primer 19

<400> SEQUENCE: 31
cgcaagaacg tagtatccac atgcc                                          25

<210> SEQ ID NO 32
<211> LENGTH: 21
<212> TYPE: DNA
<213> ORGANISM: Artificial Sequence
<220> FEATURE:
<223> OTHER INFORMATION: Synthetic Primer 20

<400> SEQUENCE: 32
ggatatttac agaacgatgc g                                              21

<210> SEQ ID NO 33
<211> LENGTH: 70
<212> TYPE: DNA
<213> ORGANISM: Artificial Sequence
<220> FEATURE:
<223> OTHER INFORMATION: Synthetic Primer 21

<400> SEQUENCE: 33
ccctatgtct ctggccgatc acgcgccatt gtccctcaga aacaaatcaa ccagtcacga    60
cgttgtaaaa                                                           70

<210> SEQ ID NO 34
<211> LENGTH: 70
<212> TYPE: DNA
<213> ORGANISM: Artificial Sequence
<220> FEATURE:
<223> OTHER INFORMATION: Synthetic Primer 22

<400> SEQUENCE: 34
tagaagcaac tgtgccgaca gcctctgaat gagtggtgtt gtaaccaccc aggtttcccg    60
actggaaagc                                                           70

<210> SEQ ID NO 35
<211> LENGTH: 25
<212> TYPE: DNA
<213> ORGANISM: Artificial Sequence
<220> FEATURE:
<223> OTHER INFORMATION: Synthetic Primer 23

<400> SEQUENCE: 35
tcaatgagac tgttgtcctc ctact                                          25

<210> SEQ ID NO 36
<211> LENGTH: 24
<212> TYPE: DNA
<213> ORGANISM: Artificial Sequence
<220> FEATURE:
<223> OTHER INFORMATION: Synthetic Primer 24

<400> SEQUENCE: 36
tacatccttg tcgagccttg ggca                                           24

<210> SEQ ID NO 37
<211> LENGTH: 332
<212> TYPE: PRT
<213> ORGANISM: Ornithorhynchus anatinus
```

<400> SEQUENCE: 37

```
Met Ala Gly Val Lys Glu Gln Leu Ile Gln Asn Leu Leu Lys Glu Glu
 1               5                  10                  15
Tyr Ala Pro Gln Asn Lys Ile Thr Val Val Gly Val Gly Ala Val Gly
                20                  25                  30
Met Ala Cys Ala Ile Ser Ile Leu Met Lys Asp Leu Ala Asp Glu Leu
             35                  40                  45
Ala Leu Val Asp Val Ile Glu Asp Lys Leu Lys Gly Glu Met Met Asp
         50                  55                  60
Leu Gln His Gly Ser Leu Phe Leu Arg Thr Pro Lys Ile Val Ser Gly
 65                  70                  75                  80
Lys Asp Tyr Ser Val Thr Ala Asn Ser Lys Leu Val Ile Ile Thr Ala
                 85                  90                  95
Gly Ala Arg Gln Gln Glu Gly Glu Ser Arg Leu Asn Leu Val Gln Arg
            100                 105                 110
Asn Val Asn Ile Phe Lys Phe Ile Ile Pro Asn Val Val Lys Tyr Ser
            115                 120                 125
Pro Asn Cys Lys Leu Leu Val Val Ser Asn Pro Val Asp Ile Leu Thr
        130                 135                 140
Tyr Val Ala Trp Lys Ile Ser Gly Phe Pro Lys Asn Arg Val Ile Gly
145                 150                 155                 160
Ser Gly Cys Asn Leu Asp Ser Ala Arg Phe Arg Tyr Leu Met Gly Glu
                165                 170                 175
Arg Leu Gly Ile His Ser Thr Ser Cys His Gly Trp Val Ile Gly Glu
            180                 185                 190
His Gly Asp Ser Ser Val Pro Val Trp Ser Gly Val Asn Val Ala Gly
        195                 200                 205
Val Ser Leu Lys Asn Leu His Pro Asp Leu Gly Thr Asp Ala Asp Lys
    210                 215                 220
Glu Gln Trp Lys Asp Val His Lys Gln Val Val Asp Ser Ala Tyr Glu
225                 230                 235                 240
Val Ile Lys Leu Lys Gly Tyr Thr Ser Trp Ala Ile Gly Leu Ser Val
                245                 250                 255
Ala Asp Leu Ala Glu Ser Ile Val Lys Asn Leu Arg Arg Val His Pro
            260                 265                 270
Ile Ser Thr Met Ile Lys Gly Leu Tyr Gly Ile Lys Asp Glu Val Phe
        275                 280                 285
Leu Ser Val Pro Cys Val Leu Gly Gln Asn Gly Ile Ser Asp Val Val
    290                 295                 300
Lys Ile Thr Leu Lys Ser Glu Glu Glu Ala His Leu Lys Lys Ser Ala
305                 310                 315                 320
Asp Thr Leu Trp Gly Ile Gln Lys Glu Leu Gln Phe
                325                 330
```

<210> SEQ ID NO 38
<211> LENGTH: 332
<212> TYPE: PRT
<213> ORGANISM: Tursiops truncatus

<400> SEQUENCE: 38

```
Met Ala Thr Val Lys Asp Gln Leu Ile Gln Asn Leu Leu Lys Glu Glu
 1               5                  10                  15
His Val Pro Gln Asn Lys Ile Thr Val Val Gly Val Gly Ala Val Gly
                20                  25                  30
```

```
Met Ala Cys Ala Ile Ser Ile Leu Met Lys Asp Leu Ala Asp Glu Leu
            35                  40                  45

Ala Leu Val Asp Val Ile Glu Asp Lys Leu Lys Gly Glu Met Met Asp
 50                  55                  60

Leu Gln His Gly Ser Leu Phe Leu Arg Thr Pro Lys Ile Val Ser Gly
 65                  70                  75                  80

Lys Asp Tyr Ser Val Thr Ala Asn Ser Lys Leu Val Ile Ile Thr Ala
                 85                  90                  95

Gly Ala Arg Gln Gln Glu Gly Glu Ser Arg Leu Asn Leu Val Gln Arg
            100                 105                 110

Asn Val Asn Ile Phe Lys Phe Ile Val Pro Asn Ile Val Lys Tyr Ser
            115                 120                 125

Pro His Cys Lys Leu Leu Val Val Ser Asn Pro Val Asp Ile Leu Thr
130                 135                 140

Tyr Val Ala Trp Lys Ile Ser Gly Phe Pro Lys Asn Arg Val Ile Gly
145                 150                 155                 160

Ser Gly Cys Asn Leu Asp Ser Ala Arg Phe Arg Tyr Leu Met Gly Glu
                165                 170                 175

Arg Leu Gly Val His Pro Leu Ser Cys His Gly Trp Ile Leu Gly Glu
            180                 185                 190

His Gly Asp Ser Ser Val Pro Val Trp Ser Gly Val Asn Val Ala Gly
            195                 200                 205

Val Ser Leu Lys Asn Leu His Pro Glu Leu Gly Thr Asp Ala Asp Lys
210                 215                 220

Glu His Trp Lys Ala Ile His Lys Gln Val Val Asp Ser Ala Tyr Glu
225                 230                 235                 240

Val Ile Lys Leu Lys Gly Tyr Thr Ser Trp Ala Val Gly Leu Ser Val
                245                 250                 255

Ala Asp Leu Ala Glu Ser Ile Met Lys Asn Leu Arg Arg Val His Pro
            260                 265                 270

Ile Ser Thr Met Ile Lys Gly Leu Tyr Gly Ile Lys Glu Asp Val Phe
            275                 280                 285

Leu Ser Val Pro Cys Ile Leu Gly Gln Asn Gly Ile Ser Asp Val Val
290                 295                 300

Lys Val Thr Leu Thr Pro Glu Glu Gln Ala Cys Leu Lys Lys Ser Ala
305                 310                 315                 320

Asp Thr Leu Trp Gly Ile Gln Lys Glu Leu Gln Phe
                325                 330

<210> SEQ ID NO 39
<211> LENGTH: 332
<212> TYPE: PRT
<213> ORGANISM: Rattus norvegicus

<400> SEQUENCE: 39

Met Ala Ala Leu Lys Asp Gln Leu Ile Val Asn Leu Leu Lys Glu Glu
  1               5                  10                  15

Gln Val Pro Gln Asn Lys Ile Thr Val Val Gly Val Gly Ala Val Gly
             20                  25                  30

Met Ala Cys Ala Ile Ser Ile Leu Met Lys Asp Leu Ala Asp Glu Leu
            35                  40                  45

Ala Leu Val Asp Val Ile Glu Asp Lys Leu Lys Gly Glu Met Met Asp
 50                  55                  60

Leu Gln His Gly Ser Leu Phe Leu Lys Thr Pro Lys Ile Val Ser Ser
 65                  70                  75                  80
```

| | | | | | | | | | | |
|---|---|---|---|---|---|---|---|---|---|---|
|Lys|Asp|Tyr|Ser|Val|Thr|Ala|Asn|Ser|Lys|Leu|Val|Ile|Ile|Thr|Ala|
| | | | |85| | | | |90| | | | |95| |

Lys Asp Tyr Ser Val Thr Ala Asn Ser Lys Leu Val Ile Ile Thr Ala
                85                  90                  95

Gly Ala Arg Gln Gln Glu Gly Glu Ser Arg Leu Asn Leu Val Gln Arg
            100                 105                 110

Asn Val Asn Ile Phe Lys Phe Ile Ile Pro Asn Val Val Lys Tyr Ser
        115                 120                 125

Pro Gln Cys Lys Leu Leu Ile Val Ser Asn Pro Val Asp Ile Leu Thr
    130                 135                 140

Tyr Val Ala Trp Lys Ile Ser Gly Phe Pro Lys Asn Arg Val Ile Gly
145                 150                 155                 160

Ser Gly Cys Asn Leu Asp Ser Ala Arg Phe Arg Tyr Leu Met Gly Glu
                165                 170                 175

Arg Leu Gly Val His Pro Leu Ser Cys His Gly Trp Val Leu Gly Glu
            180                 185                 190

His Gly Asp Ser Ser Val Pro Val Trp Ser Gly Val Asn Val Ala Gly
        195                 200                 205

Val Ser Leu Lys Ser Leu Asn Pro Gln Leu Gly Thr Asp Ala Asp Lys
    210                 215                 220

Glu Gln Trp Lys Asp Val His Lys Gln Val Val Asp Ser Ala Tyr Glu
225                 230                 235                 240

Val Ile Lys Leu Lys Gly Tyr Thr Ser Trp Ala Ile Gly Leu Ser Val
                245                 250                 255

Ala Asp Leu Ala Glu Ser Ile Met Lys Asn Leu Arg Arg Val His Pro
            260                 265                 270

Ile Ser Thr Met Ile Lys Gly Leu Tyr Gly Ile Lys Glu Asp Val Phe
        275                 280                 285

Leu Ser Val Pro Cys Ile Leu Gly Gln Asn Gly Ile Ser Asp Val Val
    290                 295                 300

Lys Val Thr Leu Thr Pro Asp Glu Glu Ala Arg Leu Lys Lys Ser Ala
305                 310                 315                 320

Asp Thr Leu Trp Gly Ile Gln Lys Glu Leu Gln Phe
                325                 330

```
<210> SEQ ID NO 40
<211> LENGTH: 1140
<212> TYPE: DNA
<213> ORGANISM: Ornithorhynchus anatinus

<400> SEQUENCE: 40
ttccaagatg gccggcgtca aggaacagct gatccagaat cttctcaaag aggagtacgc      60
ccctcaaaat aagatcaccg tggttggagt tggtgctgtg ggcatggcct gtgccatcag     120
catcttgatg aaggatttgg ctgatagagc cgcccttgtt gatgtcattg aggataagct     180
gaagggagaa atgatggatc ttcagcatgg cagccttttc ctcaggactc caaagatcgt     240
ctctggcaaa gactacagcg tgactgccaa ctccaagctg gttatcatca ccgccgggc      300 ccgtcagcag gagggagaga ccgtctgaa tctggtccag cgcaatgtca acatctttaa     360
attcatcatt cccaacgttg tcaagtacag ccccaactgc aagctgcttg tggtgtccaa     420
tccagtggat attttgacct acgtggcctg gaagatcagt ggcttcccca gaaccgagt      480 tatcggaagc ggctgcaatc tggattctgc ccgcttccgc tatctgatgg gagagaggct     540
gggcatccac tccacaagct gtcacggctg gtcatcgga gaacacggag actctagtgt      600
tcccgtgtgg agcggggtga acgttgccgg tgtctctctg aagaacctgc accccgattt     660
```

```
gggaactgat gcagacaagg agcagtggaa ggatgttcat aagcaggtgg ttgacagtgc      720
ctacgaggtc atcaaactga agggctacac ctcctgggcc atcggcctct cggtagccga      780
tctggcagaa agcatcgtga agaatcttag gcgggtgcac cccatttcca ccatgattaa      840
gggcctgtac gggatcaaag atgaagtctt cctcagcgtc ccctgtgtct tgggccagaa      900
cggcatctcg gacgtggtga agataaccct gaagtccgag gaggaggctc atctgaagaa      960
gagcgcagac accctgtggg gaattcagaa ggaactgcag ttttaaggct tttcaacatc     1020
ctagctgtct actgggtaac ggtagttagg ggattgggta tcccccactt ttgaagtagg     1080
ttagctgtct actgggtaac ggtagttagg ggattgggta tcccccactt ttgaagtagg     1140
```

<210> SEQ ID NO 41
<211> LENGTH: 1527
<212> TYPE: DNA
<213> ORGANISM: Tursiops truncatus

<400> SEQUENCE: 41

```
acgtgtactc ccgattcctt tcggttctaa gtccaatatg gcaactgtca aggatcagct       60
gattcagaat cttcttaagg aagaacatgt cccccagaat aagattacag tggttggtgt      120
tggtgctgtt ggcatggcct gtgccatcag tatcttaatg aaggacttgg cagatgaact      180
tgctcttgtt gatgtcatag aagacaaact gaagggagag atgatggatc tccaacatgg      240
cagccttttc cttagaacac caaaaatcgt ctctggcaaa gactatagtg tgacagcaaa      300
ctccaagctg gttattatca cagctggggc acgtcagcaa gagggagaaa gccgtcttaa      360
tttggtccaa cgtaatgtga acatctttaa attcatcgtt cctaatattg taaaatacag      420
cccacactgc aagttgcttg ttgtttccaa tccagtggat atcttgacct atgtggcttg      480
gaagataagc ggctttccca aaaccgtgt tattggaagt ggttgcaatt tggattcagc      540
ccggttccgt tacctcatgg gggaaaggct gggagttcac ccattaagct gtcatggatg      600
gatccttggg gagcatggag actctagtgt gcctgtatgg agtggagtga atgttgctgg      660
tgtctccctg aagaatctgc accccgaatt aggcactgat gccgataagg aacattggaa      720
agcaattcac aaacaggtgg ttgacagtgc ttatgaggtg atcaaactga aaggctacac      780
atcctgggcc gttggactat ctgtggcaga tttggcagaa agtataatga agaatcttag      840
gcgggtgcat ccgatttcca ccatgattaa gggtttgtat ggaataaaag aggatgtctt      900
ccttagtgtt ccttgcatct tgggacagaa tggaatctca gatgttgtga aagtgactct      960
gactcctgag gaacaggcct gtttgaagaa gagtgcagat acactttggg ggatccagaa     1020
agagctgcag ttttaaagtc taatatcata ccacttcact gtctaggcta aataggatt     1080 ttagttggag gttgtgcata ttgtccttta tatctgatct gtgactaaag cagtaatgtt     1140
aagacagcct aggaaaaaca tcaatttcct aacattagca ataggaatgg ttcataaaac     1200
cctgcagctg tatcctgatg ctgcatggca cttatcttgt gttgtcctaa attggttcgt     1260
gtaaaatagt tctacttcct caagaggtac cactgacagt gttgcagatg ctgcagttgc     1320
ccttcaaacc agatgtgtat ttaactctgt gttatataac ttctggttcc tttagccaag     1380
atgcctagtc caacttttt ctctccaatt aatcacattc tgggattgat tataaatcca     1440
gtattgcatg tcttgtgcat aactgttcta aagaatctta tttatgtac tatatgtatc     1500 agaatagtat acattgccat gtaatgt                                          1527
```

<210> SEQ ID NO 42
<211> LENGTH: 1609

<212> TYPE: DNA
<213> ORGANISM: Rattus norvegicus

<400> SEQUENCE: 42

```
gtgtgctgga gccactgtcg ccgatctcgc gcacgctact gctgctgctc gcccgtcgtc      60
ccccatcgtg cactaagcgg tcccaaaaga ttcaaagtcc aagatggcag ccctcaagga     120
ccagctgatt gtgaatcttc ttaaggaaga acaggtcccc cagaacaaga ttacagttgt     180
tggggttggt gctgttggca tggcttgtgc catcagtatc ttaatgaagg acttggctga     240
tgagcttgcc cttgttgatg tcatagaaga taagctaaag ggagagatga tggatcttca     300
gcatggcagc cttttcctta agacaccaaa aattgtctcc agcaaagatt atagtgtgac     360
tgcaaactcc aagctggtca ttatcaccgc gggggcccgt cagcaagagg gagagagccg     420
gctcaatttg gtccagcgaa acgtgaacat cttcaagttc atcattccaa atgttgtgaa     480
atacagtcca cagtgcaaac tgctcatcgt ctcaaaccca gtggatatct tgacctacgt     540
ggcttggaag atcagcggct cccccaaaaa cagagttatt ggaagtggtt gcaatctgga     600
ttcggctcgg ttccgttacc tgatgggaga aaggctggga gttcatccac tgagctgtca     660
cgggtgggtc ctgggagagc atggcgactc cagtgtgcct gtgtggagtg gtgtgaacgt     720
cgccggcgtc tccctgaagt ctctgaaccc gcagctgggc acggatgcag acaaggagca     780
gtggaaggat gtgcacaagc aggtggttga cagtgcatac gaagtgatca agctgaaagg     840
ttacacatcc tgggccattg gcctctccgt ggcagacttg gccgagagca taatgaagaa     900
ccttaggcgg gtgcatccca tttccaccat gattaagggt ctctatggaa tcaaggagga     960
tgtcttcctc agcgtcccat gtatcctggg acaaaatgga atctcagatg ttgtgaaggt    1020
gacactgact cctgacgagg aggcccgcct gaagaagagt gcagataccc tctggggaat    1080
ccagaaggag ctgcagttct aaagtcttcc cagtgtccta gcacttcact gtccaggctg    1140
cagcagggtt tctatggaga ccacgcactt ctcatctgag ctgtggttag tccagttggt    1200
ccagttgtgt tgaggtggtc tgggggaaat ctcagttcca cagctctacc ctgctaagtg    1260
gtacttgtgt agtggtaacc tggttagtgt gacaatccca ctgtctccaa gacacactgc    1320
caactgcatg caggctttga ttaccctgtg agcctgctgc attgctgtgc tacgcaccct    1380
caccaaacat gcctaggcca tgagttccca gttagttata agctggctcc agtgtgtaag    1440
tccatcgtgt atatcttgtg cataaatgtt ctacaggata ttttctgtat tatatgtgtc    1500
tgtagtgtac attgcaatat tacgtgaaat gtaagatctg catatggatg atggaaccaa    1560
ccactcaagt gtcatgccaa ggaaaacacc aaataaacct tgaacagtg              1609
```

<210> SEQ ID NO 43
<211> LENGTH: 289
<212> TYPE: DNA
<213> ORGANISM: Artificial Sequence
<220> FEATURE:
<223> OTHER INFORMATION: Synthetic CYC promoter

<400> SEQUENCE: 43

```
atttggcgag cgttggttgg tggatcaagc ccacgcgtag gcaatcctcg agcagatccg      60
ccaggcgtgt atatatagcg tggatggcca ggcaacttta tgctgacaca atacaggcat     120
atatatatgt gtgcgacgac acatgatcat atggcatgca tgtgctctgt atgtatataa     180
aactcttgtt ttcttctttt ctctaaatat tctttcctta tacattagga cctttgcagc     240
ataaattact atacttctat agacacgcaa acacaaatac acacactaa                289
```

```
<210> SEQ ID NO 44
<211> LENGTH: 655
<212> TYPE: DNA
<213> ORGANISM: Artificial Sequence
<220> FEATURE:
<223> OTHER INFORMATION: Synthetic GPD promoter

<400> SEQUENCE: 44
agtttatcat tatcaatact cgccatttca agaatacgt  aaataattaa tagtagtgat      60
tttcctaact ttatttagtc aaaaaattag ccttttaatt ctgctgtaac ccgtacatgc     120
ccaaaatagg gggcgggtta cacagaatat ataacatcgt aggtgtctgg gtgaacagtt     180
tattcctggc atccactaaa tataatggag cccgcttttt aagctggcat ccagaaaaaa     240
aaagaatccc agcaccaaaa tattgttttc ttcaccaacc atcagttcat aggtccattc     300
tcttagcgca actacagaga acaggggcac aaacaggcaa aaacgggca  caacctcaat     360 ggagtgatgc aacctgcctg gagtaaatga tgacacaagg caattgaccc acgcatgtat     420
ctatctcatt ttcttacacc ttctattacc ttctgctctc tctgatttgg aaaaagctga     480 aaaaaaggt  tgaaaccagt tccctgaaat tattccccta cttgactaat aagtatataa     540
agacggtagg tattgattgt aattctgtaa atctatttct taaacttctt aaattctact     600
tttatagtta gtcttttttt tagttttaaa acaccagaac ttagtttcga cggat         655

<210> SEQ ID NO 45
<211> LENGTH: 1468
<212> TYPE: DNA
<213> ORGANISM: Artificial Sequence
<220> FEATURE:
<223> OTHER INFORMATION: Synthetic ADH promoter

<400> SEQUENCE: 45
gccgggatcg aagaaatgat ggtaaatgaa ataggaaatc aaggagcatg aaggcaaaag      60
acaaatataa gggtcgaacg aaaaataaag tgaaaagtgt tgatatgatg tatttggctt     120
tgcggcgccg aaaaaacgag tttacgcaat tgcacaatca tgctgactct gtggcggacc     180
cgcgctcttg ccggcccggc gataacgctg ggcgtgaggc tgtgcccggc ggagttttt     240 gcgcctgcat tttccaaggt ttaccctgcg ctaaggggcg agattggaga agcaataaga     300
atgccggttg gggttgcgat gatgacgacc acgacaactg tgtcattat  ttaagttgcc     360 gaaagaacct gagtgcattt gcaacatgag tatactagaa gaatgagcca agacttgcga     420
gacgcgagtt tgccggtggt gcgaacaata gagcgaccat gaccttgaag gtgagacgcg     480
cataaccgct agagtacttt gaagaggaaa cagcaatagg gttgctacca gtataaatag     540
acaggtacat acaacactgg aaatggttgt ctgtttgagt acgctttcaa ttcatttggg     600
tgtgcacttt attatgttac aatatggaag ggaactttac acttctccta tgcacatata     660
ttaattaaag tccaatgcta gtagagaagg ggggtaacac ccctccgcgc tcttttccga     720
tttttttcta aaccgtggaa tatttcggat atccttttgt tgtttccggg tgtacaatat     780
ggacttcctc ttttctggca accaaaccca tacatcggga ttcctataat accttcgttg     840
gtctccctaa catgtaggtg gcggagggga gatatacaat agaacagata ccagacaaga     900
cataatgggc taaacaagac tacaccaatt acactgcctc attgatggtg gtacataacg     960
aactaatact gtagccctag acttgatagc catcatcata tcgaagtttc actacccttt    1020
ttccatttgc catctattga agtaataata ggcgcatgca acttcttttc ttttttttc    1080 ttttctctct ccccgttgt  tgtctcacca tatccgcaat gacaaaaaaa tgatggaaga    1140
```

-continued

```
cactaaagga aaaaattaac gacaaagaca gcaccaacag atgtcgttgt tccagagctg      1200 atgagggta tctcgaagca cacgaaactt tttccttcct tcattcacgc acactactct       1260
ctaatgagca acggtatacg gccttccttc cagttacttg aatttgaaat aaaaaaaagt      1320
ttgctgtctt gctatcaagt ataaatagac ctgcaattat taatcttttg tttcctcgtc      1380
attgttctcg ttccctttct tccttgtttc ttttctgca caatatttca agctatacca       1440
agcatacaat caactccaag ctggccgc                                        1468

<210> SEQ ID NO 46
<211> LENGTH: 252
<212> TYPE: DNA
<213> ORGANISM: Artificial Sequence
<220> FEATURE:
<223> OTHER INFORMATION: Synthetic CYC1 terminator

<400> SEQUENCE: 46
tcatgtaatt agttatgtca cgcttacatt cacgccctcc cccacatcc gctctaaccg        60 aaaaggaagg agttagacaa cctgaagtct aggtccctat ttatttttt atagttatgt      120 tagtattaag aacgttattt atatttcaaa ttttctttt ttttctgtac agacgcgtgt       180
acgcatgtaa cattatactg aaaaccttgc ttgagaaggt tttgggacgc tcgaaggctt     240
taatttgcgg cc                                                        252

<210> SEQ ID NO 47
<211> LENGTH: 563
<212> TYPE: PRT
<213> ORGANISM: Saccharomyces cerevisiae

<400> SEQUENCE: 47

Met Ser Glu Ile Thr Leu Gly Lys Tyr Leu Phe Glu Arg Leu Lys Gln
  1               5                  10                  15

Val Asn Val Asn Thr Val Phe Gly Leu Pro Gly Asp Phe Asn Leu Ser
                 20                  25                  30

Leu Leu Asp Lys Ile Tyr Glu Val Glu Gly Met Arg Trp Ala Gly Asn
             35                  40                  45

Ala Asn Glu Leu Asn Ala Ala Tyr Ala Ala Asp Gly Tyr Ala Arg Ile
         50                  55                  60

Lys Gly Met Ser Cys Ile Ile Thr Thr Phe Gly Val Gly Glu Leu Ser
 65                  70                  75                  80

Ala Leu Asn Gly Ile Ala Gly Ser Tyr Ala Glu His Val Gly Val Leu
                 85                  90                  95

His Val Val Gly Val Pro Ser Ile Ser Ala Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ala Met Ile Thr Asp Ile Ala Thr
    130                 135                 140

Ala Pro Ala Glu Ile Asp Arg Cys Ile Arg Thr Thr Tyr Val Thr Gln
145                 150                 155                 160

Arg Pro Val Tyr Leu Gly Leu Pro Ala Asn Leu Val Asp Leu Asn Val
                165                 170                 175

Pro Ala Lys Leu Leu Gln Thr Pro Ile Asp Met Ser Leu Lys Pro Asn
            180                 185                 190

Asp Ala Glu Ser Glu Lys Glu Val Ile Asp Thr Ile Leu Ala Leu Val
        195                 200                 205
```

-continued

Lys Asp Ala Lys Asn Pro Val Ile Leu Ala Asp Ala Cys Cys Ser Arg
210                 215                 220

His Asp Val Lys Ala Glu Thr Lys Lys Leu Ile Asp Leu Thr Gln Phe
225                 230                 235                 240

Pro Ala Phe Val Thr Pro Met Gly Lys Gly Ser Ile Asp Glu Gln His
                245                 250                 255

Pro Arg Tyr Gly Gly Val Tyr Val Gly Thr Leu Ser Lys Pro Glu Val
                260                 265                 270

Lys Glu Ala Val Glu Ser Ala Asp Leu Ile Leu Ser Val Gly Ala Leu
275                 280                 285

Leu Ser Asp Phe Asn Thr Gly Ser Phe Ser Tyr Ser Tyr Lys Thr Lys
290                 295                 300

Asn Ile Val Glu Phe His Ser Asp His Met Lys Ile Arg Asn Ala Thr
305                 310                 315                 320

Phe Pro Gly Val Gln Met Lys Phe Val Leu Gln Lys Leu Leu Thr Thr
                325                 330                 335

Ile Ala Asp Ala Ala Lys Gly Tyr Lys Pro Val Ala Val Pro Ala Arg
                340                 345                 350

Thr Pro Ala Asn Ala Ala Val Pro Ala Ser Thr Pro Leu Lys Gln Glu
                355                 360                 365

Trp Met Trp Asn Gln Leu Gly Asn Phe Leu Gln Glu Gly Asp Val Val
370                 375                 380

Ile Ala Glu Thr Gly Thr Ser Ala Phe Gly Ile Asn Gln Thr Thr Phe
385                 390                 395                 400

Pro Asn Asn Thr Tyr Gly Ile Ser Gln Val Leu Trp Gly Ser Ile Gly
                405                 410                 415

Phe Thr Thr Gly Ala Thr Leu Gly Ala Ala Phe Ala Ala Glu Glu Ile
                420                 425                 430

Asp Pro Lys Lys Arg Val Ile Leu Phe Ile Gly Asp Gly Ser Leu Gln
                435                 440                 445

Leu Thr Val Gln Glu Ile Ser Thr Met Ile Arg Trp Gly Leu Lys Pro
450                 455                 460

Tyr Leu Phe Val Leu Asn Asn Asp Gly Tyr Thr Ile Glu Lys Leu Ile
465                 470                 475                 480

His Gly Pro Lys Ala Gln Tyr Asn Glu Ile Gln Gly Trp Asp His Leu
                485                 490                 495

Ser Leu Leu Pro Thr Phe Gly Ala Lys Asp Tyr Glu Thr His Arg Val
                500                 505                 510

Ala Thr Thr Gly Glu Trp Asp Lys Leu Thr Gln Asp Lys Ser Phe Asn
                515                 520                 525

Asp Asn Ser Lys Ile Arg Met Ile Glu Ile Met Leu Pro Val Phe Asp
530                 535                 540

Ala Pro Gln Asn Leu Val Glu Gln Ala Lys Leu Thr Ala Ala Thr Asn
545                 550                 555                 560

Ala Lys Gln

<210> SEQ ID NO 48
<211> LENGTH: 1692
<212> TYPE: DNA
<213> ORGANISM: Saccharomyces cerevisiae

<400> SEQUENCE: 48
atgtctgaaa ttactttggg taaatatttg ttcgaaagat taagcaagt caacgttaac    60

```
accgttttcg gtttgccagg tgacttcaac ttgtccttgt tggacaagat ctacgaagtt    120
gaaggtatga gatgggctgg taacgccaac gaattgaacg ctgcttacgc cgctgatggt    180
tacgctcgta tcaagggtat gtcttgtatc atcaccacct tcggtgtcgg tgaattgtct    240
gctttgaacg gtattgccgg ttcttacgct gaacacgtcg gtgttttgca cgttgttggt    300
gtcccatcca tctctgctca agctaagcaa ttgttgttgc accacacctt gggtaacggt    360
gacttcactg ttttccacag aatgtctgcc aacatttctg aaaccactgc tatgatcact    420
gacattgcta ccgccccagc tgaaattgac agatgtatca gaaccactta cgtcacccaa    480
agaccagtct acttaggttt gccagctaac ttggtcgact gaacgtccc agctaagttg    540 ttgcaaactc caattgacat gtctttgaag ccaaacgatg ctgaatccga aaaggaagtc    600
attgacacca tcttggcttt ggtcaaggat gctaagaacc cagttatctt ggctgatgct    660
tgttgttcca gacacgacgt caaggctgaa actaagaagt tgattgactt gactcaattc    720
ccagctttcg tcaccccaat gggtaagggt tccattgacg aacaacaccc aagatacggt    780
ggtgtttacg tcggtacctt gtccaagcca gaagttaagg aagccgttga atctgctgac    840
ttgattttgt ctgtcggtgc tttgttgtct gatttcaaca ccggttcttt ctcttactct    900
tacaagacca agaacattgt cgaattccac tccgaccaca tgaagatcag aaacgccact    960
ttcccaggtg tccaaatgaa attcgttttg caaaagttgt tgaccactat tgctgacgcc   1020
gctaagggtt acaagccagt tgctgtccca gctagaactc cagctaacgc tgctgtccca   1080
gcttctaccc cattgaagca agaatggatg tggaaccaat tgggtaactt cttgcaagaa   1140
ggtgatgttg tcattgctga aaccggtacc tccgctttcg gtatcaacca aaccactttc   1200
ccaaacaaca cctacggtat ctctcaagtc ttatgggggtt ccattggttt caccactggt   1260
gctaccttgg gtgctgcttt cgctgctgaa gaaattgatc aaagaagag agttatctta   1320 ttcattggtg acggttcttt gcaattgact gttcaagaaa tctccaccat gatcagatgg   1380
ggcttgaagc atacttgtt cgtcttgaac aacgatggtt acaccattga aaagttgatt   1440
cacggtccaa aggctcaata caacgaaatt caaggttggg accacctatc cttgttgcca   1500
actttcggtg ctaaggacta tgaaacccac agagtcgcta ccaccggtga atgggacaag   1560
ttgacccaag acaagtcttt caacgacaac tctaagatca gaatgattga aatcatgttg   1620
ccagtcttcg atgctccaca aaacttggtt gaacaagcta agttgactgc tgctaccaac   1680
gctaagcaat aa                                                       1692
```

<210> SEQ ID NO 49
<211> LENGTH: 591
<212> TYPE: PRT
<213> ORGANISM: Saccharomyces cerevisiae

<400> SEQUENCE: 49

```
Met Leu Lys Tyr Lys Pro Leu Leu Lys Ile Ser Lys Asn Cys Glu Ala
1               5                   10                  15

Ala Ile Leu Arg Ala Ser Lys Thr Arg Leu Asn Thr Ile Arg Ala Tyr
            20                  25                  30

Gly Ser Thr Val Pro Lys Ser Lys Ser Phe Glu Gln Asp Ser Arg Lys
        35                  40                  45

Arg Thr Gln Ser Trp Thr Ala Leu Arg Val Gly Ala Ile Leu Ala Ala
    50                  55                  60

Thr Ser Ser Val Ala Tyr Leu Asn Trp His Asn Gly Gln Ile Asp Asn
65                  70                  75                  80
```

```
Glu Pro Lys Leu Asp Met Asn Lys Gln Lys Ile Ser Pro Ala Glu Val
                 85                  90                  95

Ala Lys His Asn Lys Pro Asp Asp Cys Trp Val Val Ile Asn Gly Tyr
            100                 105                 110

Val Tyr Asp Leu Thr Arg Phe Leu Pro Asn His Pro Gly Gly Gln Asp
        115                 120                 125

Val Ile Lys Phe Asn Ala Gly Lys Asp Val Thr Ala Ile Phe Glu Pro
    130                 135                 140

Leu His Ala Pro Asn Val Ile Asp Lys Tyr Ile Ala Pro Glu Lys Lys
145                 150                 155                 160

Leu Gly Pro Leu Gln Gly Ser Met Pro Pro Glu Leu Val Cys Pro Pro
                165                 170                 175

Tyr Ala Pro Gly Glu Thr Lys Glu Asp Ile Ala Arg Lys Glu Gln Leu
            180                 185                 190

Lys Ser Leu Leu Pro Pro Leu Asp Asn Ile Ile Asn Leu Tyr Asp Phe
        195                 200                 205

Glu Tyr Leu Ala Ser Gln Thr Leu Thr Lys Gln Ala Trp Ala Tyr Tyr
    210                 215                 220

Ser Ser Gly Ala Asn Asp Glu Val Thr His Arg Glu Asn His Asn Ala
225                 230                 235                 240

Tyr His Arg Ile Phe Phe Lys Pro Lys Ile Leu Val Asp Val Arg Lys
                245                 250                 255

Val Asp Ile Ser Thr Asp Met Leu Gly Ser His Val Asp Val Pro Phe
            260                 265                 270

Tyr Val Ser Ala Thr Ala Leu Cys Lys Leu Gly Asn Pro Leu Glu Gly
        275                 280                 285

Glu Lys Asp Val Ala Arg Gly Cys Gly Gln Gly Val Thr Lys Val Pro
    290                 295                 300

Gln Met Ile Ser Thr Leu Ala Ser Cys Ser Pro Glu Glu Ile Ile Glu
305                 310                 315                 320

Ala Ala Pro Ser Asp Lys Gln Ile Gln Trp Tyr Gln Leu Tyr Val Asn
                325                 330                 335

Ser Asp Arg Lys Ile Thr Asp Asp Leu Val Lys Asn Val Glu Lys Leu
            340                 345                 350

Gly Val Lys Ala Leu Phe Val Thr Val Asp Ala Pro Ser Leu Gly Gln
        355                 360                 365

Arg Glu Lys Asp Met Lys Leu Lys Phe Ser Asn Thr Lys Ala Gly Pro
    370                 375                 380

Lys Ala Met Lys Lys Thr Asn Val Glu Glu Ser Gln Gly Ala Ser Arg
385                 390                 395                 400

Ala Leu Ser Lys Phe Ile Asp Pro Ser Leu Thr Trp Lys Asp Ile Glu
                405                 410                 415

Glu Leu Lys Lys Lys Thr Lys Leu Pro Ile Val Ile Lys Gly Val Gln
            420                 425                 430

Arg Thr Glu Asp Val Ile Lys Ala Ala Glu Ile Gly Val Ser Gly Val
        435                 440                 445

Val Leu Ser Asn His Gly Gly Arg Gln Leu Asp Phe Ser Arg Ala Pro
    450                 455                 460

Ile Glu Val Leu Ala Glu Thr Met Pro Ile Leu Glu Gln Arg Asn Leu
465                 470                 475                 480

Lys Asp Lys Leu Glu Val Phe Val Asp Gly Gly Val Arg Arg Gly Thr
                485                 490                 495

Asp Val Leu Lys Ala Leu Cys Leu Gly Ala Lys Gly Val Gly Leu Gly
```

```
            500                 505                 510
Arg Pro Phe Leu Tyr Ala Asn Ser Cys Tyr Gly Arg Asn Gly Val Glu
        515                 520                 525

Lys Ala Ile Glu Ile Leu Arg Asp Glu Ile Glu Met Ser Met Arg Leu
        530                 535                 540

Leu Gly Val Thr Ser Ile Ala Glu Leu Lys Pro Asp Leu Leu Asp Leu
545                 550                 555                 560

Ser Thr Leu Lys Ala Arg Thr Val Gly Val Pro Asn Asp Val Leu Tyr
                565                 570                 575

Asn Glu Val Tyr Glu Gly Pro Thr Leu Thr Glu Phe Glu Asp Ala
                580                 585                 590

<210> SEQ ID NO 50
<211> LENGTH: 1776
<212> TYPE: DNA
<213> ORGANISM: Saccharomyces cerevisiae

<400> SEQUENCE: 50
atgctaaaat caaacctttt actaaaaatc tcgaagaact gtgaggctgc tatcctcaga    60
gcgtctaaga ctagattgaa cacaatccgc gcgtacggtt ctaccgttcc aaaatccaag   120
tcgttcgaac aagactcaag aaaacgcaca cagtcatgga ctgccttgag agtcggtgca   180
attctagccg ctactagttc cgtggcgtat ctaaactggc ataatggcca aatagacaac   240
gagccgaaac tggatatgaa taaacaaaag atttcgcccg ctgaagttgc caagcataac   300
aagcccgatg attgttgggt tgtgatcaat ggttacgtat acgacttaac gcgattccta   360
ccaaatcatc caggtgggca ggatgttatc aagtttaacg ccgggaaaga tgtcactgct   420 attttttgaac cactacatgc tcctaatgtc atcgataagt atatagctcc cgagaaaaaa   480
ttgggtcccc ttcaaggatc catgcctcct gaacttgtct gtcctcctta tgctcctggt   540
gaaactaagg aagatatcgc tagaaaagaa caactaaaat cgctgctacc tcctctagat   600
aatattatta acctttacga ctttgaatac ttggcctctc aaactttgac taaacaagcg   660
tgggcctact attcctccgg tgctaacgac gaagttactc acagagaaaa ccataatgct   720
tatcatagga tttttttcaa accaaagatc cttgtagatg tacgcaaagt agacatttca   780
actgacatgt tgggttctca tgtggatgtt cccttctacg tgtctgctac agctttgtgt   840
aaactgggaa accccttaga aggtgaaaaa gatgtcgcca gaggttgtgg ccaaggtgtg   900
acaaaagtcc cacaaatgat atctactttg gcttcatgtt ccctgaagga aattattgaa   960
gcagcaccct ctgataaaca aattcaatgg taccaactat atgttaactc tgatagaaag  1020
atcactgatg atttggttaa aaatgtagaa aagctgggtg taaaggcatt atttgtcact  1080
gtggatgctc caagtttagg tcaaagagaa aaagatatga agctgaaatt ttccaataca  1140
aaggctggtc caaaagcgat gaagaaaact aatgtagaag aatctcaagg tgcttcgaga  1200
gcgttatcaa agtttattga cccctctttg acttggaaag atatagaaga gttgaagaaa  1260
aagacaaaac tacctattgt tatcaaaggt gttcaacgta ccgaagatgt tatcaaagca  1320
gcagaaatcg gtgtaagtgg ggtggttcta tccaatcatg gtggtagaca attagatttt  1380
tcaagggctc ccattgaagt cctggctgaa accatgccaa tcctggaaca acgtaacttg  1440
aaggataagt tggaagtttt cgtggacggt ggtgttcgtc gtggtacaga tgtcttgaaa  1500
gcgttatgtc taggtgctaa aggtgttggt ttgggtagac cattcttgta tgcgaactca  1560
tgctatggtc gtaatggtgt tgaaaaagcc attgaaattt taagagatga aattgaaatg  1620
```
tctatgagac tattaggtgt tactagcatt gcggaattga agcctgatct tttagatcta    1680
tcaacactaa aggcaagaac agttggagta ccaaacgacg tgctgtataa tgaagtttat    1740
gagggaccta ctttaacaga atttgaggat gcatga                              1776

<210> SEQ ID NO 51
<211> LENGTH: 391
<212> TYPE: PRT
<213> ORGANISM: Saccharomyces cerevisiae

<400> SEQUENCE: 51

Met Ser Ala Ala Ala Asp Arg Leu Asn Leu Thr Ser Gly His Leu Asn
1               5                   10                  15

Ala Gly Arg Lys Arg Ser Ser Ser Val Ser Leu Lys Ala Ala Glu
            20                  25                  30

Lys Pro Phe Lys Val Thr Val Ile Gly Ser Gly Asn Trp Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Phe Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

```
Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380

Glu Leu Asp Leu His Glu Asp
385                 390
```

<210> SEQ ID NO 52
<211> LENGTH: 1176
<212> TYPE: DNA
<213> ORGANISM: Saccharomyces cerevisiae

<400> SEQUENCE: 52

| | | | | |
|---|---|---|---|---|
| atgtctgctg | ctgctgatag | attaaactta | acttccggcc | acttgaatgc | tggtagaaag | 60 |
| agaagttcct | cttctgtttc | tttgaaggct | gccgaaaagc | ctttcaaggt | tactgtgatt | 120 |
| ggatctggta | actggggtac | tactattgcc | aaggtggttg | ccgaaaattg | taagggatac | 180 |
| ccagaagttt | tcgctccaat | agtacaaatg | tgggtgttcg | aagaagagat | caatggtgaa | 240 |
| aaattgactg | aaatcataaa | tactagacat | caaaacgtga | atacttgcc  | tggcatcact | 300 |
| ctacccgaca | atttggttgc | taatccagac | ttgattgatt | cagtcaagga | tgtcgacatc | 360 |
| atcgttttca | acattccaca | tcaattttg  | ccccgtatct | gtagccaatt | gaaaggtcat | 420 |
| gttgattcac | acgtcagagc | tatctcctgt | ctaaagggtt | tgaagttgg  | tgctaaaggt | 480 |
| gtccaattgc | tatcctctta | catcactgag | gaactaggta | ttcaatgtgg | tgctctatct | 540 |
| ggtgctaaca | ttgccaccga | agtcgctcaa | gaacactggt | ctgaaacaac | agttgcttac | 600 |
| cacattccaa | aggattcag  | aggcgagggc | aaggacgtcg | accataaggt | tctaaaggcc | 660 |
| ttgttccaca | gaccttactt | ccacgttagt | gtcatcgaag | atgttgctgg | tatctccatc | 720 |
| tgtggtgctt | tgaagaacgt | tgttgcctta | ggttgtggtt | tcgtcgaagg | tctaggctgg | 780 |
| ggtaacaacg | cttctgctgc | catccaaaga | gtcggtttgg | gtgagatcat | cagattcggt | 840 |
| caaatgtttt | tcccagaatc | tagagaagaa | acatactacc | aagagtctgc | tggtgttgct | 900 |
| gatttgatca | ccacctgcgc | tggtggtaga | aacgtcaagg | ttgctaggct | aatggctact | 960 |
| tctggtaagg | acgcctggga | atgtgaaaag | gagttgttga | atggccaatc | cgctcaaggt | 1020 |
| ttaattacct | gcaaagaagt | tcacgaatgg | ttggaaacat | gtggctctgt | cgaagacttc | 1080 |
| ccattattg  | aagccgtata | ccaaatcgtt | tacaacaact | acccaatgaa | gaacctgccg | 1140 |
| gacatgattg | aagaattaga | tctacatgaa | gattag | | | 1176 |

<210> SEQ ID NO 53
<211> LENGTH: 1404
<212> TYPE: DNA
<213> ORGANISM: Escherichia coli

<400> SEQUENCE: 53

| | | | | | | |
|---|---|---|---|---|---|---|
| atgaatcaac | aggatattga | acaggtggtg | aaagcggtac | tgctgaaaat | gcaaagcagt | 60 |
| gacacgccgt | ccgccgccgt | tcatgagatg | ggcgttttcg | cgtccctgga | tgacgccgtt | 120 |
| gcggcagcca | aagtcgccca | gcaagggtta | aaaagcgtgg | caatgcgcca | gttagccatt | 180 |
| gctgccattc | gtgaagcagg | cgaaaaacac | gccagagatt | tagcggaact | tgccgtcagt | 240 |
| gaaaccggca | tggggcgcgt | tgaagataaa | tttgcaaaaa | acgtcgctca | ggcgcgcggc | 300 |
| acaccaggcg | ttgagtgcct | ctctccgcaa | gtgctgactg | cgacaacgg  | cctgacccta | 360 |
| attgaaaacg | caccctgggg | cgtggtggct | tcggtgacgc | cttccactaa | cccggcggca | 420 |

```
accgtaatta caacgccat cagcctgatt gccgcgggca acagcgtcat ttttgccccg      480
catccggcgg cgaaaaaagt ctcccagcgg gcgattacgc tgctcaacca ggcgattgtt      540
gccgcaggtg ggccggaaaa cttactggtt actgtggcaa atccggatat cgaaaccgcg      600
caacgcttgt tcaagtttcc gggtatcggc ctgctggtgg taaccggcgg cgaagcggta      660
gtagaagcgg cgcgtaaaca caccaataaa cgtctgattg ccgcaggcgc tggcaacccg      720
ccggtagtgt ggatgaaac cgccgacctc gcccgtgccg ctcagtccat cgtcaaaggc      780
gcttctttcg ataacaacat catttgtgcc gacgaaaagg tactgattgt tgttgatagc      840
gtagccgatg aactgatgcg tctgatggaa ggccagcacg cggtgaaact gaccgcagaa      900
caggcgcagc agctgcaacc ggtgttgctg aaaaatatcg acgagcgcgg aaaaggcacc      960
gtcagccgtg actgggttgg tcgcgacgca ggcaaaatcg cggcggcaat cggccttaaa     1020
gttccgcaag aaacgcgcct gctgtttgtg aaaccaccg cagaacatcc gtttgccgtg      1080
actgaactga tgatgccggt gttgcccgtc gtgcgcgtcg ccaacgtggc ggatgccatt     1140
gcgctagcgg tgaaactgga aggcggttgc caccacacgg cggcaatgca ctcgcgcaac     1200
atcgaaaaca tgaaccagat ggcgaatgct attgatacca gcattttcgt taagaacgga     1260
ccgtgcattg ccgggctggg gctgggcggg gaaggctgga ccaccatgac catcaccacg     1320
ccaaccggtg aagggtaac cagcgcgcgt acgtttgtcc gtctgcgtcg ctgtgtatta     1380
gtcgatgcgt ttcgcattgt ttaa                                           1404

<210> SEQ ID NO 54
<211> LENGTH: 467
<212> TYPE: PRT
<213> ORGANISM: Escherichia coli

<400> SEQUENCE: 54

Met Asn Gln Gln Asp Ile Glu Gln Val Val Lys Ala Val Leu Leu Lys
  1               5                  10                  15

Met Gln Ser Ser Asp Thr Pro Ser Ala Ala Val His Glu Met Gly Val
                 20                  25                  30

Phe Ala Ser Leu Asp Asp Ala Val Ala Ala Lys Val Ala Gln Gln
             35                  40                  45

Gly Leu Lys Ser Val Ala Met Arg Gln Leu Ala Ile Ala Ala Ile Arg
         50                  55                  60

Glu Ala Gly Glu Lys His Ala Arg Asp Leu Ala Glu Leu Ala Val Ser
 65                  70                  75                  80

Glu Thr Gly Met Gly Arg Val Glu Asp Lys Phe Ala Lys Asn Val Ala
                 85                  90                  95

Gln Ala Arg Gly Thr Pro Gly Val Glu Cys Leu Ser Pro Gln Val Leu
            100                 105                 110

Thr Gly Asp Asn Gly Leu Thr Leu Ile Glu Asn Ala Pro Trp Gly Val
        115                 120                 125

Val Ala Ser Val Thr Pro Ser Thr Asn Pro Ala Ala Thr Val Ile Asn
    130                 135                 140

Asn Ala Ile Ser Leu Ile Ala Ala Gly Asn Ser Val Ile Phe Ala Pro
145                 150                 155                 160

His Pro Ala Ala Lys Lys Val Ser Gln Arg Ala Ile Thr Leu Leu Asn
                165                 170                 175

Gln Ala Ile Val Ala Ala Gly Gly Pro Glu Asn Leu Leu Val Thr Val
            180                 185                 190
```

```
Ala Asn Pro Asp Ile Glu Thr Ala Gln Arg Leu Phe Lys Phe Pro Gly
        195                 200                 205

Ile Gly Leu Leu Val Val Thr Gly Gly Glu Ala Val Val Glu Ala Ala
    210                 215                 220

Arg Lys His Thr Asn Lys Arg Leu Ile Ala Ala Gly Ala Gly Asn Pro
225                 230                 235                 240

Pro Val Val Asp Glu Thr Ala Asp Leu Ala Arg Ala Ala Gln Ser
                245                 250                 255

Ile Val Lys Gly Ala Ser Phe Asp Asn Ile Ile Cys Ala Asp Glu
                260                 265                 270

Lys Val Leu Ile Val Val Asp Ser Val Ala Asp Glu Leu Met Arg Leu
            275                 280                 285

Met Glu Gly Gln His Ala Val Lys Leu Thr Ala Glu Gln Ala Gln Gln
        290                 295                 300

Leu Gln Pro Val Leu Leu Lys Asn Ile Asp Glu Arg Gly Lys Gly Thr
305                 310                 315                 320

Val Ser Arg Asp Trp Val Gly Arg Asp Ala Gly Lys Ile Ala Ala Ala
                325                 330                 335

Ile Gly Leu Lys Val Pro Gln Glu Thr Arg Leu Leu Phe Val Glu Thr
            340                 345                 350

Thr Ala Glu His Pro Phe Ala Val Thr Glu Leu Met Met Pro Val Leu
        355                 360                 365

Pro Val Val Arg Val Ala Asn Val Ala Asp Ala Ile Ala Leu Ala Val
    370                 375                 380

Lys Leu Glu Gly Gly Cys His His Thr Ala Ala Met His Ser Arg Asn
385                 390                 395                 400

Ile Glu Asn Met Asn Gln Met Ala Asn Ala Ile Asp Thr Ser Ile Phe
                405                 410                 415

Val Lys Asn Gly Pro Cys Ile Ala Gly Leu Gly Leu Gly Gly Glu Gly
            420                 425                 430

Trp Thr Thr Met Thr Ile Thr Thr Pro Thr Gly Glu Gly Val Thr Ser
        435                 440                 445

Ala Arg Thr Phe Val Arg Leu Arg Arg Cys Val Leu Val Asp Ala Phe
    450                 455                 460

Arg Ile Val
465

<210> SEQ ID NO 55
<211> LENGTH: 1047
<212> TYPE: DNA
<213> ORGANISM: Saccharomyces cerevisiae

<400> SEQUENCE: 55
atgtctatcc cagaaactca aaaaggtgtt atcttctacg aatcccacgg taagttggaa      60
tacaaagata ttccagttcc aaagccaaag gccaacgaat tgttgatcaa cgttaaatac     120
tctggtgtct gtcacactga cttgcacgct tggcacggtg actggccatt gccagttaag     180
ctaccattag ttggtggtca cgaaggtgcc ggtgtcgttg tcggcatggg tgaaaacgtt     240
aagggctgga gatcggtga ctacgccggt atcaaatggt tgaacggttc ttgtatggcc     300
tgtgaatact gtgaattggg taacgaatcc aactgtcctc acgctgactt gtctggttac     360
acccacgacg ttctttccca agaatacgct accgctgacg ctgttcaagc cgctcacatt     420
cctcaaggta ctgacttggc tgaagtcgcc ccagttttgt gtgctggtat caccgtctac     480
aaggctttga gtctgctaa cttgatggcc ggtcactggg ttgctatctc cggtgctgct     540
```

```
ggtggtctag gttctttggc tgttcaatac gccaaggcta tgggttacag agtcttgggt    600
attgacggtg gtgaaggtaa ggaagaatta ttcagatcca tcggtggtga agtcttcatt    660
gacttcacta aggaaaagga cattgtcggt gctgttctaa aggccactga cggtggtgct    720
cacggtgtca tcaacgtttc cgtttccgaa gccgctattg aagcttccac cagatacgtt    780
agagctaacg gtaccaccgt tttggtcggt atgccagctg gtgccaagtg ttgttctgat    840
gtcttcaacc aagtcgtcaa gtccatctct attgttggtt cttacgtcgg taacagagct    900
gacaccagag aagctttgga cttcttcgcc agaggtttga tcaagtctcc aatcaaggtt    960
gtcggcttgt ctaccttgcc agaaatttac gaaaagatgg aaaagggtca atcgttggt   1020 agatacgttg ttgacacttc taaataa                                      1047
```

<210> SEQ ID NO 56
<211> LENGTH: 348
<212> TYPE: PRT
<213> ORGANISM: Saccharomyces cerevisiae

<400> SEQUENCE: 56

```
Met Ser Ile Pro Glu Thr Gln Lys Gly Val Ile Phe Tyr Glu Ser His
 1               5                  10                  15

Gly Lys Leu Glu Tyr Lys Asp Ile Pro Val Pro Lys Pro Lys Ala Asn
             20                  25                  30

Glu Leu Leu Ile Asn Val Lys Tyr Ser Gly Val Cys His Thr Asp Leu
         35                  40                  45

His Ala Trp His Gly Asp Trp Pro Leu Pro Val Lys Leu Pro Leu Val
     50                  55                  60

Gly Gly His Glu Gly Ala Gly Val Val Val Gly Met Gly Glu Asn Val
 65                  70                  75                  80

Lys Gly Trp Lys Ile Gly Asp Tyr Ala Gly Ile Lys Trp Leu Asn Gly
                 85                  90                  95

Ser Cys Met Ala Cys Glu Tyr Cys Glu Leu Gly Asn Glu Ser Asn Cys
            100                 105                 110

Pro His Ala Asp Leu Ser Gly Tyr Thr His Asp Gly Ser Phe Gln Gln
        115                 120                 125

Tyr Ala Thr Ala Asp Ala Val Gln Ala Ala His Ile Pro Gln Gly Thr
    130                 135                 140

Asp Leu Ala Gln Val Ala Pro Ile Leu Cys Ala Gly Ile Thr Val Tyr
145                 150                 155                 160

Lys Ala Leu Lys Ser Ala Asn Leu Met Ala Gly His Trp Val Ala Ile
                165                 170                 175

Ser Gly Ala Ala Gly Gly Leu Gly Ser Leu Ala Val Gln Tyr Ala Lys
            180                 185                 190

Ala Met Gly Tyr Arg Val Leu Gly Ile Asp Gly Gly Glu Gly Lys Glu
        195                 200                 205

Glu Leu Phe Arg Ser Ile Gly Gly Glu Val Phe Ile Asp Phe Thr Lys
    210                 215                 220

Glu Lys Asp Ile Val Gly Ala Val Leu Lys Ala Thr Asp Gly Gly Ala
225                 230                 235                 240

His Gly Val Ile Asn Val Ser Val Ser Glu Ala Ala Ile Glu Ala Ser
                245                 250                 255

Thr Arg Tyr Val Arg Ala Asn Gly Thr Thr Val Leu Val Gly Met Pro
            260                 265                 270

Ala Gly Ala Lys Cys Cys Ser Asp Val Phe Asn Gln Val Val Lys Ser
```

```
              275                 280                 285
Ile Ser Ile Val Gly Ser Tyr Val Gly Asn Arg Ala Asp Thr Arg Glu
    290                 295                 300

Ala Leu Asp Phe Phe Ala Arg Gly Leu Val Lys Ser Pro Ile Lys Val
305                 310                 315                 320

Val Gly Leu Ser Thr Leu Pro Glu Ile Tyr Glu Lys Met Glu Lys Gly
                325                 330                 335

Gln Ile Val Gly Arg Tyr Val Val Asp Thr Ser Lys
            340                 345
```

<210> SEQ ID NO 57
<211> LENGTH: 753
<212> TYPE: DNA
<213> ORGANISM: Saccharomyces cerevisiae

<400> SEQUENCE: 57

```
atgcctttga ccacaaaacc tttatctttg aaaatcaacg ccgctctatt cgatgttgac      60
ggtaccatca tcatctctca accagccatt gctgctttct ggagagattt cggtaaagac     120
aagccttact cgatgccga acacgttatt cacatctctc acggttggag aacttacgat     180
gccattgcca agttcgctcc agactttgct gatgaagaat acgttaacaa gctagaaggt     240
gaaatcccag aaaagtacgg tgaacactcc atcgaagttc caggtgctgt caagttgtgt     300
aatgctttga cgccttgcc aaaggaaaaa tgggctgtcg ccacctctgg tacccgtgac     360
atggccaaga atggttcga cattttgaag atcaagagac cagaatactt catcaccgcc     420
aatgatgtca agcaaggtaa gcctcaccca gaaccatact aaagggtag aaacggtttg     480
ggtttcccaa ttaatgaaca agacccatcc aaatctaagg ttgttgtctt gaagacgca      540
ccagctggta ttgctgctgg taaggctgct ggctgtaaaa tcgttggtat tgctaccact     600
ttcgatttgg acttcttgaa ggaaaagggt tgtgacatca ttgtcaagaa ccacgaatct     660
atcagagtcg gtaatacaa cgctgaaacc gatgaagtcg aattgatctt tgatgactac     720
ttatacgcta aggatgactt gttgaaatgg taa                                  753
```

<210> SEQ ID NO 58
<211> LENGTH: 250
<212> TYPE: PRT
<213> ORGANISM: Saccharomyces cerevisiae

<400> SEQUENCE: 58

```
Met Pro Leu Thr Thr Lys Pro Leu Ser Leu Lys Ile Asn Ala Ala Leu
  1               5                  10                  15

Phe Asp Val Asp Gly Thr Ile Ile Ser Gln Pro Ala Ile Ala Ala
                 20                  25                  30

Phe Trp Arg Asp Phe Gly Lys Asp Lys Pro Tyr Phe Asp Ala Glu His
             35                  40                  45

Val Ile His Ile Ser His Gly Trp Arg Thr Tyr Asp Ala Ile Ala Lys
         50                  55                  60

Phe Ala Pro Asp Phe Ala Asp Glu Glu Tyr Val Asn Lys Leu Glu Gly
 65                  70                  75                  80

Glu Ile Pro Glu Lys Tyr Gly Glu His Ser Ile Glu Val Pro Gly Ala
                 85                  90                  95

Val Lys Leu Cys Asn Ala Leu Asn Ala Leu Pro Lys Glu Lys Trp Ala
            100                 105                 110

Val Ala Thr Ser Gly Thr Arg Asp Met Ala Lys Lys Trp Phe Asp Ile
        115                 120                 125
```

```
Leu Lys Ile Lys Arg Pro Glu Tyr Phe Ile Thr Ala Asn Asp Val Lys
    130                 135                 140

Gln Gly Lys Pro His Pro Glu Pro Tyr Leu Lys Gly Arg Asn Gly Leu
145                 150                 155                 160

Gly Phe Pro Ile Asn Glu Gln Asp Pro Ser Lys Ser Lys Val Val Val
                165                 170                 175

Phe Glu Asp Ala Pro Ala Gly Ile Ala Ala Gly Lys Ala Ala Gly Cys
            180                 185                 190

Lys Ile Val Gly Ile Ala Thr Thr Phe Asp Leu Asp Phe Leu Lys Glu
        195                 200                 205

Lys Gly Cys Asp Ile Ile Val Lys Asn His Glu Ser Ile Arg Val Gly
    210                 215                 220

Glu Tyr Asn Ala Glu Thr Asp Glu Val Glu Leu Ile Phe Asp Asp Tyr
225                 230                 235                 240

Leu Tyr Ala Lys Asp Asp Leu Leu Lys Trp
                245                 250

<210> SEQ ID NO 59
<211> LENGTH: 5779
<212> TYPE: DNA
<213> ORGANISM: Artificial Sequence
<220> FEATURE:
<223> OTHER INFORMATION: Synthetic pUC19-His-MhpF

<400> SEQUENCE: 59
tcgacctgca ggcatgcaag cttggcgtaa tcatggtcat agctgtttcc tgtgtgaaat      60
tgttatccgc tcacaattcc acacaacata cgagccggaa gcataaagtg taaagcctgg     120
ggtgcctaat gagtgagcta actcacatta attgcgttgc gctcactgcc cgctttccag     180
tcgggaaacc tgtcgtgcca gctgcattaa tgaatcggcc aacgcgcggg gagaggcggt     240
ttgcgtattg ggcgctcttc cgcttcctcg ctcactgact cgctgcgctc ggtcgttcgg     300
ctgcggcgag cggtatcagc tcactcaaag gcggtaatac ggttatccac agaatcaggg     360
gataacgcag gaaagaacat gtgagcaaaa ggccagcaaa aggccaggaa ccgtaaaaag     420
gccgcgttgc tggcgttttt ccataggctc cgcccccctg acgagcatca caaaaatcga     480
cgctcaagtc agaggtggcg aaacccgaca ggactataaa gataccaggc gtttccccct     540
ggaagctccc tcgtgcgctc tcctgttccg accctgccgc ttaccggata cctgtccgcc     600
tttctccctt cgggaagcgt ggcgctttct catagctcac gctgtaggta tctcagttcg     660
gtgtaggtcg ttcgctccaa gctgggctgt gtgcacgaac cccccgttca gcccgaccgc     720
tgcgccttat ccggtaacta tcgtcttgag tccaacccgg taagacacga cttatcgcca     780
ctggcagcag ccactggtaa caggattagc agagcgaggt atgtaggcgg tgctacagag     840
ttcttgaagt ggtggcctaa ctacggctac actagaagaa cagtatttgg tatctgcgct     900
ctgctgaagc cagttacctt cggaaaaaga gttggtagct cttgatccgg caaacaaacc     960
accgctggta gcggtggttt ttttgtttgc aagcagcaga ttacgcgcag aaaaaaagga    1020
tctcaagaag atcctttgat cttttctacg gggtctgacg ctcagtggaa cgaaaactca    1080
cgttaaggga ttttggtcat gagattatca aaaaggatct tcacctagat ccttttaaat    1140
taaaaatgaa gttttaaatc aatctaaagt atatatgagt aaacttggtc tgacagttac    1200
caatgcttaa tcagtgaggc acctatctca gcgatctgtc tatttcgttc atccatagtt    1260
gcctgactcc ccgtcgtgta gataactacg atacgggagg gcttaccatc tggccccagt    1320
```

```
gctgcaatga taccgcgaga cccacgctca ccggctccag atttatcagc aataaaccag    1380
ccagccggaa gggccgagcg cagaagtggt cctgcaactt tatccgcctc catccagtct    1440
attaattgtt gccgggaagc tagagtaagt agttcgccag ttaatagttt gcgcaacgtt    1500
gttgccattg ctacaggcat cgtggtgtca cgctcgtcgt ttggtatggc ttcattcagc    1560
tccggttccc aacgatcaag gcgagttaca tgatccccca tgttgtgcaa aaaagcggtt    1620
agctccttcg gtcctccgat cgttgtcaga agtaagttgg ccgcagtgtt atcactcatg    1680
gttatggcag cactgcataa ttctcttact gtcatgccat ccgtaagatg cttttctgtg    1740
actggtgagt actcaaccaa gtcattctga gaatagtgta tgcggcgacc gagttgctct    1800
tgcccggcgt caatacggga taataccgcg ccacatagca gaactttaaa agtgctcatc    1860
attggaaaac gttcttcggg gcgaaaactc tcaaggatct taccgctgtt gagatccagt    1920
tcgatgtaac ccactcgtgc acccaactga tcttcagcat cttttacttt caccagcgtt    1980
tctgggtgag caaaaacagg aaggcaaaat gccgcaaaaa agggaataag ggcgacacgg    2040
aaatgttgaa tactcatact cttccttttt caatattatt gaagcattta tcagggttat    2100
tgtctcatga gcggatacat atttgaatgt atttagaaaa ataaacaaat aggggttccg    2160
cgcacatttc cccgaaaagt gccacctgac gtctaagaaa ccattattat catgacatta    2220
acctataaaa ataggcgtat cacgaggccc tttcgtctcg cgcgtttcgg tgatgacggt    2280
gaaaacctct gacacatgca gctcccggag acggtcacag cttgtctgta agcggatgcc    2340
gggagcagac aagcccgtca gggcgcgtca gcgggtgttg gcgggtgtcg ggctggctt    2400 aactatgcgg catcagagca gattgtactg agagtgcacc atatgcggtg tgaaataccg    2460
cacagatgcg taaggagaaa ataccgcatc aggcgccatt cgccattcag gctgcgcaac    2520
tgttgggaag ggcgatcggt gcgggcctct tcgctattac gccagctggc gaaggggga    2580 tgtgctgcaa ggcgattaag ttgggtaacg ccagggtttt cccagtcacg acgttgtaaa    2640
acgacggcca gtgaattcga gctcagttta tcattatcaa tactcgccat tcaaagaat    2700 acgtaaataa ttaatagtag tgattttcct aactttattt agtcaaaaaa ttagcctttt    2760
aattctgctg taacccgtac atgcccaaaa taggggggcgg gttacacaga atatataaca    2820
tcgtaggtgt ctgggtgaac agtttattcc tggcatccac taaatataat ggagcccgct    2880
ttttaagctg gcatccagaa aaaaaagaa tcccagcacc aaaatattgt tttcttcacc    2940
aaccatcagt tcataggtcc attctcttag cgcaactaca gagaacaggg gcacaaacag    3000
gcaaaaaacg ggcacaacct caatggagtg atgcaacctg cctggagtaa atgatgacac    3060
aaggcaattg acccacgcat gtatctatct catttttctta caccttctat taccttctgc    3120
tctctctgat ttggaaaaag ctgaaaaaaa aggttgaaac cagttccctg aaattattcc    3180
cctacttgac taataagtat ataaagacgg taggtattga ttgtaattct gtaaatctat    3240
ttcttaaact tcttaaattc tactttttata gttagtcttt tttttagttt taaaacacca    3300
gaacttagtt tcgacggatt ctagaactag tggatccatg tcaaagcgaa aagtagctat    3360
cataggttca ggtaatattg gtactgattt tgatgatcaaa atcctgagac atggccagca    3420 cttgagatg gccgtcatgg ttggtatcga cccacaatcc gatggcttag ctagagctag    3480
gagaatgggt gttgccacaa ctcacgaagg ggttattggc ttaatgaaca tgccagaatt    3540
tgcagacatc gatatagttt ttgatgctac tagtgcaggg gcacatgtga aaaacgacgc    3600
ggctttaaga gaagccaagc cagatattag attaattgat cttaccccctg ctgctatagg    3660 tccttactgc gttcctgtag ttaaccttga agctaatgtg gaccagttga acgtgaatat    3720
```

-continued

```
ggttacatgt ggtggccaag ctaccatacc aatggttgct gctgtctcta gagtggccag    3780
agtacattat gccgagatca ttgcgtctat cgcatctaag tctgccggtc ctggaacaag    3840
ggctaacatc gatgagttca ctgagacaac ctctagagct atcgaagtag taggaggcgc    3900
agcaaaaggt aaagcgatca ttgttttgaa tcctgccgaa ccacctttga tgatgagaga    3960
tacggtctac gtgctatcag atgaagcttc ccaggatgac attgaagcta gcattaatga    4020
gatggcagaa gccgttcaag catacgtgcc aggatataga ctcaaacaaa gagtccaatt    4080
tgaggtcatt ccacaagaca agccagttaa tctcccaggg gtcggtcaat tctcaggact    4140
aaaaactgct gtttggttag aagtagaagg agctgctcat tacctaccag cctacgccgg    4200
taatttggat ataatgacat cttccgctct tgcaacagca gaaaagatgg cacaaagtct    4260
ggcccgtaag gcaggagaag cggcataata aatcctcgag tcatgtaatt agttatgtca    4320
cgcttacatt cacgccctcc ccccacatcc gctctaaccg aaaaggaagg agttagacaa    4380
cctgaagtct aggtccctat ttatttttt atagttatgt tagtattaag aacgttattt    4440
atatttcaaa ttttctttt tttctgtac agacgcgtgt acgcatgtaa cattatactg    4500
aaaaccttgc ttgagaaggt tttgggacgc tcgaaggctt taatttgcgg ccggtaccca    4560
attcgagctc ggtacccggg gatcctctag agtcgacaat tcccgtttta agagcttggt    4620
gagcgctagg agtcactgcc aggtatcgtt tgaacacggc attagtcagg gaagtcataa    4680
cacagtcctt tcccgcaatt ttcttttct attactcttg gcctcctcta gtacactcta    4740
tattttttta tgcctcggta atgattttca ttttttttt tccctagcg gatgactctt    4800
ttttttcttt agcgattggc attatcacat aatgaattat acattatata agtaatgtg    4860
atttcttcga agaatatact aaaaaatgag caggcaagat aaacgaaggc aaagatgaca    4920
gagcagaaag ccctagtaaa gcgtattaca aatgaaacca agattcagat tgcgatctct    4980
ttaaagggtg gtccctagc gatagagcac tcgatcttcc cagaaaaaga ggcagaagca    5040
gtagcagaac aggccacaca atcgcaagtg attaacgtcc acacaggtat agggtttctg    5100
gaccatatga tacatgctct ggccaagcat tccggctggt cgctaatcgt tgagtgcatt    5160
ggtgacttac acatagacga ccatcacacc actgaagact gcgggattgc tctcggtcaa    5220
gcttttaaag aggccctact ggcgcgtgga gtaaaaaggt ttggatcagg atttgcgcct    5280
ttggatgagg cactttccag agcggtggta gatcttcga acaggccgta cgcagttgtc    5340
gaacttggtt tgcaaaggga gaaagtagga gatctctctt gcgagatgat cccgcatttt    5400
cttgaaagct ttgcagaggc tagcagaatt accctccacg ttgattgtct gcgaggcaag    5460
aatgatcatc accgtagtga gagtgcgttc aaggctcttg cggttgccat aagagaagcc    5520
acctcgccca atggtaccaa cgatgttccc tccaccaaag gtgttcttat gtagtgacac    5580
cgattattta aagctgcagc atacgatata tatacatgtg tatatatgta tacctatgaa    5640
tgtcagtaag tatgtatacg aacagtatga tactgaagat gacaaggtaa tgcatcattc    5700
tatacgtgtc attctgaacg aggcgcgctt cctttttc ttttgcttt tcttttttt    5760
ttctcttgaa ctcgacggg                                                5779
```

<210> SEQ ID NO 60
<211> LENGTH: 500
<212> TYPE: PRT
<213> ORGANISM: Saccharomyces cerevisiae

<400> SEQUENCE: 60

-continued

```
Met Thr Lys Leu His Phe Asp Thr Ala Glu Pro Val Lys Ile Thr Leu
  1               5                   10                  15

Pro Asn Gly Leu Thr Tyr Glu Gln Pro Thr Gly Leu Phe Ile Asn Asn
             20                  25                  30

Lys Phe Met Lys Ala Gln Asp Gly Lys Thr Tyr Pro Val Glu Asp Pro
             35                  40                  45

Ser Thr Glu Asn Thr Val Cys Glu Val Ser Ser Ala Thr Thr Glu Asp
 50                  55                  60

Val Glu Tyr Ala Ile Glu Cys Ala Asp Arg Ala Phe His Asp Thr Glu
 65                  70                  75                  80

Trp Ala Thr Gln Asp Pro Arg Glu Arg Gly Arg Leu Leu Ser Lys Leu
                 85                  90                  95

Ala Asp Glu Leu Glu Ser Gln Ile Asp Leu Val Ser Ser Ile Glu Ala
                100                 105                 110

Leu Asp Asn Gly Lys Thr Leu Ala Leu Ala Arg Gly Asp Val Thr Ile
            115                 120                 125

Ala Ile Asn Cys Leu Arg Asp Ala Ala Ala Tyr Ala Asp Lys Val Asn
        130                 135                 140

Gly Arg Thr Ile Asn Thr Gly Asp Gly Tyr Met Asn Phe Thr Thr Leu
145                 150                 155                 160

Glu Pro Ile Gly Val Cys Gly Gln Ile Ile Pro Trp Asn Phe Pro Ile
                165                 170                 175

Met Met Leu Ala Trp Lys Ile Ala Pro Ala Leu Ala Met Gly Asn Val
            180                 185                 190

Cys Ile Leu Lys Pro Ala Ala Val Thr Pro Leu Asn Ala Leu Tyr Phe
        195                 200                 205

Ala Ser Leu Cys Lys Lys Val Gly Ile Pro Ala Gly Val Val Asn Ile
        210                 215                 220

Val Pro Gly Pro Gly Arg Thr Val Gly Ala Ala Leu Thr Asn Asp Pro
225                 230                 235                 240

Arg Ile Arg Lys Leu Ala Phe Thr Gly Ser Thr Glu Val Gly Lys Ser
                245                 250                 255

Val Ala Val Asp Ser Ser Glu Ser Asn Leu Lys Lys Ile Thr Leu Glu
            260                 265                 270

Leu Gly Gly Lys Ser Ala His Leu Val Phe Asp Asp Ala Asn Ile Lys
        275                 280                 285

Lys Thr Leu Pro Asn Leu Val Asn Gly Ile Phe Lys Asn Ala Gly Gln
        290                 295                 300

Ile Cys Ser Ser Gly Ser Arg Ile Tyr Val Gln Glu Gly Ile Tyr Asp
305                 310                 315                 320

Glu Leu Leu Ala Ala Phe Lys Ala Tyr Leu Glu Thr Glu Ile Lys Val
                325                 330                 335

Gly Asn Pro Phe Asp Lys Ala Asn Phe Gln Gly Ala Ile Thr Asn Arg
            340                 345                 350

Gln Gln Phe Asp Thr Ile Met Asn Tyr Ile Asp Ile Gly Lys Lys Glu
        355                 360                 365

Gly Ala Lys Ile Leu Thr Gly Gly Glu Lys Val Gly Asp Lys Gly Tyr
        370                 375                 380

Phe Ile Arg Pro Thr Val Phe Tyr Asp Val Asn Glu Asp Met Arg Ile
385                 390                 395                 400

Val Lys Glu Glu Ile Phe Gly Pro Val Val Thr Val Ala Lys Phe Lys
                405                 410                 415

Thr Leu Glu Glu Gly Val Glu Met Ala Asn Ser Ser Glu Phe Gly Leu
```

```
                420             425             430
Gly Ser Gly Ile Glu Thr Glu Ser Leu Ser Thr Gly Leu Lys Val Ala
            435             440             445

Lys Met Leu Lys Ala Gly Thr Val Trp Ile Asn Thr Tyr Asn Asp Phe
        450             455             460

Asp Ser Arg Val Pro Phe Gly Gly Val Lys Gln Ser Gly Tyr Gly Arg
465             470             475             480

Glu Met Gly Glu Glu Val Tyr His Ala Tyr Thr Glu Val Lys Ala Val
                485             490             495

Arg Ile Lys Leu
            500

<210> SEQ ID NO 61
<211> LENGTH: 1503
<212> TYPE: DNA
<213> ORGANISM: Saccharomyces cerevisiae

<400> SEQUENCE: 61
```

| | | | | | |
|---|---|---|---|---|---|
| atgactaagc | tacactttga | cactgctgaa | ccagtcaaga | tcacacttcc | aaatggtttg | 60 |
| acatacgagc | aaccaaccgg | tctattcatt | aacaacaagt | ttatgaaagc | tcaagacggt | 120 |
| aagacctatc | ccgtcgaaga | tccttccact | gaaaacaccg | tttgtgaggt | ctcttctgcc | 180 |
| accactgaag | atgttgaata | tgctatcgaa | tgtgccgacc | gtgctttcca | cgacactgaa | 240 |
| tgggctaccc | aagacccaag | agaaagaggc | cgtctactaa | gtaagttggc | tgacgaattg | 300 |
| gaaagccaaa | ttgacttggt | ttcttccatt | gaagctttgg | acaatggtaa | aactttggcc | 360 |
| ttagcccgtg | gggatgttac | cattgcaatc | aactgtctaa | gagatgctgc | tgcctatgcc | 420 |
| gacaaagtca | acggtagaac | aatcaacacc | ggtgacggct | acatgaactt | caccacctta | 480 |
| gagccaatcg | gtgtctgtgg | tcaaattatt | ccatggaact | ttccaataat | gatgttggct | 540 |
| tggaagatcg | ccccagcatt | ggccatgggt | aacgtctgta | tcttgaaacc | cgctgctgtc | 600 |
| acacctttaa | atgccctata | ctttgcttct | ttatgtaaga | aggttggtat | tccagctggt | 660 |
| gtcgtcaaca | tcgttccagg | tcctggtaga | actgttggtg | ctgctttgac | caacgaccca | 720 |
| agaatcagaa | agctggcttt | taccggttct | acagaagtcg | gtaagagtgt | tgctgtcgac | 780 |
| tcttctgaat | ctaacttgaa | gaaaatcact | ttggaactag | gtggtaagtc | cgcccatttg | 840 |
| gtctttgacg | atgctaacat | taagaagact | ttaccaaatc | tagtaaacgg | tattttcaag | 900 |
| aacgctggtc | aaatttgttc | ctctggttct | agaatttacg | ttcaagaagg | tatttacgac | 960 |
| gaactattgg | ctgctttcaa | ggcttacttg | gaaaccgaaa | tcaaagttgg | taatccattt | 1020 |
| gacaaggcta | acttccaagg | tgctatcact | aaccgtcaac | aattcgacac | aattatgaac | 1080 |
| tacatcgata | tcggtaagaa | agaaggcgcc | aagatcttaa | ctggtggcga | aaaagttggt | 1140 |
| gacaagggtt | acttcatcag | accaaccgtt | ttctacgatg | ttaatgaaga | catgagaatt | 1200 |
| gttaaggaag | aaattttttgg | accagttgtc | actgtcgcaa | agttcaagac | tttagaagaa | 1260 |
| ggtgtcgaaa | tggctaacag | ctctgaattc | ggtctaggtt | ctggtatcga | aacagaatct | 1320 |
| ttgagcacag | gtttgaaggt | ggccaagatg | ttgaaggccg | gtaccgtctg | gatcaacaca | 1380 |
| tacaacgatt | ttgactccag | agttccattc | ggtggtgtta | agcaatctgg | ttacggtaga | 1440 |
| gaaatgggtg | aagaagtcta | ccatgcatac | actgaagtaa | aagctgtcag | aattaagttg | 1500 |
| taa | | | | | | 1503 |

```
<210> SEQ ID NO 62
```

```
<211> LENGTH: 31
<212> TYPE: DNA
<213> ORGANISM: Artificial Sequence
<220> FEATURE:
<223> OTHER INFORMATION: Synthetic primer

<400> SEQUENCE: 62
cctcctgagt cgacaattcc cgttttaaga g                              31

<210> SEQ ID NO 63
<211> LENGTH: 30
<212> TYPE: DNA
<213> ORGANISM: Artificial Sequence
<220> FEATURE:
<223> OTHER INFORMATION: Synthetic primer

<400> SEQUENCE: 63
cgaccgtggt cgacccgtcg agttcaagag                                30

<210> SEQ ID NO 64
<211> LENGTH: 67
<212> TYPE: DNA
<213> ORGANISM: Artificial Sequence
<220> FEATURE:
<223> OTHER INFORMATION: Synthetic primer

<400> SEQUENCE: 64
tatatatttc aaggatatac cattctaatg tctgcccta agaagatcgt gctgcaaggc     60
gattaag                                                             67

<210> SEQ ID NO 65
<211> LENGTH: 67
<212> TYPE: DNA
<213> ORGANISM: Artificial Sequence
<220> FEATURE:
<223> OTHER INFORMATION: Synthetic primer

<400> SEQUENCE: 65
gagaatcttt ttaagcaagg attttcttaa cttcttcggc gacagcatcg gctcgtatgt    60
tgtgtgg                                                             67

<210> SEQ ID NO 66
<211> LENGTH: 20
<212> TYPE: DNA
<213> ORGANISM: Artificial Sequence
<220> FEATURE:
<223> OTHER INFORMATION: Synthetic primer

<400> SEQUENCE: 66
gtttcgtcta ccctatgaac                                           20

<210> SEQ ID NO 67
<211> LENGTH: 21
<212> TYPE: DNA
<213> ORGANISM: Artificial Sequence
<220> FEATURE:
<223> OTHER INFORMATION: Synthetic primer

<400> SEQUENCE: 67
ccaataggtg gttagcaatc g                                         21

<210> SEQ ID NO 68
<211> LENGTH: 64
<212> TYPE: DNA
<213> ORGANISM: Artificial Sequence
```

```
<220> FEATURE:
<223> OTHER INFORMATION: Synthetic primer

<400> SEQUENCE: 68
caagaaacat ctttaacata cacaaacaca tactatcaga atacccagtc acgacgttgt    60
aaaa                                                                 64

<210> SEQ ID NO 69
<211> LENGTH: 65
<212> TYPE: DNA
<213> ORGANISM: Artificial Sequence
<220> FEATURE:
<223> OTHER INFORMATION: Synthetic primer

<400> SEQUENCE: 69
gtattttgtg tatatgacgg aaagaaatgc aggttggtac attacaggtt tcccgactgg    60
aaagc                                                                65

<210> SEQ ID NO 70
<211> LENGTH: 24
<212> TYPE: DNA
<213> ORGANISM: Artificial Sequence
<220> FEATURE:
<223> OTHER INFORMATION: Synthetic primer

<400> SEQUENCE: 70
gcatcgggaa cgtatgtaac attg                                           24

<210> SEQ ID NO 71
<211> LENGTH: 19
<212> TYPE: DNA
<213> ORGANISM: Artificial Sequence
<220> FEATURE:
<223> OTHER INFORMATION: Synthetic primer

<400> SEQUENCE: 71
tgacgtaaga ccaagtaag                                                 19

<210> SEQ ID NO 72
<211> LENGTH: 55
<212> TYPE: DNA
<213> ORGANISM: Artificial Sequence
<220> FEATURE:
<223> OTHER INFORMATION: Synthetic primer

<400> SEQUENCE: 72
ctatagggcg aattggctag cttatcatta tcaatactcg ccatttcaaa gaata          55

<210> SEQ ID NO 73
<211> LENGTH: 66
<212> TYPE: DNA
<213> ORGANISM: Artificial Sequence
<220> FEATURE:
<223> OTHER INFORMATION: Synthetic primer

<400> SEQUENCE: 73
ctcgaggggg ggcccggtac ctcgaaacta agttctggtg ttttaaaact aaaaaaaga     60 ctaact                                                               66

<210> SEQ ID NO 74
<211> LENGTH: 6110
<212> TYPE: DNA
<213> ORGANISM: Artificial Sequence
<220> FEATURE:
```

<223> OTHER INFORMATION: Synthetic pCS-Ex1 vector

<400> SEQUENCE: 74

```
ctaaattgta agcgttaata ttttgttaaa attcgcgtta aattttttgtt aaatcagctc      60
atttttaac caataggccg aaatcggcaa atcccttat aaatcaaaag aatagaccga       120
gatagggttg agtacgcatt taagcataaa cacgcactat gccgttcttc tcatgtatat     180
atatatacag gcaacacgca gatataggtg cgacgtgaac agtgagctgt atgtgcgcag     240
ctcgcgttgc attttcggaa gcgctcgttt tcggaaacgc tttgaagttc ctattccgaa     300
gttcctattc tctagctaga aagtatagga acttcagagc gcttttgaaa accaaaagcg    360
ctctgaagac gcactttcaa aaaccaaaa acgcaccgga ctgtaacgag ctactaaaat     420
attgcgaata ccgcttccac aaacattgct caaaagtatc tctttgctat atatctctgt   480
gctatatccc tatataacct acccatccac ctttcgctcc ttgaacttgc atctaaactc    540
gacctctaca ttttttatgt ttatctctag tattactctt tagacaaaaa aattgtagta   600
agaactattc atagagtgaa tcgaaaacaa tacgaaaatg taaacatttc ctatacgtag    660
tatatagaga caaatagaa gaaaccgttc ataattttct gaccaatgaa gaatcatcaa    720
cgctatcact ttctgttcac aaagtatgcg caatccacat cggtatagaa tataatcggg   780
gatgccttta tcttgaaaaa atgcacccgc agcttcgcta gtaatcagta aacgcgggaa   840
gtggagtcag gcttttttta tggaagagaa aatagacacc aaagtagcct tcttctaacc   900
ttaacggacc tacagtgcaa aaagttatca agagactgca ttatagagcg cacaaaggag   960
aaaaaaagta atctaagatg ctttgttaga aaaatagcgc tctcgggatg catttttgta  1020
gaacaaaaaa gaagtataga ttctttgttg gtaaaatagc gctctcgcgt tgcatttctg  1080
ttctgtaaaa atgcagctca gattctttgt ttgaaaaatt agcgctctcg cgttgcattt  1140
ttgttttaca aaaatgaagc acagattctt cgttggtaaa atagcgcttt cgcgttgcat  1200
ttctgttctg taaaaatgca gctcagattc tttgtttgaa aaattagcgc tctcgcgttg  1260
cattttgtt ctacaaaatg aagcacagat gcttcgttaa tgtgctgcaa ggcgattaag  1320
ttgggtaacg ccagggtttt cccagtcacg acgttgtaaa acgacggcca gtgaattgta  1380
atacgactca ctatagggcg aattggctag cttatcatta tcaatactcg ccatttcaaa  1440
gaatacgtaa ataattaata gtagtgattt tcctaacttt atttagtcaa aaaattagcc  1500
ttttaattct gctgtaaccc gtacatgccc aaaataggggg gcgggttaca cagaatatat  1560
aacatcgtag gtgtctgggt gaacagttta ttcctggcat ccactaaata taatggagcc  1620
cgctttttaa gctggcatcc agaaaaaaaa agaatcccag caccaaaata ttgttttctt  1680
caccaaccat cagttcatag gtccattctc ttagcgcaac tacagagaac aggggcacaa  1740
acaggcaaaa aacgggcaca acctcaatgg agtgatgcaa cctgcctgga gtaaatgatg  1800
acacaaggca attgacccac gcatgtatct atctcatttt cttacacctt ctattacctt  1860
ctgctctctc tgatttggaa aaagctgaaa aaaaaggttg aaaccagttc cctgaaatta  1920
ttcccctact tgactaataa gtatataaag acggtaggta ttgattgtaa ttctgtaaat  1980
ctatttctta aacttcttaa attctacttt tatagttagt cttttttta gttttaaaac    2040
accagaactt agtttcgagg taccgggccc ccctcgagg tcgacggtat cgataagctt   2100
gatatcgaat tcctgcagcc cgggggatcc actagttcta gagcggccgc caccgcggtg  2160
gagctcggtt ctgcttatcc ttacgacgtg cctgactacg cctgaacccg atgcaaatga  2220
gacgatcgtc tattcctggt ccggttttct ctgccctctc ttctattcac ttttttata   2280
```

```
ctttatataa aattatataa atgacataac tgaaacgcca cacgtcctct cctattcgtt    2340
aacgcctgtc tgtagcgctg ttactgaagc tgcgcaagta gttttttcac cgtataggcc    2400
ctcttttcct ctctctttct ttctctcccg cgctgatctc ttcttcgaaa cacagagtgc    2460
accataccac cttttcaatt catcattttt tttttattct tttttttgat ttcggtttcc    2520
ttgaaatttt tttgattcgg taatctccga acagaaggaa gaacgaagga aggagcacag    2580
acttagattg gtatatatac gcatatgtag tgttgaagaa acatgaaatt gcccagtatt    2640
cttaacccaa ctgcacagaa caaaaacctc caggaaacga agataaatca tgtcgaaagc    2700
tacatataag gaacgtgctg ctactcatcc tagtcctgtt gctgccaagc tatttaatat    2760
catgcacgaa aagcaaacaa acttgtgtgc ttcattggat gttcgtacca ccaaggaatt    2820
actggagtta gttgaagcat taggtcccaa aatttgttta ctaaaaacac atgtggatat    2880
cttgactgat ttttccatgg agggcacagt taagccgcta aaggcattat ccgccaagta    2940 caattttta ctcttcgaag acagaaaatt tgctgacatt ggtaatacag tcaaattgca    3000
gtactctgcg ggtgtataca gaatagcaga atgggcagac attacgaatg cacacggtgt    3060
ggtgggccca ggtattgtta gcggtttgaa gcaggcggca gaagaagtaa caaaggaacc    3120
tagaggcctt ttgatgttag cagaattgtc atgcaagggc tccctatcta ctggagaata    3180
tactaagggt actgttgaca ttgcgaagag cgacaaagat tttgttatcg gctttattgc    3240
tcaaagagac atgggtggaa gagatgaagg ttacgattgg ttgattatga cacccggtgt    3300
gggtttagat gacaagggag acgcattggg tcaacagtat agaaccgtgg atgatgtggt    3360
ctctacagga tctgacatta ttattgttgg aagaggacta tttgcaaagg gaagggatgc    3420
taaggtagag ggtgaacgtt acagaaaagc aggctgggaa gcatatttga gaagatgcgg    3480
ccagcaaaac taatcatgta attagttatg tcacgcttac attcacgccc tccccccaca    3540
tccgctctaa ccgaaaagga aggagttaga caacctgaag tctaggtccc tatttatttt    3600
tttatagtta tgttagtatt aagaacgtta tttatatttc aaattttttct ttttttttctg    3660 tacagacgcg tgtacgcatg taacattata ctgaaaacct tgcttgagaa ggttttggga    3720
cgctcgaagg ctttaatttg cgtctgtagc gctgttactg aagctgcgca agtagttttt    3780
tcaccgtata ggccctcttt ttctctctct ttctttctct cccgcgctga tctcttcttc    3840
gaaacatcat gaataaaaag aaaaaggaaa tcaagaaaaa aagccataa tttatcccac    3900 attttttttt attgtcgctg ttcacaccgc ataacgaaga tattggctag ctaaccagct    3960
tttgttccct ttagtgaggg ttaatttcga gcttggcgta atcatggtca tagctgtttc    4020
ctgtgtgaaa ttgttatccg ctcacaattc cacacaacat acgagccgga agcataaagt    4080
gtaaagcctg gggtgcctaa tgagtgagct aactcacatt aattgcgttg cgctcactgc    4140
ccgctttcca gtcgggaaac ctgtcgtgcc agctgcatta atgaatcggc caacgcgcgg    4200
ggagaggcgg tttgcgtatt gggcgctctt ccgcttcctc gctcactgac tcgctgcgct    4260
cggtcgttcg gctgcggcga gcggtatcag ctcactcaaa ggcggtaata cggttatcca    4320
cagaatcagg ggataacgca ggaaagaaca tgtgagcaaa aggccagcaa aaggccagga    4380
accgtaaaaa ggccgcgttg ctggcgtttt tccataggct ccgcccccct gacgagcatc    4440
acaaaaatcg acgctcaagt cagaggtggc gaaacccgac aggactataa agataccagg    4500
cgtttccccc tggaagctcc ctcgtgcgct ctcctgttcc gaccctgccg cttaccggat    4560
acctgtccgc ctttctccct tcgggaagcg tggcgctttc tcatagctca cgctgtaggt    4620
```

| | |
|---|---:|
| atctcagttc ggtgtaggtc gttcgctcca agctgggctg tgtgcacgaa ccccccgttc | 4680 |
| agcccgaccg ctgcgcctta tccggtaact atcgtcttga gtccaacccg gtaagacacg | 4740 |
| acttatcgcc actggcagca gccactggta acaggattag cagagcgagg tatgtaggcg | 4800 |
| gtgctacaga gttcttgaag tggtggccta actacggcta cactagaagg acagtatttg | 4860 |
| gtatctgcgc tctgctgaag ccagttacct tcggaaaaag agttggtagc tcttgatccg | 4920 |
| gcaaacaaac caccgctggt agcggtggtt ttttgtttg caagcagcag attacgcgca | 4980 |
| gaaaaaaagg atctcaagaa gatcctttga tcttttctac ggggtctgac gctcagtgga | 5040 |
| acgaaaactc acgttaaggg attttggtca tgagattatc aaaaaggatc ttcacctaga | 5100 |
| tccttttaaa ttaaaaatga agttttaaat caatctaaag tatatatgag taaacttggt | 5160 |
| ctgacatcag aagaactcgt caagaaggcg atagaaggcg atgcgctgcg aatcgggagc | 5220 |
| ggcgataccg taaagcacga ggaagcggtc agcccattcg ccgccaagct cttcagcaat | 5280 |
| atcacgggta gccaacgcta tgtcctgata gcggtccgcc acacccagcc ggccacagtc | 5340 |
| gatgaatcca gaaaagcggc cattttccac catgatattc ggcaagcagg catcgccatg | 5400 |
| ggtcacgacg agatcctcgc cgtcgggcat gctcgccttg agcctggcga acagttcggc | 5460 |
| tggcgcgagc ccctgatgct cttcgtccag atcatcctga tcgacaagac cggcttccat | 5520 |
| ccgagtacgt gctcgctcga tgcgatgttt cgcttggtgg tcgaatgggc aggtagccgg | 5580 |
| atcaagcgta tgcagccgcc gcattgcatc agccatgatg gatactttct cggcaggagc | 5640 |
| aaggtgagat gacaggagat cctgccccgg cacttcgccc aatagcagcc agtcccttcc | 5700 |
| cgcttcagtg acaacgtcga gcacagctgc gcaaggaacg cccgtcgtgg ccagccacga | 5760 |
| tagccgcgct gcctcgtctt gcagttcatt cagggcaccg gacaggtcgg tcttgacaaa | 5820 |
| aagaaccggg cgcccctgcg ctgacagccg gaacacggcg gcatcagagc agccgattgt | 5880 |
| ctgttgtgcc cagtcatagc cgaatagcct ctccacccaa gcggccggag aacctgcgtg | 5940 |
| caatccatct tgttcaattc gagtgcattc aacatcagcc atactcttcc tttttcaata | 6000 |
| ttattgaagc atttatcagg gttattgtct catgagcgga tacatatttg aatgtattta | 6060 |
| gaaaaataaa caaatagggg ttccgcgcac atttccccga aaagtgccac | 6110 |

<210> SEQ ID NO 75
<211> LENGTH: 55
<212> TYPE: DNA
<213> ORGANISM: Artificial Sequence
<220> FEATURE:
<223> OTHER INFORMATION: Synthetic primer

<400> SEQUENCE: 75
accagaactt agtttcgaga acaatgaat caacaggata ttgaacaggt ggtga    55

<210> SEQ ID NO 76
<211> LENGTH: 50
<212> TYPE: DNA
<213> ORGANISM: Artificial Sequence
<220> FEATURE:
<223> OTHER INFORMATION: Synthetic primer

<400> SEQUENCE: 76
gtaaggataa gcagaaccgt taaacaatgc gaaacgcatc gactaataca    50

<210> SEQ ID NO 77
<211> LENGTH: 7413
<212> TYPE: DNA
<213> ORGANISM: Artificial Sequence
<220> FEATURE:
<223> OTHER INFORMATION: Synthetic MD1040 vector

<400> SEQUENCE: 77

```
ctaaattgta agcgttaata ttttgttaaa attcgcgtta aatttttgtt aaatcagctc      60
attttttaac caataggccg aaatcggcaa atcccttat aaatcaaaag aatagaccga     120
gatagggttg agtacgcatt taagcataaa cacgcactat gccgttcttc tcatgtatat     180
atatatacag gcaacacgca gatataggtg cgacgtgaac agtgagctgt atgtgcgcag    240
ctcgcgttgc attttcggaa gcgctcgttt tcggaaacgc tttgaagttc ctattccgaa    300
gttcctattc tctagctaga aagtatagga acttcagagc gcttttgaaa accaaaagcg    360
ctctgaagac gcactttcaa aaaccaaaa acgcaccgga ctgtaacgag ctactaaaat    420
attgcgaata ccgcttccac aaacattgct caaaagtatc tctttgctat atatctctgt    480
gctatatccc tatataacct acccatccac ctttcgctcc ttgaacttgc atctaaactc    540
gacctctaca ttttttatgt ttatctctag tattactctt tagacaaaaa aattgtagta    600
agaactattc atagagtgaa tcgaaaacaa tacgaaaatg taaacatttc ctatacgtag    660
tatatagaga caaaatagaa gaaaccgttc ataattttct gaccaatgaa gaatcatcaa    720
cgctatcact ttctgttcac aaagtatgcg caatccacat cggtatagaa tataatcggg    780
gatgccttta tcttgaaaaa atgcacccgc agcttcgcta gtaatcagta aacgcgggaa    840
gtggagtcag gctttttta tggaagagaa aatagacacc aaagtagcct tcttctaacc    900
ttaacggacc tacagtgcaa aaagttatca agagactgca ttatagagcg cacaaaggag    960
aaaaaagta atctaagatg ctttgttaga aaaatagcgc tctcgggatg cattttgta   1020
gaacaaaaaa gaagtataga ttctttgttg gtaaaatagc gctctcgcgt tgcatttctg   1080
ttctgtaaaa atgcagctca gattctttgt ttgaaaaatt agcgctctcg cgttgcattt   1140
ttgttttaca aaaatgaagc acagattctt cgttggtaaa atagcgcttt cgcgttgcat   1200
ttctgttctg taaaaatgca gctcagattc tttgtttgaa aaattagcgc tctcgcgttg   1260
cattttgtt ctacaaaatg aagcacagat gcttcgttaa tgtgctgcaa ggcgattaag   1320
ttgggtaacg ccagggtttt cccagtcacg acgttgtaaa acgacggcca gtgaattgta   1380
atacgactca ctatagggcg aattggctag cttatcatta tcaatactcg ccatttcaaa   1440
gaatacgtaa ataattaata gtagtgattt tcctaacttt atttagtcaa aaaattagcc   1500
ttttaattct gctgtaaccc gtacatgccc aaaataggg gcgggttaca cagaatatat   1560
aacatcgtag gtgtctgggt gaacagttta ttcctggcat ccactaaata taatggagcc   1620
cgcttttaa gctggcatcc agaaaaaaaa agaatcccag caccaaaata ttgttttctt   1680
caccaaccat cagttcatag gtccattctc ttagcgcaac tacagagaac aggggcacaa   1740
acaggcaaaa aacgggcaca acctcaatgg agtgatgcaa cctgcctgga gtaaatgatg   1800
acacaaggca attgacccac gcatgtatct atctcatttt cttacacctt ctattacctt   1860
ctgctctctc tgatttggaa aaagctgaaa aaaaggttg aaaccagttc cctgaaatta   1920
ttcccctact tgactaataa gtatataaag acggtaggta ttgattgtaa ttctgtaaat   1980
ctatttctta aacttcttaa attctacttt tatagttagt ctttttttta gttttaaaac   2040
accagaactt agtttcgaga aacaatgaat caacaggata ttgaacaggt ggtgaaagcg   2100
gtactgctga aaatgcaaag cagtgacacg ccgtccgccg ccgttcatga gatggcgtt   2160
ttcgcgtccc tggatgacgc cgttgcggca gccaaagtcg cccagcaagg gttaaaaagc   2220
```

```
gtggcaatgc gccagttagc cattgctgcc attcgtgaag caggcgaaaa acacgccaga      2280
gatttagcgg aacttgccgt cagtgaaacc ggcatggggc gcgttgaaga taaatttgca      2340
aaaaacgtcg ctcaggcgcg cggcacacca ggcgttgagt gcctctctcc gcaagtgctg      2400
actggcgaca acggcctgac cctaattgaa aacgcaccct ggggcgtggt ggcttcggtg      2460
acgccttcca ctaacccggc ggcaaccgta attaacaacg ccatcagcct gattgccgcg      2520
ggcaacagcg tcattttttgc cccgcatccg gcggcgaaaa aagtctccca gcgggcgatt      2580
acgctgctca accaggcgat tgttgccgca ggtgggccgg aaaacttact ggttactgtg      2640
gcaaatccgg atatcgaaac cgcgcaacgc ttgttcaagt ttccgggtat cggcctgctg      2700
gtggtaaccg gcggcgaagc ggtagtagaa gcggcgcgta acacaccaa taaacgtctg      2760 attgccgcag cgctggcaa cccgccgta gtggtggatg aaaccgccga cctcgcccgt      2820
gccgctcagt ccatcgtcaa aggcgcttct ttcgataaca acatcatttg tgccgacgaa      2880
aaggtactga ttgttgttga tagcgtagcc gatgaactga tgcgtctgat ggaaggccag      2940
cacgcggtga aactgaccgc agaacaggcg cagcagctgc aaccggtgtt gctgaaaaat      3000
atcgacgagc gcggaaaagg caccgtcagc cgtgactggg ttggtcgcga cgcaggcaaa      3060 atcgcggcg caatcggcct taaagttccg caagaaacgc gcctgctgtt tgtggaaacc      3120
accgcagaac atccgtttgc cgtgactgaa ctgatgatgc cggtgttgcc cgtcgtgcgc      3180
gtcgccaacg tggcggatgc cattgcgcta gcggtgaaac tggaaggcgg ttgccaccac      3240
acggcggcaa tgcactcgcg caacatcgaa acatgaacc agatggcgaa tgctattgat      3300
accagcattt tcgttaagaa cggaccgtgc attgccgggc tggggctggg cggggaaggc      3360
tggaccacca tgaccatcac cacgccaacc ggtgaagggg taaccagcgc gcgtacgttt      3420
gtccgtctgc gtcgctgtgt attagtcgat gcgtttcgca ttgtttaacg gttctgctta      3480
tccttacgac gtgcctgact acgcctgaac ccgatgcaaa tgagacgatc gtctattcct      3540
ggtccggttt tctctgccct ctcttctatt cacttttttt atactttata taaaattata      3600
taaatgacat aactgaaacg ccacacgtcc tctcctattc gttaacgcct gtctgtagcg      3660
ctgttactga agctgcgcaa gtagtttttt caccgtatag gccctctttt tctctctctt      3720
tctttctctc ccgcgctgat ctcttcttcg aaacacagag tgcaccatac cacctttttca      3780 attcatcatt tttttttat tctttttttt gatttcggtt tccttgaaat ttttttgatt      3840
cggtaatctc cgaacagaag gaagaacgaa ggaaggagca cagacttaga ttggtatata      3900
tacgcatatg tagtgttgaa gaaacatgaa attgcccagt attcttaacc caactgcaca      3960
gaacaaaaac ctccaggaaa cgaagataaa tcatgtcgaa agctacatat aaggaacgtg      4020
ctgctactca tcctagtcct gttgctgcca agctatttaa tatcatgcac gaaaagcaaa      4080
caaacttgtg tgcttcattg gatgttcgta ccaccaagga attactggag ttagttgaag      4140
cattaggtcc caaaatttgt ttactaaaaa cacatgtgga tatcttgact gatttttcca      4200
tggagggcac agttaagccg ctaaaggcat tatccgccaa gtacaatttt ttactcttcg      4260
aagacagaaa atttgctgac attggtaata cagtcaaatt gcagtactct gcgggtgtat      4320
acagaatagc agaatgggca gacattacga atgcacacgg tgtggtgggc ccaggtattg      4380
ttagcggttt gaagcaggcg gcagaagaag taacaaagga acctagaggc cttttgatgt      4440
tagcagaatt gtcatgcaag ggctccctat ctactggaga atatactaag ggtactgttg      4500
acattgcgaa gagcgacaaa gattttgtta tcggctttat tgctcaaaga gacatgggtg      4560
gaagagatga aggttacgat tggttgatta tgacacccgg tgtgggttta gatgacaagg      4620
```

```
gagacgcatt gggtcaacag tatagaaccg tggatgatgt ggtctctaca ggatctgaca   4680
ttattattgt tggaagagga ctatttgcaa agggaaggga tgctaaggta gagggtgaac   4740
gttacagaaa agcaggctgg gaagcatatt tgagaagatg cggccagcaa aactaatcat   4800
gtaattagtt atgtcacgct tacattcacg ccctccccc acatccgctc taaccgaaaa    4860
ggaaggagtt agacaacctg aagtctaggt ccctatttat tttttatag ttatgttagt    4920 attaagaacg ttatttatat ttcaaatttt tctttttttt ctgtacagac gcgtgtacgc   4980
atgtaacatt atactgaaaa ccttgcttga aaggttttg gacgctcga aggctttaat     5040 ttgcgtctgt agcgctgtta ctgaagctgc gcaagtagtt ttttcaccgt ataggccctc   5100 ttttctctc tctttctttc tctcccgcgc tgatctcttc ttcgaaacat catgaataaa    5160
aagaaaaagg aaatcaagaa aaaaaagcca taatttatcc cacatttttt tttattgtcg   5220
ctgttcacac cgcataacga agatattggc tagctaacca gcttttgttc cctttagtga   5280
gggttaattt cgagcttggc gtaatcatgg tcatagctgt ttcctgtgtg aaattgttat   5340
ccgctcacaa ttccacacaa catacgagcc ggaagcataa agtgtaaagc ctggggtgcc   5400
taatgagtga gctaactcac attaattgcg ttgcgctcac tgcccgcttt ccagtcggga   5460
aacctgtcgt gccagctgca ttaatgaatc ggccaacgcg cggggagagg cggtttgcgt   5520
attgggcgct cttccgcttc ctcgctcact gactcgctgc gctcggtcgt tcggctgcgg   5580
cgagcggtat cagctcactc aaaggcggta atacggttat ccacagaatc aggggataac   5640
gcaggaaaga acatgtgagc aaaaggccag caaaaggcca ggaaccgtaa aaaggccgcg   5700
ttgctggcgt ttttccatag gctccgcccc cctgacgagc atcacaaaaa tcgacgctca   5760
agtcagaggt ggcgaaaccc gacaggacta taaagatacc aggcgtttcc ccctggaagc   5820
tccctcgtgc gctctcctgt tccgaccctg ccgcttaccg gatacctgtc cgcctttctc   5880
ccttcgggaa gcgtggcgct ttctcatagc tcacgctgta ggtatctcag ttcggtgtag   5940
gtcgttcgct ccaagctggg ctgtgtgcac gaaccccccg ttcagcccga ccgctgcgcc   6000
ttatccggta actatcgtct tgagtccaac ccggtaagac acgacttatc gccactggca   6060
gcagccactg gtaacaggat tagcagagcg aggtatgtag gcggtgctac agagttcttg   6120
aagtggtggc ctaactacgg ctacactaga aggacagtat ttggtatctg cgctctgctg   6180
aagccagtta ccttcggaaa aagagttggt agctcttgat ccggcaaaca aaccaccgct   6240
ggtagcggtg gtttttttgt ttgcaagcag cagattacgc gcagaaaaaa aggatctcaa   6300
gaagatcctt tgatcttttc tacggggtct gacgctcagt ggaacgaaaa ctcacgttaa   6360
gggattttgg tcatgagatt atcaaaaagg atcttcacct agatcctttt aaattaaaaa   6420
tgaagtttta aatcaatcta agtatatat gagtaaactt ggtctgacat cagaagaact    6480
cgtcaagaag gcgatagaag gcgatgcgct gcgaatcggg agcggcgata ccgtaaagca   6540
cgaggaagcg gtcagcccat tcgccgccaa gctcttcagc aatatcacgg gtagccaacg   6600
ctatgtcctg atagcggtcc gccacaccca gccggccaca gtcgatgaat ccagaaaagc   6660
ggccattttc caccatgata ttcggcaagc aggcatcgcc atgggtcacg acgagatcct   6720
cgccgtcggg catgctcgcc ttgagcctgg cgaacagttc ggctggcgcg agcccctgat   6780
gctcttcgtc cagatcatcc tgatcgacaa gaccggcttc catccgagta cgtgctcgct   6840
cgatgcgatg tttcgcttgg tggtcgaatg ggcaggtagc cggatcaagc gtatgcagcc   6900
gccgcattgc atcagccatg atggatactt tctcggcagg agcaaggtga gatgacagga   6960
```

-continued

```
gatcctgccc cggcacttcg cccaatagca gccagtccct tcccgcttca gtgacaacgt   7020
cgagcacagc tgcgcaagga acgcccgtcg tggccagcca cgatagccgc gctgcctcgt   7080
cttgcagttc attcagggca ccggacaggt cggtcttgac aaaaagaacc gggcgcccct   7140
gcgctgacag ccggaacacg gcggcatcag agcagccgat tgtctgttgt gcccagtcat   7200
agccgaatag cctctccacc caagcggccg gagaacctgc gtgcaatcca tcttgttcaa   7260
ttcgagtgca ttcaacatca gccatactct tccttttttca atattattga agcatttatc   7320
agggttattg tctcatgagc ggatacatat ttgaatgtat ttagaaaaat aaacaaatag   7380
gggttccgcg cacatttccc cgaaaagtgc cac                                 7413
```

<210> SEQ ID NO 78
<211> LENGTH: 59
<212> TYPE: DNA
<213> ORGANISM: Artificial Sequence
<220> FEATURE:
<223> OTHER INFORMATION: Synthetic primer

<400> SEQUENCE: 78

```
aatcttgtgc tattgcagtc ctcttttata tacagtataa tacgactcac tatagggcg      59
```

<210> SEQ ID NO 79
<211> LENGTH: 60
<212> TYPE: DNA
<213> ORGANISM: Artificial Sequence
<220> FEATURE:
<223> OTHER INFORMATION: Synthetic primer

<400> SEQUENCE: 79

```
atgcgaattg cgtaattcac ggcgataacg tagtattaat taaccctcac taaagggaac     60
```

<210> SEQ ID NO 80
<211> LENGTH: 19
<212> TYPE: DNA
<213> ORGANISM: Artificial Sequence
<220> FEATURE:
<223> OTHER INFORMATION: Synthetic primer

<400> SEQUENCE: 80

```
gcccacaact tatcaagtg                                                  19
```

<210> SEQ ID NO 81
<211> LENGTH: 19
<212> TYPE: DNA
<213> ORGANISM: Artificial Sequence
<220> FEATURE:
<223> OTHER INFORMATION: Synthetic primer

<400> SEQUENCE: 81

```
ttataagaca agcgcaggg                                                  19
```

<210> SEQ ID NO 82
<211> LENGTH: 312
<212> TYPE: PRT
<213> ORGANISM: Pseudomonas sp. CF600

<400> SEQUENCE: 82

```
Met Asn Gln Lys Leu Lys Val Ala Ile Ile Gly Ser Gly Asn Ile Gly
 1               5                  10                  15

Thr Asp Leu Met Ile Lys Val Leu Arg Asn Ala Lys Tyr Leu Glu Met
             20                  25                  30

Gly Ala Met Val Gly Ile Asp Ala Ala Ser Asp Gly Leu Ala Arg Ala
```

-continued

```
                35                  40                  45
Gln Arg Met Gly Val Thr Thr Thr Tyr Ala Gly Val Glu Gly Leu Ile
             50                  55                  60

Lys Leu Pro Glu Phe Ala Asp Ile Asp Phe Val Phe Asp Ala Thr Ser
 65                  70                  75                  80

Ala Ser Ala His Val Gln Asn Glu Ala Leu Leu Arg Gln Ala Lys Pro
                 85                  90                  95

Gly Ile Arg Leu Ile Asp Leu Thr Pro Ala Ala Ile Gly Pro Tyr Cys
            100                 105                 110

Val Pro Val Val Asn Leu Glu Glu His Leu Gly Lys Leu Asn Val Asn
            115                 120                 125

Met Val Thr Cys Gly Gly Gln Ala Thr Ile Pro Met Val Ala Ala Val
            130                 135                 140

Ser Arg Val Ala Lys Val His Tyr Ala Glu Ile Val Ala Ser Ile Ser
145                 150                 155                 160

Ser Lys Ser Ala Gly Pro Gly Thr Arg Ala Asn Ile Asp Glu Phe Thr
                165                 170                 175

Glu Thr Thr Ser Lys Ala Ile Glu Val Ile Gly Gly Ala Ala Lys Gly
                180                 185                 190

Lys Ala Ile Ile Ile Met Asn Pro Ala Glu Pro Leu Ile Met Arg
            195                 200                 205

Asp Thr Val Tyr Val Leu Ser Ala Ala Ala Asp Gln Ala Ala Val Ala
            210                 215                 220

Ala Ser Val Ala Glu Met Val Gln Ala Val Gln Ala Tyr Val Pro Gly
225                 230                 235                 240

Tyr Arg Leu Lys Gln Gln Val Gln Phe Asp Val Ile Pro Glu Ser Ala
                245                 250                 255

Pro Leu Asn Ile Pro Gly Leu Gly Arg Phe Ser Gly Leu Lys Thr Ser
            260                 265                 270

Val Phe Leu Glu Val Glu Gly Ala Ala His Tyr Leu Pro Ala Tyr Ala
            275                 280                 285

Gly Asn Leu Asp Ile Met Thr Ser Ala Ala Leu Ala Thr Ala Glu Arg
    290                 295                 300

Met Ala Gln Ser Met Leu Asn Ala
305                 310
```

GENETICALLY ENGINEERED YEAST CELL PRODUCING LACTATE INCLUDING ACETALDEHYDE DEHYDROGENASE, METHOD OF PRODUCING YEAST CELL, AND METHOD OF PRODUCING LACTATE USING THE SAME

RELATED APPLICATIONS

This application claims the benefits of Korean Patent Application No. 10-2013-0139320, filed on Nov. 15, 2013, and Korean Patent Application No. 10-2014-0115688, filed on Sep. 1, 2014, the entire disclosures of which are hereby incorporated by reference.

INCORPORATION BY REFERENCE OF ELECTRONICALLY SUBMITTED MATERIALS

Incorporated by reference in its entirety herein is a computer-readable nucleotide/amino acid sequence listing submitted herewith and identified as follows: 124,251 bytes (Text) file named "716905_ST25_Revised2" created Nov. 10, 2016.

BACKGROUND

1. Field

The present disclosure relates to a genetically engineered yeast cell capable of producing lactate, a method of preparing the same, and a method of producing lactate using the yeast cell.

2. Description of the Related Art

Lactate is an organic acid which is widely used in various industrial fields such as food, pharmaceutical, chemical, and electronic industries. Lactate is a colorless, odorless, and highly water-soluble substance having low volatility. As lactate is nontoxic to the human body, lactate is used as a flavoring agent, an acidifier, and a preservative. In addition, lactate is a raw material of polylactic acid (PLA), which is an environment-friendly alternative polymer substance and a biodegradable plastic. PLA is technically a polyester resin formed by converting lactate into lactide, which is a dimer, for polymerization and performing a ring-open polymerization with the lactide. PLA may be processed into various forms such as a film, a sheet, a fiber, and an injection molding product. Therefore, as PLA is a bio-plastic which may extensively be substituted for conventional general-purpose petrochemical plastics such as polyethylene (PE), polypropylene (PP), polyethylene terephthalate (PET), and polystyrene (PS), the demand for PLA has greatly increased in recent times. In addition, lactate has both a hydroxyl group and a carboxyl group and thus is highly reactive. Thus, lactate may be easily converted to industrially important compounds such as ester of lactate, acetaldehyde, and propylene glycol. Therefore, lactate is drawing attention in the field of chemical engineering as a next-generation alternative chemical raw material.

At present, lactate is industrially produced by a petrochemical synthetic process and a biological fermentative process. In the petrochemical synthetic process, lactate is prepared by oxidizing ethylene derived from crude oil, converting the resulting acetaldehyde to lactonitrile by an addition reaction of hydrogen cyanide, purifying the resulting lactonitrile by distillation, and hydrolyzing the purified lactonitrile by using hydrochloric acid or sulfuric acid. In the biological fermentative process, lactate may be prepared by using as substrate renewable carbohydrates such as starch, sucrose, maltose, glucose, fructose, and xylose. Therefore, according to the conventional technologies, a strain capable of efficiently producing lactate and a method of producing lactate using the same are needed. In accordance with the need, a method of producing lactate by using a microorganism has been recently developed. However, due to homeostasis of the microorganism, it is difficult that the microorganism may produce only one substance in large quantities. In the procedures for addressing these problems, the inventive concept was completed.

SUMMARY

An aspect of the present invention provides a genetically engineered yeast cell capable of effectively producing lactate. The genetically engineered yeast cell comprises an enzyme that catalyzes conversion of acetaldehyde to acetyl-CoA, and an enzyme that catalyzes conversion of pyruvate to lactate, wherein the activity of converting acetaldehyde to acetyl-CoA and converting pyruvate to lactate is increased in the genetically engineered yeast cell as compared to a parent cell.

Another aspect of the present invention provides a method of producing the genetically engineered yeast cell capable of effectively producing lactate, the method comprising introducing into a yeast cell a gene that encodes an enzyme that catalyzes conversion of acetaldehyde to acetyl-CoA, and a gene that encodes an enzyme that catalyzes conversion of pyruvate to lactate; and disrupting in the yeast cell a gene that encodes an enzyme that catalyzes conversion of acetaldehyde to ethanol.

Another aspect of the present invention provides a method of producing lactate using the genetically engineered yeast cell by culturing the genetically engineered yeast cell to produce lactate; and recovering the lactate from a culture product.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
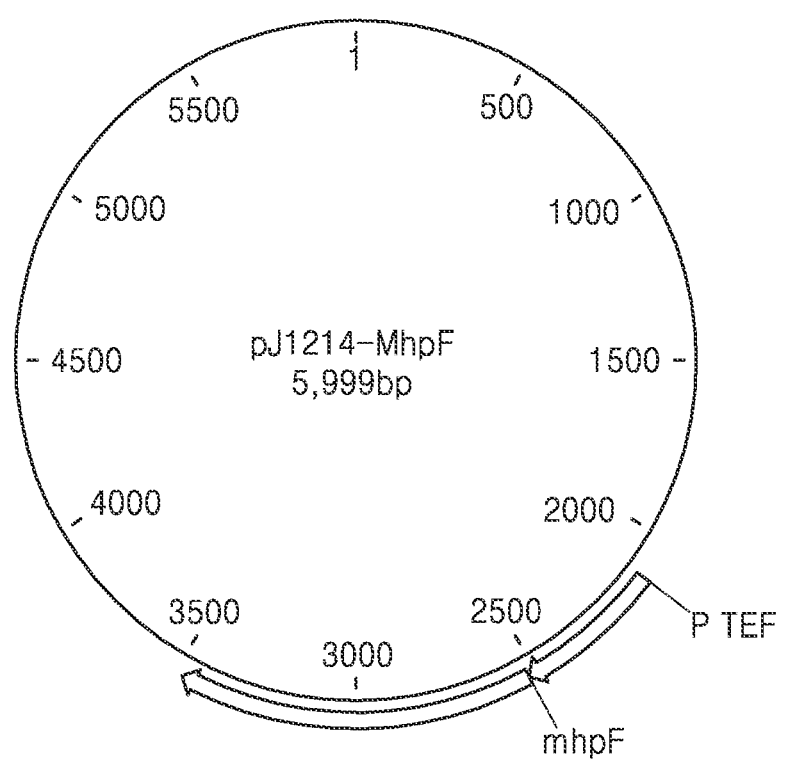
FIG. 1 shows a cleavage map of pJ1214-mhpF vector.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

Terms "increase in activity", or "increased activity" or the like as used herein may refer to a detectable increase in activity of a cell, a protein, or an enzyme. The terms "increase in activity", or "increased activity" used herein may mean that a modified (for example, genetically engineered) cell, protein, or enzyme shows higher activity than a comparable cell, protein, or enzyme of the same type, such as a cell, a protein, or an enzyme which does not have a particular genetic modification (e.g., an original or "wild-type" cell, protein, or enzyme, or the activity level of a parent cell or a protein or enzyme of a parent cell that served as the starting point for genetic modification). For example, activity of a modified or engineered cell, protein, or enzyme may be higher than activity of a non-engineered cell, protein, or enzyme of the same type (e.g., a wild-type cell, protein, or enzyme, or a the activity exhibited by a protein or enzyme of a parent cell) by about 5% or more, about 10% or more, about 15% or more, about 20% or more, about 30% or more, about 50% or more, about 60% or more, about 70% or more, or about 100% or more. A cell having a protein or enzyme having an increased enzymatic activity may be verified by any methods known in this art. The cell with increased activity may have one or more genetic modifications that increase an activity of an enzyme or a polypeptide compared to a cell that does not have the genetic modification(s).

Terms "decrease in activity" or "decreased activity" or the like as used herein may refer to a detectable decrease in the activity of a cell, protein, or enzyme. The terms "decrease in activity", or "decreased activity" used herein may mean that a modified (for example, genetically engineered) cell, protein, or enzyme shows lower activity than a comparable cell, protein, or enzyme of the same type, such as a cell, a protein, or an enzyme which does not have a particular genetic modification (e.g., an original or "wild-type" cell, protein, or enzyme, or the activity level of a parent cell or a protein or enzyme of a parent cell that served as the starting point for genetic modification). Thus, "decrease in activity" or "decreased activity" includes a case in which a genetically engineered cell contains an modified enzyme or polypeptide with activity that is lower than the activity of the same type of enzyme or polypeptide in a wild-type cell or parent cell, which does not contain the particular genetic modification. The terms "decrease in activity" or "decreased activity" also includes a case in which activity of separated (isolated) enzyme or polypeptide is lower than that of original or wild-type enzyme or polypeptide. The terms "decrease in activity" or "decrease in activity" includes the substantial or complete elimination of activity, such as when a cell has been genetically engineered to delete a sequence encoding an enzyme. In some embodiments, the activity of a modified (for example, genetically engineered) cell, protein, or enzyme (e.g., conversion activity from a substrate to a product) can be lower than that of non-modified cell or enzyme (e.g., a parent cell or "wild-type" cell or enzyme) by about 20% or more, about 30% or more, about 40% or more, about 50% or more, about 55% or more, about 60% or more, about 70% or more, about 75% or more, about 80% or more, about 85% or more, about 90% or more, about 95% or more, or about 100%. The decrease in activity in an enzyme or a cell may be verified by using any methods that are known in the art.

The term "parent cell" used herein refers to a cell prior to a particular genetic modification (e.g., an "original" cell). For example, in the case of an engineered yeast cell, a yeast cell before being genetically engineered. The "parent cell" is a cell that does not have a particular genetic modification but, in other aspects, the parent cell may be identical to a genetically engineered cell of the same type. Accordingly, the parent cell may be a cell that is used as a starting material for the production of a genetically engineered cell, such as a yeast cell having increased or decreased activity of a particular protein or enzyme.

The terms "disruption," "disrupted," and the like used herein refers to reduced expression of a given gene due to a genetic modification. Disruption can be caused by a genetic modification that inhibits expression of a referenced gene (hereinafter, referred to as "inactivation" of a gene.) Disruption includes a genetic modification that causes expression of a gene at decreased levels without completely inhibiting expression (hereinafter, referred to as "attenuation" of a gene.) Expression, in this sense, refers to transcription of a gene product as well as translation of an active gene product. Thus, inactivation of a gene includes a case in which a gene is not transcribed or translated, such that the protein product of the gene is not expressed, and a case in which although a gene is transcribed and translated, the gene product is not functional. Similarly, attenuation includes a case in which transcription or translation of a gene is reduced, as well as a case in which transcription or translation is not reduced, but the gene product has a lower activity level. Herein, the term "a functional product of a gene" means that the gene product (e.g., protein or enzyme) of a parent cell or wild-type cell has a biochemical or physiologic function (for example, enzyme activity). The disruption of the gene includes a functional disruption of the gene.

Genetic modification includes a modification that introduces a polynucleotide encoding a polypeptide into a cell; a modification that substitutes, adds (inserts), or deletes of one or more nucleotides of the genetic material of a parent cell; and chemical modification (exposure to a chemical) resulting in a change to the genetic material of a parent cell. Genetic modification includes a heterologous or homologous modification of referenced species. Genetic modification includes a modification of a coding region for polypeptides. Genetic modification also includes modification of non-coding regulatory regions that change expression of a gene or function of an operon. Non coding regions include 5'-non coding sequences (5' of a coding sequence) and 3'-non coding sequences (3' of a coding sequence).

The disruption of a gene may be achieved by a genetic engineering method, such as homologous recombination, directed mutagenesis, or directed molecular evolution. When a cell includes a plurality of identical genes or 2 or more paralogs of a gene, one or more genes may be disrupted. For example, the genetic modification may involve transforming a cell with a vector including the sequence of a gene, and then culturing the cell to cause a homologous recombination of the exogenous nucleic acid sequence and an endogenous gene of the cell, thereby disrupting the endogenous gene. The cell that has undergone homologous recombination can be screened out (selected) by using a selective marker.

The term "gene" used herein refers to a nucleic acid fragment that encodes a particular protein, which may optionally include at least one regulatory sequence, such as a 5'-non-coding sequence and a 3'-non-coding sequence (3' and 5' in reference to the position relative to the coding sequence).

The term "sequence identity" of a nucleic acid or polypeptide used herein refers to a degree of identity of bases or amino acid residues of two corresponding sequences over a particular region measured after the sequences are aligned to be matched with each other as much as possible. The sequence identity is a value that is measured by comparing optimally aligned two corresponding sequences of a particular comparable region, wherein in the comparable region, a part of the sequence may be added or deleted compared to a reference sequence. In some embodiments, a percentage of the sequence identity may be calculated by comparing two optimally aligned corresponding sequences in an entire comparable region, determining the number of locations where an amino acid or a nucleic acid is identical in the two sequences to obtain the number of matched locations, dividing the number of the matched locations by the total number (that is, a range size) of all locations within a comparable range, and multiplying the result by 100 to obtain a percentage of the sequence identity. The percent of the sequence identity may be determined by using known sequence comparison programs, examples of which include BLASTN and BLASTP (NCBI), CLC Main Workbench (CLC bio.), MegAlign™ (DNASTAR Inc).

In identifying polypeptides or polynucleotides of different species that may have identical or similar function or activity, similarity in sequence identity may be used. For example, similar sequences may have a sequence identity of 50% or more, 55% or more, 60% or more, 65% or more, 70% or more, 75% or more, 80% or more, 85% or more, 90% or more, 95% or more, 96% or more, 97% or more, 98% or more, 99% or more, or 100%.

The term "exogenous" and the like used herein refers to introduction of a referenced molecule (e.g., nucleic acid) or referenced activity into a host cell. A nucleic acid may be exogenously introduced into a host in any suitable manner. For example, a nucleic acid can be introduced into a host cell and inserted into a host chromosome, or the nucleic acid can be introduced into the host as non-chromosomal genetic material, such as a vector (e.g., a plasmid) that does not integrate into the host chromosome. A nucleic acid encoding a protein should be introduced in an expressionable form (i.e., so that the nucleic acid can be transcribed and translated). An exogenous "activity" (e.g., biosynthesis activity) refers to an activity introduced into a host parent cell, such as by introducing one or more nucleic acids of the host that are expressed to provide the activity.

The term "endogenous" refers to a referenced molecule (e.g., nucleic acid) or activity already present in the host cell prior to a particular genetic modification (e.g., a genetic composition, trait, or biosynthetic activity of a "wild-type" cell or a parent cell).

The term "heterologous" refers to molecule (e.g., nucleic acid) or activity derived from a source other than referenced species; and the term "homologous" refers to a molecule (e.g., nucleic acid) or activity derived from a host parent cell. Accordingly, an exogenous molecule or activity (e.g., expression of an exogenous coding nucleic acid) may be heterologous (e.g., a coding nucleic acid from a different species) or homologous (e.g., an additional copy of a coding nucleic acid from the same species) or both.

The term "genetic engineering" used herein refers to an act of introducing one or more genetic modifications into a cell, and the term "genetically engineered" refers to a protein or enzyme that has a non-naturally occurring sequence or a cell having a non-natural genetic composition.

The term "lactate" used herein refers to lactic acid or a salt thereof.

Provided is a genetically engineered yeast cell having lactate production capacity. Compared to a parent cell of the genetically engineered yeast cell, the activity of an enzyme catalyzing conversion of acetaldehyde to acetyl-CoA and an activity of an enzyme catalyzing conversion from pyruvate to lactate are increased in the genetically engineered yeast cell. Thus, the genetically engineered yeast cell converts acetaldehyde to acetyl-CoA and converts pyruvate to lactate at a rate that is greater than that of a parent cell.

The enzyme that catalyzes conversion of acetaldehyde to acetyl-CoA may be an acylating acetaldehyde dehydrogenase (A-ALD) classified as EC 1.2.1.10. The enzyme also may be a part of bifunctional aldolase-dehydrogenase complex associated with 4-hydroxy-2-ketovalerate catabolism. A bifunctional enzyme like this catalyzes final two steps of a meta-cleavage pathway of catechol, which is an intermediate in various bacterial species in decomposition of phenol, toluene, naphthalene, biphenyl, and other aromatic compounds (Powlowski and Shingler (1994) Biodegradation 5, 219-236). First, 4-hydroxy-2-ketovalerate is converted into pyruvate and acetaldehyde by 4-hydroxy-2-ketovalerate aldolase, and then, acetaldehyde is converted into acetyl-CoA by A-ALD. The type of A-ALD may be, for example, DmpF of *Pseudomonas* sp. CF600 (KEGG entry: CAA43226; SEQ ID NO: 82) (Shingler et al (1992) J. Bacteriol. 174:71 1-24). MhpF protein (Ferrandez et al (1997) J. Bacteriol. 179:2573-2581, Genbank No: NP 414885; SEQ ID NO: 1) of *Escherichia coli* is a homologue with respect to DmpF. Another type of enzyme that catalyzes conversion of acetaldehyde to acetyl-CoA is a protein that catalyzes a reversible conversion between strictly or facultative anaerobic microorganism-derived acetyl-CoA and acetaldehyde, and does not have alcohol dehydrogenase activity. Examples of this type of protein are found in *Clostridium kluyveri* (Smith et al (1980) Arch. Biochem. biophys. 203:663-675). A-ALD is annotated to the genome of *Clostridium kluyveri* DSM 555 (Genbank No: EDK33116). Homologous protein AcdH was confirmed in the genome of *Lactobacillus plantarum* (Genbank No: NP_784141). Another example of this type of protein is the gene product of *Clostridium* beijerinckii NRRL B593 (Toth et al (1999) App. Environ. Microbiol. 65: 4973-4980, Genbank No: AAD31841). An example of A-ALD is *Escherichia coli* derived MhpF or a functional homologue thereof, for example, *Escherichia coli* and *S. typhimurium* derived EutE, (for example, an EutE gene having a nucleotide sequence of SEQ ID NO: 53 and an EutE protein having an amino acid sequence of SEQ ID NO: 54), or *Pseudomonas* sp. CF600-derived dmpF. A-ALD may have NAD(P)+dependency. A-ALD may have an activity catalyzing the following reaction:

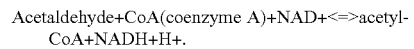

Acetaldehyde+CoA(coenzyme A)+NAD+<=>acetyl-CoA+NADH+H+.

The A-ALD may be an A-ALD capable of being expressed without formation of a complex with other proteins. In some embodiments, the yeast cell may not include an exogenous enzyme classified as EC 4.1.3.39 or a gene thereof.

A-ALD may be derived from *Escherichia coli*. The A-ALD gene in *Escherichia coli*, may be one of transcription units consisting of mhpA, mhpB, mhpC, mhpD, mhpE, and mhpF. In general, MhpE and MhpF exist as a complex in other microorganisms. However, MhpE and MhpF may exist independently in *Escherichia coli* and each one may show catalytic activity. The enzyme catalyzing the conversion of acetaldehyde to acetyl-CoA, for example, MhpF, may have 95% or greater sequence identity with the amino acid sequence of SEQ ID NO:1.

The genetically engineered yeast cell may include an exogenous gene that encodes the enzyme catalyzing the conversion of acetaldehyde to acetyl-CoA. The A-ALD exogenous gene may be expressed in the yeast cell in an amount sufficient to increase an activity of the enzyme catalyzing the conversion from acetaldehyde to acetyl-CoA as compared to a parent cell (e.g., a yeast cell without the exogenous gene). The A-ALD exogenous gene may encode an amino acid sequence that has 95% or more sequence identity with the amino acid sequence of SEQ ID NO: 1. The A-ALD exogenous gene may have a nucleotide sequence that has 95% or more sequence identity with nucleotide sequences of SEQ ID NO: 2 or SEQ ID NO: 3. SEQ ID NO: 2 is a nucleotide sequence of *Escherichia coli* derived A-ALD gene. A-ALD exogenous gene may be altered as appropriate for expression in a yeast cell (e.g., the sequence may be codon optimized for expression in yeast), provided the amino acid sequence of the encoded protein does not change. SEQ ID NO: 3 is an example of a *Escherichia coli*-derived A-ALD gene that has been codon optimized for expression in a yeast cell.

The exogenous gene may be introduced into a yeast cell via an expression vector. In some embodiments, the exogenous gene may be introduced in the form of a linear polynucleotide into a parent cell. In some embodiments, the exogenous gene may be expressed from an intracellular expression vector (for example, plasmid). In some embodiments, the exogenous gene may be, for stable expression, inserted into the intracellular genetic material of the cell (for example, chromosome) and expressed. In some embodiments, the exogenous gene may be appropriately regulated by an exogenous promoter that is operably linked to a gene. The promoter may be tdh3, adh1, ccw12, pdc1, tef1 or pgk1 gene-derived promoter.

In some embodiments, the enzyme catalyzing the conversion of pyruvate to lactate may be lactate dehydrogenase (LDH) classified as EC 1.1.2.27 or EC 1.1.1.28. LDH may have NAD(P)H-dependency. In some embodiments, LDH may act on D-lactate and/or L-lactate. LDH may have a 95% or more sequence identity with an amino acid sequence of SEQ ID NO: 6, which is LDH of *Pelodiscus sinensis japonicus*.

The yeast cell may include an exogenous gene that encodes the enzyme catalyzing the conversion of pyruvate to lactate. A LDH exogenous gene may be, in the yeast cell, expressed in an amount sufficient to increase activity of the enzyme catalyzing the conversion of pyruvate to lactate as compared to a parent cell. The LDH exogenous gene may encode an amino acid sequence that has 95% or more sequence identity with amino acid sequence of SEQ ID NO: 6. The LDH exogenous gene may have 95% or more sequence identity with a nucleotide sequence of SEQ ID NO: 7, which is a LDH gene of *Pelodiscus sinensis japonicus*. The sequence of the LDH exogenous gene may be codon optimized for expression in a yeast cell, provided that the amino acid sequence of the encoded protein does not change.

The LDH exogenous gene may code an enzyme that acts on at least one selected from L-lacate and D-lactate. Accordingly, the yeast cell may produce L-lactic acid or D-lactic acid, or a lacemic mixture or salt thereof.

The LDH exogenous gene may be derived from a bacteria, yeast, a fungus, and an animal, for example, a rodent, mammal, amphibian, or Sauropsida. The LDH exogenous gene may be a polynucleotide encoding LDH of one or more species selected from *Pelodiscus sinensis japonicus, Ornithorhynchus anatinus, Tursiops truncatus, Rattus norvegicus,* and *Xenopus laevis. Pelodiscus sinensis japonicus*-derived lactate dehydrogenase, *Ornithorhynchus anatinus*-derived lactate dehydrogenase, *Tursiops truncatus*-derived lactate dehydrogenase, and *Rattus norvegicus*-derived lactate dehydrogenase may have amino acid sequences of SEQ ID NOS: 6, 37, 38, and 39, respectively. The lactate dehydrogenase may have a sequence identity of 75% or more, 80% or more, 85% or more, 90% or more, 95% or more, 96% or more, 97% or more, 98% or more, or 99% or more, or 100%, with respect to the amino acid sequences of SEQ ID NOS: 6, 37, 38, and 39. A gene coding the lactate dehydrogenase may have a sequence identity of 75% or more, 80% or more, 85% or more, 90% or more, 95% or more, 96% or more, 97% or more, 98% or more, 99% or more, or 100%, with respect to the nucleotide sequences of SEQ ID NO: 7, 40, 41, or 42.

The LDH exogenous gene may be introduced into the genome of a cell, either as part of a chromosome in the cell or as an expression vector. The LDH exogenous gene may be expressed from a vector including the same. The vector may include a replication origin, a promoter, polynucleotide coding LDH, and a terminator. The replication origin may include a yeast autonomous replication sequence (ARS). The yeast autonomous replication sequence may be stabilized by a yeast centrometric sequence (CEN). The promoter may be selected from the group consisting of a CCW12 promoter, a CYC promoter, a TEF1 promoter, a PGK1 promoter, a GPD promoter, and a ADH promoter. The CCW12 promoter, the CYC promoter, the TEF1 promoter, the PGK1 promoter, the GPD promoter, and the ADH promoter may have nucleotide sequences of SEQ ID NOS: 9, 43, 11, 12, 44, and 45, respectively. The terminator may be selected from the group consisting of PGK1 (phosphoglycerate kinase 1), CYC1 (cytochrome c transcription), and GAL1. The CYC1 terminator may have a nucleotide sequence of SEQ ID NO: 46. The vector may further include a selective marker.

The yeast cell may include a single LDH gene, or a plurality of LDH genes, for example, 2 to 10 copies of an LDH gene. The yeast cell may include, for example, 1 to 10, 1 to 8, 1 to 7, 1 to 6, 1 to 5, 1 to 4, 1 to 3, 2 to 10, 2 to 8, 2 to 7, 2 to 6, 2 to 5, 2 to 4, or 2 to 3 copies of an LDH gene. When the yeast cell includes a plurality of LDH genes, each gene may include copies of identical gene or two or more different LDH genes. A plurality of copies of exogenous LDH genes may be included in identical gene loci, or various different gene loci in the chromosome of a host cell; in one or more different expression vectors; or a combination thereof.

In some embodiments, in the yeast cell, one or more genes selected from endogenous PDC genes, CYB2 gene, GPD genes, GPP genes, and ALD genes may be substituted with one or more exogenous LDH genes.

In some embodiments, in the yeast cell, an activity of an enzyme catalyzing conversion of acetaldehyde to ethanol may be decreased compared to a parent cell. The enzyme catalyzing the conversion of acetaldehyde to ethanol may be alcohol dehygrogenase (ADH) classified as EC 1.1.1.1. Examples of ADH include ADH1, ADH2, ADH3, ADH4, ADH5, ADH6, and ADH7. The alcohol dehydrogenase may have NAD(H) or NADP(H) dependency. ADH1 gene and ADH1 protein may have a nucleotide sequence of SEQ ID NO: 55 and an amino acid sequence of SEQ ID NO: 56, respectively.

In the yeast cell, an endogenous gene that codes the enzyme catalyzing the conversion from acetaldehyde into ethanol may be disrupted. The gene in the genetically engineered yeast cell may be disrupted such that activity converting acetaldehyde into ethanol (e.g., activity of than ADH enzyme) in the genetically engineered yeast cell is decreased or eliminated compared to that of a parent cell.

In some embodiments, the genetically engineered yeast cell having lactate production capability, in which enzyme activity catalyzing the conversion of acetaldehyde to acetyl-CoA and enzyme activity catalyzing the conversion of pyruvate to lactate are increased compared to a parent cell, and enzyme activity catalyzing the conversion of acetaldehyde into ethanol is decreased compared to a parent cell.

The genetically engineered yeast cell may be an engineered cell of a species of *Saccharomyces* genus, *Candida* genus, *Schizosaccharomyces* genus, *Kluyveromyces* genus, *Pichia* genus, *Issachenkia* genus, or *Hansenula* genus. A species classified as *Saccharomyces* genus may be, for example, *S. cerevisiae*, *S. bayanus*, *S. boulardii*, *S. bulderi*, *S. cariocanus*, *S. cariocus*, *S. chevalieri*, *S. dairenensis*, *S. ellipsoideus*, *S. eubayanus*, *S. exiguus*, *S. florentinus*, *S. kluyveri*, *S. martiniae*, *S. monacensis*, *S. norbensis*, *S. paradoxus*, *S. pastorianus*, *S. spencerorum*, *S. turicensis*, *S. unisporus*, *S. uvarum*, or *S. zonatus*. A species classified as *Candida* genus may be, for example, *C. albicans*, *C. ascalaphidarum*, *C. amphixiae*, *C. antarctica*, *C. argentea*, *C. atlantica*, *C. atmosphaerica*, *C. blattae*, *C. bromeliacearum*, *C. carpophila*, *C. carvajalis*, *C. cerambycidarum*, *C. chauliodes*, *C. corydali*, *C. dosseyi*, *C. dubliniensis*, *C. ergatensis*, *C. fructus*, *C. glabrata*, *C. fermentati*, *C. guilliermondii*, *C. haemulonii*, *C. insectamens*, *C. insectorum*, *C. intermedia*, *C. jeffresii*, *C. kefyr*, *C. krusei*, *C. lusitaniae*, *C. lyxosophila*, *C. maltosa*, *C. marina*, *C. membranifaciens*, *C. milleri*, *C. oleophila*, *C. oregonensis*, *C. parapsilosis*, *C. quercitrusa*, *C. rugosa*, *C. sake*, *C. shehatea*, *C. temnochilae*, *C. tenuis*, *C. theae*, *C. tolerans*, *C. tropicalis*, *C. tsuchiyae*, *C. sinolaborantium*, *C. sojae*, *C. subhashii*, *C. viswanathii*, *C. utilis*, or *C. ubatubensis*. A species classified as *Schizosaccharomyces* genus may be, for example, *S. pombe*, *S. japonicus*, *S. octosporus*, or *S. cryophilus*. A species classified as *Kluyveromyces* genus may be, for example, *K. aestuarii*, *K. africanus*, *K. bacillisporus*, *K. blattae*, *K. dobzhanskii*, *K. hubeiensis*, *K. lactis*, *K. lodderae*, *K. marxianus*, *K. nonfermentans*, *K. piceae*, *K. sinensis*, *K. thermotolerans*, *K. waltii*, *K. wickerhamii*, or *K. yarrowii*. A species classified as *Pichia* genus may be, for example, *P. anomala*, *P. heedii*, *P. guilliermondii*, *P. kluyveri*, *P. membranifaciens*, *P. norvegensis*, *P. ohmeri*, *P. pastoris*, *P. methanolica*, or *P. subpelliculosa*. A species classified as *Issachenkia* genus may be, for example, *I. orientalis*. A species classified as *Hansenula* genus may be, for example, *H. subpelliculosa*, *H. anomala*, *H. polymorpha*, *H. holstii* Wick, or *H. capsulata* Wick.

In some embodiments, in the yeast cell, activity of an enzyme catalyzing conversion of pyruvate into acetaldehyde, an enzyme catalyzing conversion of lactate to pyruvate, an enzyme catalyzing conversion of dihydroxyacetone phosphate (DHAP) to glycerol-3-phosphate (G3P), an enzyme catalyzing conversion of glycerol-3-phosphate (G3P) to glycerol, an enzyme catalyzing conversion of acetaldehyde from acetate, or a combination thereof may be decreased as compared to a parent cell.

The enzyme catalyzing conversion of pyruvate to acetaldehyde is classified as EC 4.1.1.1; the enzyme catalyzing conversion of lactate to pyruvate is classified as EC 1.1.2.4 or EC 1.1.2.3; the enzyme catalyzing conversion of DHAP to G3P is classified as EC 1.1.1.8; the enzyme catalyzing conversion of glycerol-3-phosphate (G3P) to glycerol is classified as EC 3.1.3.21; and the enzyme catalyzing conversion of acetaldehyde to acetate is classified as EC 1.2.1.3, EC 1.2.1.4, or EC 1.2.1.5.

In the genetically engineered yeast cell, a gene that encodes the enzyme catalyzing conversion of pyruvate to acetaldehyde, a gene that encodes the enzyme catalyzing conversion of lactate to pyruvate, a gene that encodes the enzyme catalyzing conversion of dihydroxyacetone phosphate (DHAP) to glycerol-3-phosphate (G3P), a gene that codes the enzyme catalyzing conversion of glycerol-3-phosphate to glycerol, a gene that codes the enzyme catalyzing conversion of acetaldehyde to acetate, or a combination thereof, may be disrupted.

The enzyme catalyzing conversion of pyruvate into acetaldehyde may be pyruvate decarboxylase (PDC). PDC may have a sequence identity of 75% or more, 80% or more, 85% or more, 90% or more, 95% or more, 96% or more, 97% or more, 98% or more, 99% or more, or 100%, with respect to an amino acid sequence of SEQ ID NO: 47. PDC gene may have a sequence identity of 75% or more, 80% or more, 85% or more, 90% or more, 95% or more, 96% or more, 97% or more, 98% or more, 99% or more, or 100%, with respect to a nucleotide sequence of SEQ ID NO: 48. PDC may include PDC1 (SEQ ID NO: 48), PDC5, and PDC6. PDC may catalyze a conversion of pyruvate to acetaldehyde in anaerobic or aerobic conditions.

In the genetically engineered yeast cell, a PDC gene may be disrupted due to substitution with an LDH gene. Alternatively or in addition, one or more PDC genes may be attenuated or inactivated. In some embodiments, at least one selected from PDC1 gene, PDC5 gene, and PDC6 gene may be attenuated or inactivated in the genetically engineered yeast cell. For example, PDC1 gene, PDC5 gene, PDC6 gene, PDC1 gene and PDC5 gene, PDC1 gene and PDC6 gene, or PDC5 gene and PDC6 gene may be attenuated or inactivated.

The enzyme catalyzing the conversion of lactate to pyruvate may be lactate cytochrome-c oxidoreductase (CYB2). The enzyme catalyzing the conversion of lactate to pyruvate may have cytochrome c-dependency. CYB2 may be classified as EC 1.1.2.4 acting on D-lactate, or EC 1.1.2.3 acting on L-lactate. The enzyme catalyzing the conversion of lactate to pyruvate may have a sequence identity of 75% or more, 80% or more, 85% or more, 90% or more, 95% or more, 96% or more, 97% or more, 98% or more, 99% or more or 100%, with respect to the amino acid sequence of SEQ ID NO: 48. A gene that codes the enzyme catalyzing the conversion of lactate to pyruvate may have a sequence identity of 75% or more, 80% or more, 85% or more, 90% or more, 95% or more, 96% or more, 97% or more, 98% or more, 99% or more or 100%, with respect to the nucleotide sequence of SEQ ID NO: 49. The CYB2 gene may be disrupted by substitution with LDH gene.

The enzyme catalyzing the conversion of DHAP to G3P may be NAD-dependent glycerol-3-phosphate dehydrogenase (GPD). GPD may be an NAD+-dependent enzyme. An example of GPD may be cytosolic glycerol-3-phosphate dehydrogenase, which is an enzyme catalyzing reduction of dihydroxyacetone phosphate (DHAP) into glycerol-3-phosphate by oxidation of NADH into NAD+. GPD may be classified as EC 1.1.1.8. Examples of GPD include GPD1 and GPD2. GPD may have a sequence identity of 75% or more, 80% or more, 85% or more, 90% or more, 95% or more, 96% or more, 97% or more, 98% or more, 99% or more, or 100%, with respect to an amino acid sequence of SEQ ID NO: 51. A gene that codes GPD may have a sequence identity of 75% or more, 80% or more, 85% or more, 90% or more, 95% or more, 96% or more, 97% or more, 98% or more, 99% or more, or 100%, with respect to a nucleotide sequence of SEQ ID NO: 52. GPD gene may be disrupted by substitution with LDH gene.

The enzyme catalyzing the conversion from glycerol-3-phosphate to glycerol may be glycerol phosphate phosphatase (GPP). Examples of GPP include S. cerevisiae-derived GPP1 and GPP2. GPP may have a nucleotide sequence of SEQ ID NO: 57 and an amino acid sequence of SEQ ID NO: 58. GPP gene may be disrupted by substitution with LDH gene.

The enzyme catalyzing the conversion of acetaldehyde to acetate may be acetaldehyde dehydrogenase (ALD). ALD may have NAD(P)+ dependency. ALD may have a sequence identity of 75% or more, 80% or more, 85% or more, 90% or more, 95% or more, 96% or more, 97% or more, 98% or more, 99% or more, or 100%, with respect to an amino acid sequence of SEQ ID NO: 60. The ALD gene may have a sequence identity of 75% or more, 80% or more, 85% or more, 90% or more, 95% or more, 96% or more, 97% or more, 98% or more, 99% or more, or 100%, with respect to a nucleotide sequence of SEQ ID NO: 61. Examples of ALD include ALD6 (also referred to as ALD1), ALD2, ALD3, ALD4, and ALD5. In the genetically engineered yeast cell, an ALD gene may be disrupted by substitution with LDH gene. Alternatively or in addition, an ALD gene may be attenuated. In some embodiments, in the genetically engineered yeast cell, at least one selected from ALD6 gene, ALD2 gene, and ALD3 gene may be attenuated or inactivated.

Also provided herein is a method of producing the genetically engineered yeast cell described herein. The method includes introducing into a yeast cell a gene that encodes an enzyme that catalyzes conversion of acetaldehyde to acetyl-CoA, and a gene that encodes an enzyme that catalyzes conversion of pyruvate to lactate; and disrupting a gene that encodes an enzyme that catalyzes conversion of acetaldehyde to ethanol.

All aspects of the yeast cell, including the enzyme that catalyzes conversion of acetaldehyde to acetyl-CoA, enzyme that catalyzes conversion of pyruvate to lactate, and genes encoding the enzymes, are as described above in connection with the engineered yeast cell provided herein.

The gene that encodes the enzyme catalyzing the conversion of acetaldehyde to acetyl-CoA and the gene that encodes enzyme catalyzing conversion of pyruvate to lactate may be simultaneously introduced into the yeast cell (separately, in different vectors, or together in a single vector) or sequentially introduced into the yeast cell.

In some embodiments, the gene that encodes the enzyme catalyzing the conversion from acetaldehyde to acetyl-CoA and the gene that encodes the enzyme catalyzing the conversion from pyruvate to lactate may be separately introduced and one or both genes inserted into the endogenous genetic material (for example, chromosome) of a yeast cell. In this case, these genes may be inserted into one or more locations of a particular gene of an endogenous genetic material (for example, chromosome) of a yeast cell, disrupting the genes. The particular gene may include a gene that encodes an enzyme catalyzing conversion of pyruvate into acetaldehyde, a gene that encodes an enzyme catalyzing conversion of lactate to pyruvate, a gene that encodes an enzyme catalyzing the conversion of dihydroxyacetone phosphate (DHAP) to glycerol-3-phosphate (G3P), a gene that encodes an enzyme catalyzing conversion of glycerol-3-phosphate to glycerol, and/or a gene that encodes an enzyme catalyzing the conversion of acetaldehyde to ethanol. Examples of these particular genes include PDC, CYB2, GPD, GPP, and ADH genes. When the particular gene is ADH gene, these two steps, i.e., the step of converting acetaldehyde to acetyl-CoA and the step of converting pyruvate to lactate may be simultaneously performed.

The gene that encodes the enzyme catalyzing the conversion from acetaldehyde to acetyl-CoA and the gene that encodes the enzyme catalyzing the conversion from pyruvate to lactate may be inserted into a single location of the endogenous genetic material (e.g., chromosome) of the yeast cell, or at different locations of the endogenous genetic material of the yeast cell. In other embodiments, one or both genes may be present in the yeast cell without being inserted into the endogenous genetic material (e.g., chromosome) of the yeast cell. In this case, the genes may be included in a vector, such as a plasmid, and expressed separately from the endogenous genetic material of the yeast cell.

The gene that encodes the enzyme catalyzing the conversion from acetaldehyde to acetyl-CoA and the gene that encodes the enzyme catalyzing the conversion from pyruvate to lactate may be introduced into the yeast cell in an expressionable form so that their respective gene products (enzyme catalyzing the conversion of acetaldehyde to acetyl-CoA, and enzyme catalyzing the conversion of pyruvate to lactate) are expressed in the yeast cell. The expressionable form may include the genes operably linked to expression regulatory sequences. For example, the genes (together or separately) may be operably linked to at least one selected from an exogenous enhancer, an operator, a promoter, and a transcription terminator, and thus are expressionable in a yeast cell by themselves. Alternatively, one or both genes may be linked to a regulatory sequence endogenous to the yeast cell to be expressionable (e.g., inserted at a point in the chromosome so as to be operably linked to a chromosomal regulatory element of the yeast).

The promoter may be selected from CCW12 promoter, CYC promoter, TEF1 promoter, PGK1 promoter, GPD promoter, and ADH promoter. The CCW12 promoter, CYC promoter, TEF1 promoter, PGK1 promoter, GPD promoter, and ADH promoter may have nucleotide sequences of SEQ ID NO: 9, 43, 11, 12, 44, and 45, respectively. The terminator may be selected from PGK1 (phosphoglycerate kinase 1), CYC1 (cytochrome c transcription), and GAL1. CYC1 terminator may have a nucleotide sequence of SEQ ID NO: 46. The vector may further include a selective marker.

Any known method of introducing a genetic material into a yeast cell may be used in the method provided herein (R. Danile Gietz et al., Biotechniques 30:816-831, April 2001). For example, the genes may be introduced by a spheroplast method, intact yeast cell transformation, electroporation, or a combination thereof. In an embodiment of intact yeast cell transformation, PEG may be used in combination with a particular monovalent alkali cation (Na+, K+, Rb+, Cs+ and Li+) to promote uptaking of DNA, such as plasmid, by a yeast cell. For example, an aqueous solution containing PEG, LiAc, carrier ssDNA, plasmid DNA, and the yeast cell may be heat shocked. In an embodiment of electroporation, an electric pulse is provided to a DNA-containing mixed medium that includes a yeast cell and plasmid DNA.

Accordingly, introducing the genes into the yeast cell may include contacting the yeast cell with the genes (together or separately in any order) in an appropriate liquid medium. The yeast cell may be spheroplast, or an intact yeast cell. The liquid medium may vary according to a selected transformation method. The liquid medium may be, for example, water, an aqueous solution, or a buffer. The aqueous medium may include a monovalent alkali cation (at least one selected from Na+, K+, Rb+, Cs+ and Li+), and PEG. The liquid medium may be carrier ssDNA. The liquid medium may be an aqueous solution that contains PEG, LiAc, and carrier ssDNA.

The contacting may be performed by heat shock or application of electric pulse. The heat shock method may include culturing at a temperature of about 40° C. to about 45° C., for example, about 42° C. The electric pulse, when used, may be applied between electrodes in an electroporation cuvette or a petri dish. Variables of the electric pulse, such as field strength (kV/cm), capacitance (uF), and resistance, may vary according to a particular condition of cell preparation. Transformation efficiency may vary according to yeast strain. For a given yeast strain, one of ordinary skill in the art may search for variables of pulse depending on a cell and select appropriate variables to obtain a desired number of transformants.

When insertion into the yeast cell endogenous genetic material (e.g., chromosome) is desired, the genes (together or separately, in any order) may be introduced into the yeast cell in a vector that includes a sequence homologous to the target region of the endogenous genetic material of the yeast cell. The term "homologous recombination" refers to a type of genetic recombination in which nucleotide sequences are exchanged between two similar or identical molecules of DNA. As used herein with reference to "homologous recombination," a "homologous sequence" is a sequence sufficiently complementary to a target sequence to facilitate homologous recombination (e.g., at least 95%, 98%, or 100% complementary). The homologous sequences in the vector are, therefore, sufficiently complementary to the target sequence present in the endogenous genetic material of the yeast cell to facilitate homologous recombination between the vector and the target sequence, whereby the target sequence may be substituted with the gene(s) from the vector.

The target sequence may include a gene that is to be disrupted (e.g., deleted). In one embodiment, the target sequence encodes an enzyme catalyzing conversion of pyruvate to acetaldehyde, a gene that encodes an enzyme catalyzing conversion of lactate to pyruvate, a gene that encodes an enzyme catalyzing conversion of dihydroxyacetone phosphate (DHAP) to glycerol-3-phosphate (G3P), a gene that encodes an enzyme catalyzing conversion of glycerol-3-phosphate to glycerol, or a gene that encodes an enzyme catalyzing conversion of acetaldehyde to ethanol. The method can involve the use of a combination of such target sequences. Examples of the target sequences include PCD, CYB2, GPD, GPP, and ADH gene. The vector may include two sequences (e.g., flanking the gene in the vector, optionally with linking sequences therebetween) which are homologous to the 5' end and 3' end of the target sequence, respectively. Such a vector can facilitate homologous recombination to substitute the target sequence with the gene(s) from the vector.

The method may include culturing the yeast cell under selection pressure during or after contacting the yeast cell with the gene(s) (or vector comprising the gene(s)). The selection pressure may employ a material or state that enables one to distinguish between a cell that undergoes homologous recombination and a cell that does not. For instance, the selection pressure may include culturing in the presence of antibiotics when used with a vector including, as a selection marker, a gene that encodes an enzyme that the antibiotics. Other selection markers (and selection conditions) are known in the art.

Disrupting the gene that encodes an enzyme catalyzing conversion of acetaldehyde to ethanol can be performed using any suitable technique. Disrupting the gene may include contacting, in an appropriate liquid medium, a yeast cell with a polynucleotide that has a homologous sequence to the gene that encodes the enzyme catalyzing conversion of acetaldehyde to ethanol. The homologous sequence may be entirely or partially homologous to the endogenous gene to be disrupted. The homologous sequence may be homologous to a coding region or expression regulatory region of the target gene. A polynucleotide having a homologous sequence to the gene may be linked to other genes, for example, a gene that codes an enzyme associated with promotion of lactate biosynthesis. Such a gene may be A-ALD gene or LDH gene. The polynucleotide having a homologous sequence to the gene may be included in a vector, such as plasmid. The homologous sequence may be used to substitute a gene that codes the enzyme catalyzing conversion of acetaldehyde to ethanol with a different gene by homologous recombination. The vector may include two sequences which are respectively homologous to the 5' end and 3' end of the target sequence.

Disrupting the gene may also include culturing the yeast cell under selection pressure during or after contacting the yeast cell with the homologous sequence. The selection pressure may employ a material or state that enables one to distinguish between a cell that undergoes homologous recombination and a cell that does not. For instance, the selection pressure may include culturing in the presence of antibiotics when used with a vector including, as a selection marker, a gene that encodes an enzyme that the antibiotics. Other selection markers (and selection conditions) are known in the art.

Unless stated otherwise, other aspects of the method of disrupting the gene are as described in connection with introducing the gene that encodes the enzyme catalyzing conversion of acetaldehyde to acetyl-CoA and the gene that encodes the enzyme catalyzing conversion of pyruvate to lactate into the yeast cell. Disrupting the gene that encodes an enzyme catalyzing conversion of acetaldehyde to ethanol and introducing the gene that encodes the enzyme catalyzing conversion of acetaldehyde to acetyl-CoA and the gene that encodes the enzyme catalyzing conversion of pyruvate to lactate may be performed simultaneously or sequentially in any order.

The method of producing the genetically engineered yeast that produces lactate may further include disrupting, in the yeast cell, a gene that encodes an enzyme catalyzing the conversion of pyruvate to acetaldehyde, a gene that encodes an enzyme catalyzing the conversion of lactate to pyruvate, a gene that encodes an enzyme catalyzing the conversion of dihydroxyacetone phosphate to glycerol-3-phosphate, a gene that encodes an enzyme catalyzing the conversion of glycerol-3-phosphate to glycerol, or a combination thereof. Herein, descriptions of "a gene that codes an enzyme catalyzing the conversion from pyruvate to acetaldehyde", "a gene that codes an enzyme catalyzing the conversion from lactate to pyruvate", "a gene that codes an enzyme catalyzing the conversion from dihydroxyacetone phosphate to glycerol-3-phosphate", and "a gene that codes an enzyme catalyzing the conversion from glycerol-3-phosphate to glycerol" are the same as described above with respect to the genetically engineered yeast.

Disrupting one or more of the above genes may include contacting a yeast cell with a polynucleotide having a sequence homologous to a region of the gene in an appropriate liquid medium so as to facilitate homologous recombination. The homologous sequence may be entirely or partially homologous to the at least one gene. The homologous sequence may be homologous to a portion or all of a coding region or expression regulatory region of the at least one gene.

A polynucleotide having a sequence homologous to the at least one gene may be linked to other genes that code an enzyme associated with promotion of lactate biosynthesis. Such a gene may be A-ALD gene or LDH gene. The polynucleotide having a sequence homologous to the gene may be included in a vector, such as plasmid. The homologous sequence may be used to substitute the at least one gene by homologous recombination. The vector may include two sequences (e.g., flanking a gene of interest, optionally with a linking sequence therebetween) which are homologous to the 5' end and 3' end of the target sequence, respectively.

Disrupting the gene may also include culturing the yeast cell under selection pressure during or after contacting the yeast cell with the homologous sequence. The selection pressure may employ a material or state that enables one to distinguish between a cell that undergoes homologous recombination and a cell that does not. For instance, the selection pressure may include culturing in the presence of antibiotics when used with a vector including, as a selection marker, a gene that encodes an enzyme that the antibiotics. Other selection markers (and selection conditions) are known in the art.

Unless stated otherwise, other aspects of disrupting the one or more above-described genes are as previously in connection with other aspects of the compositions and methods provided herein Also provided herein is a method of producing lactate, which method includes culturing the genetically engineered yeast cell to produce lactate; and recovering lactate from a culture product.

The culturing may be performed in a culture medium including a carbon source, for example, glucose. The medium used may be any medium appropriate for growth of a host cell, such as a minimal medium or a complex medium supplemented with an appropriate supplement. An appropriate medium may be obtained from a commercial seller or prepared by a known preparation method. The medium used in the culturing may be a medium capable of satisfying specific yeast cell requirements. The medium may be a medium selected from the group consisting of a carbon source, a nitrogen source, a salt, a trace element, and a combination thereof.

To obtain lactate from the genetically engineered yeast cell, the culturing conditions may be appropriately controlled. The cell may be cultured under aerobic conditions for growth. Then, for lactate production, the cell may be cultured under microaerobic conditions or anaerobic conditions. The term "anaerobic conditions" refers to an oxygen-free environment. The term "microaerobic conditions" as used herein to refer to culture or growth conditions means a concentration of dissolved oxygen (DO) in a medium greater than 0% and equal to or smaller than about 10% of saturation in a liquid medium. In some embodiments, microaerobic conditions include growing or resting a cell in a liquid medium or a solid agar plate in a sealed chamber in which less than 1% of oxygen atmosphere is maintained. The concentration of oxygen may be maintained by for example, sparging a culture product with $N^2/CO^2$ mixture or other appropriate non-oxygen material. Under the oxygen conditions, the dissolved oxygen (DO) concentration may be maintained from about 0% to about 10%, from about 0% to about 8%, from about 0% to about 6%, from about 0% to about 4%, or from about 0% to about 2%.

The term "culturing condition" refers to a condition for yeast cell culturing. The culturing condition may be, for example, a condition of a carbon source, a nitrogen source, or oxygen used by a yeast cell. A carbon source which may be used by a yeast cell includes a monosaccharide, a disaccharide, a polysaccharide, and others. The carbon source may be glucose, fructose, mannose, galactose or others may be used. A nitrogen source used by a yeast cell may be an organic nitrogen compound or a inorganic nitrogen compound. Examples of the nitrogen source are an amino acid, amide, amine, a nitrate, and an ammonium salt.

The culture product includes a cell and a medium used for the culture. Lactate may be separated from the culture product by common methods known in the related art. The separation method may be centrifugation, filtration, ion-exchange chromatography, or crystallization. For example, the culture product may be centrifuged at a low speed to remove biomass therefrom and the resulting supernatant may be separated by ion-exchange chromatography.

Hereinafter, embodiments of the inventive concept will be described in detail. However, these embodiments are presented herein for illustrative purpose only, and do not limit the scope of the inventive concept.

EXAMPLE 1 mhpF Gene and/or EutE Gene-Containing *S. Cerevisiae*

*S. cerevisiae* strain used in the following examples was prepared as described below.

(1) Preparation of MhpF Gene Expression Strain
(1.1) Preparation of *S. cerevisiae* CEN.PK2-1D(Δadh1:: ldh, mhpF)
(1.1.1) Preparation of pJ1214-MhpF Vector for Introducing MhpF Gene

*Escherichia coli* derived MhpF gene (SEQ ID NO: 2) was codon optimized for expression in *S. cerevisiae* to provide a synthesized MhpF gene (SEQ ID NO: 3) (DNA2.0 Inc., USA). The synthesized MhpF gene had a 5' end linked to TEF1 promoter sequence (SEQ ID NO: 11), so that TEF1 promoter regulates transcription. pJ1214-mhpF (DNA2.0 Inc., USA) including the synthesized TEF1 promoter-MhpF gene was prepared. pJ1214 (DNA2.0 Inc., USA) is an expression vector for *S. cerevisiae*, and includes URA3 marker and 2 um Ori sequence.

FIG. 1 shows a cleavage map of pJ1214-mhpF vector. Referring to FIG. 1, P TEF indicates a TEF1 promoter. A nucleotide sequence of pJ1214-mhpF vector is set forth in SEQ ID NO: 8.

(1.1.2) Production of adh1 Gene Deletion Cassette

To prepare 'ldh cassette'-containing vector, CCW12 gene promoter (hereinafter referred to as "P CCW12" or "CCW12 promoter") was amplified by PCR using *S. cerevisiae* CEN.PK2-1D genome DNA as a template, and a primer set of SEQ ID NOS: 13 and 14. The CCW12 gene promoter amplification product (SEQ ID NO: 9) and synthesized ldh gene (SEQ ID NO: 7) (DNA2.0 Inc., USA) were respectively cleaved by using SacI/XbaI and BamHI/SalI, and then linked to pRS416 vector (ATCC87521™) cleaved using the same enzyme. pRS416 vector is a yeast centromere shuttle plasmid that has a T7 promoter, ampicillin resistance in bacteria, URA3 cassette (selective marker) in yeast, and a restriction enzyme cloning site.

Figure 2:
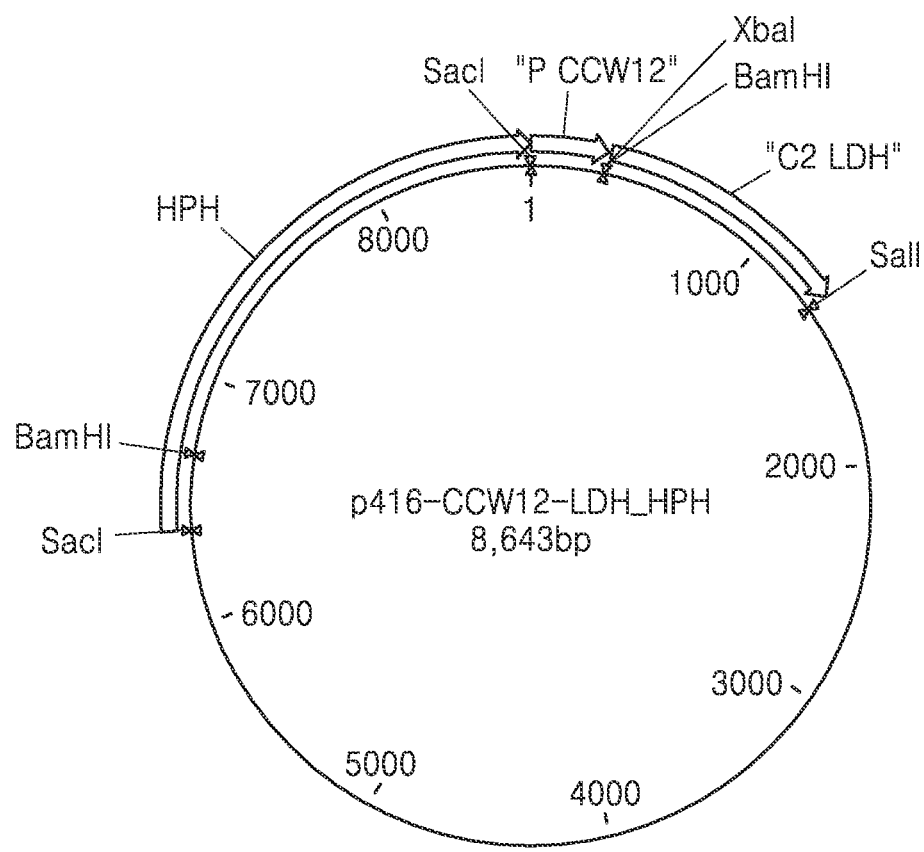
FIG. 2 shows a cleavage map of p416-ldh-HPH vector.

"HPH cassette" sequence (SEQ ID NO: 17) was amplified by PCR using pCEP4 plasmid (invitrogen, Cat. no. V044-50) as a template, and a primer set of SEQ ID NOS: 15 and 16. The amplified "HPH cassette" and the pRS416 vector were cleaved by using a SacI enzyme and then connected to each other to prepare vector p416-ldh-HPH in which 'ldh cassette' is operably linked to "HPH cassette". FIG. 2 shows a cleavage map of p416-ldh-HPH vector. Referring to FIG. 2, "P CCW12" and "C2 LDH" respectively indicate CCW12 promoter and LDH orf. pCEP4 plasmid is Episomal mammalian expression vector using cytomegalovirus (CMV) immediate early enhance/promoter for high-level transcription of recombined gene inserted into multiple cloning sites. pCEP4 has hygromycin B resistance gene for stable selection in transfected cell. Herein, 'ldh cassette' indicates a region that has a ldh gene and a regulatory region operably linked thereto, and thus enables expression of ldh gene. ldh gene is transcribed in the presence of CCW12 promoter. 'HPH (hygromycin B phosphotransferase) cassette' indicates a region that has hygromycin B resistance gene and a regulatory region operable linked thereto, and thus, enables expression of hygromycin B resistance gene.

An adh1 deletion cassette was prepared by PCR using p416-ldh-HPH vector as a template and a primer set of SEQ ID NO: 4 and SEQ ID NO: 5. In each of SEQ ID NO: 4 and SEQ ID NO: 5, the 1-50th positions of the sequence is homologous to a sequence of the S. cerevisiae genome so as to replace adh1 gene in S. cerevisiae CEN.PK2-1D genome by homologous recombination with ldh-HPH cassette, thereby inactivating adh1 and introducing ldh gene.

(1.1.3) Production of S. cerevisiae CEN.PK2-1D(Δadh1::ldh, mhpF)

To replace adh1 gene with ldh gene in S. cerevisiae CEN.PK2-1D, "adh1 deletion cassette" prepared in (1.1.2) was introduced into S. cerevisiae CEN.PK2-1D strain by heat shock transformation, and then cultured in 200 ug/mL of hygromycin-containing YPD medium (1 (w/v) & Yeast extract, 1 (w/v) & peptone, and 2 (w/v) & glucose) at a temperature of 30° C. for 3 days to replace adh1 gene with ldh gene in the yeast chromosome, thereby producing S. cerevisiae CEN.PK2-1D(Δadh1::ldh) strain.

pJ1214-mhpF vector for MhpF expression prepared in (1.1.1) was introduced to S. cerevisiae CEN.PK2-1D (Δadh1::ldh) strain by heat shock transformation to produce S. cerevisiae CEN.PK2-1D(Δadh1::ldh, mhpF) strain. In detail, after the strain was heat shocked, the result was cultured in a minimal Ura-drop out medium (6.7 g/L of Yeast nitrogen base without amino acids (Sigma-Aldrich: Cat. no. Y0626), and 1.9 g/L of Yeast synthetic drop-out without uracil (Sigma-Aldrich: Cat. no. Y1501), and 2 (w/v) % of glucose) at a temperature of 30° C. for 3 days. To analyze genotype of the prepared strain, the deletion of adh1 gene and the introduction of ldh gene were confirmed by PCR using the genome of the prepared strain as a template, and a primer set of SEQ ID NOS: 18 and 19, and the introduction of mhpF gene was confirmed by PCR using a primer set of SEQ ID NOS: 20 and 21.

It was confirmed that the prepared strain was S. cerevisiae CEN.PK2-1D(Δadh1::ldh, mhpF) strain.

(1.2) Production of Mutant Strain of S. cerevisiae CEN.PK24D(Δadh1::ldh, mhpF)

(1.2.1) Preparation of pdc1, cyb2, and gpd1 Deletion Vectors

A pyruvate decarboxylase1 (Pdc1) deletion cassette was prepared as follows: PCR was performed by using p416-ldh-HPH as a template and a primer set of SEQ ID NOS: 22 and 23 as a primer. An amplification product was cleaved using SacI, and then, linked to pUC57-Ura3HA vector (DNA2.0 Inc.: SEQ ID NO: 24) cleaved by using the same enzyme to prepare pUC57-ura3HA-ldh. PCR was performed using pUC57-ura3HA-ldh as a template and a primer set of SEQ ID NOS: 25 and 26, thereby completing the preparation of pdc1 deletion cassette. 1-42nd and 1-44th positions of sequences of SEQ ID NO: 25 and SEQ ID NO: 26 are homologous to a region of the S. cerevisiae chromosome so as to replace the endogenous pdc1 gene by homologous recombination.

L-lactate cytochrome-c oxidoreductase (cyb2) gene deletion cassette was amplified by PCR using pUC57-ura3HA-ldh deletion vector as a template and a primer set of SEQ ID NOS: 29 and 30. 1-45th positions of the sequence of each of SEQ ID NO: 29 and SEQ ID NO: 30 are homologous to a region of the S. cerevisiae chromosome so as to replace the endogenous cyb2 gene by homologous recombination.

Glycerol-3-phosphate dehydrogenase) (gpd1) gene deletion cassette was amplified by PCR using pUC57-ura3HA-ldh deletion vector as a template and a primer set of SEQ ID NOS: 33 and 34 as a primer. 1-50th positions of the sequence of SEQ ID NO: 34 are homologous to a region of the S. cerevisiae chromosome so as to replace the endogenous gpd1 gene by homologous recombination.

(1.2.2.) Preparation of Mutant Strain of S. cerevisiae CEN.PK2-1D (Δadh1::ldh, mhpF)

First, to substitute the endogenous pdc1 gene with a ldh gene from S. cerevisiae CEN.PK2-1D(Δadh1::ldh, mhpF), "pdc1 deletion cassette" prepared in (1.2.1) was introduced to S. cerevisiae CEN.PK2-1D (Δadh1::ldh, mhpF) prepared in (1.1) by heat shock transformation, and the strain was then cultured in Ura-drop out medium, which is a selective marker, at a temperature of 30° C. for 3 days to replace pdc1 gene in chromosome with ldh gene. To analyze the genotype of the prepared strain, the deletion of pdc1 gene was confirmed by PCR using the genome of the prepared strain as a template and a primer set of SEQ ID NOS: 27 and 28.

It was confirmed that the prepared strain was S. cerevisiae CEN.PK2-1D (Δadh1::ldh, mhpF, Δpdc1::ldh) strain.

To substitute cyb2 gene with ldh gene from S. cerevisiae CEN.PK2-1D (Δadh1::ldh, mhpF) strain, "cyb2 deletion cassette" prepared in (1.2.1) was introduced to the strain by heat shock transformation, and the strain was then cultured in Ura-drop out medium, which is a selective marker, at a temperature of 30° C. for 3 days to replace cyb2 gene in chromosome with ldh gene. To analyze the genotype of the prepared strain, the deletion of cyb2 gene was confirmed by PCR using the genome of the prepared strain as a template and a primer set of SEQ ID NOS: 31 and 32.

It was confirmed that the prepared strain was S. cerevisiae CEN.PK2-1D (Δadh1::ldh, mhpF, Δcyb2::ldh) strain.

Next, to substitute gpd1 gene with ldh gene from S. cerevisiae CEN.PK2-1D (Δadh1::ldh, mhpF) strain, "gpd1 deletion cassette" prepared in (1.2.1) was introduced to the strain by heat shock transformation, and the strain was then cultured in Ura-drop out medium, which is a selective marker, at a temperature of 30° C. for 3 days to replace gpd1 gene in chromosome with ldh gene. To analyze the genotype of the prepared strain, the deletion of gpd1 gene was confirmed by PCR using the genome of the prepared strain as a template and a primer set of SEQ ID NOS: 35 and 36.

It was confirmed that the prepared strain was S. cerevisiae CEN.PK2-1D (Δadh1::ldh, mhpF, Δgpd1::ldh) strain.

Next, to substitute cyb2 gene with ldh gene from S. cerevisiae CEN.PK2-1D (Δadh1::ldh, mhpF, Δpdc1::ldh) strain, "cyb2 deletion cassette" prepared in (1.2.1) was introduced to the strain by heat shock transformation, and after the heat shock, the result was cultured in Ura-drop out medium, which is a selective marker, at a temperature of 30° C. for 3 days to replace cyb2 gene in chromosome with ldh gene. To analyze the genotype of the prepared strain, the deletion of cyb2 gene was confirmed by PCR using the genome of the prepared strain as a template and a primer set of SEQ ID NOS: 31 and 32.

As a result, it was confirmed that the prepared strain was *S. cerevisiae* CEN.PK2-1D (Δadh1::ldh, mhpF, Δpdc1::ldh, Δcyb2::ldh) strain.

Next, to substitute gpd1 gene with ldh gene from *S. cerevisiae* CEN.PK2-1D (Δadh1::ldh, mhpF, Δpdc1::ldh, Δcyb2::ldh) strain, "gpd1 deletion cassette" prepared in (1.2.1) was introduced to the strain by heat shock transformation, and after the heat shock, the result was cultured in Minimal Ura-drop out medium, which is a selective marker, at a temperature of 30° C. for 3 days to replace gpd1 gene in chromosome with ldh gene. To analyze the genotype of the prepared strain, the deletion of gpd1 gene was confirmed by PCR using the genome of the prepared strain as a template and a primer set of SEQ ID NOS: 35 and 36.

As a result, it was confirmed that the prepared strain was *S. cerevisiae* CEN.PK2-1D (Δadh1::ldh, mhpF, Δcyb2::ldh, Δgpd1::ldh) strain.

(1.2.3) Preparation of Control Strain to which MhpF Gene was not Introduced

Control strain was prepared in the same manner as in (1.2.2.), except that the same starting strain was used and MhpF gene was not introduced. The list of control strain as follows:
*S. cerevisiae* CEN.PK2-1D(Δadh1::ldh, Δpdc1::ldh, Δcyb2::ldh, Δgpd1::ldh)
*S. cerevisiae* CEN.PK2-1D(Δadh1::ldh, Δpdc1::ldh, Δcyb2::ldh)
*S. cerevisiae* CEN.PK2-1D(Δadh1::ldh, Δpdc1::ldh, Δgpd1::ldh)
*S. cerevisiae* CEN.PK2-1D(Δadh1::ldh, Δcyb2::ldh, Δgpd1::ldh)
*S. cerevisiae* CEN.PK2-1D(Δadh1::ldh, Δpdc1::ldh)
*S. cerevisiae* CEN.PK2-1D(Δadh1::ldh, Δcyb2::ldh)
*S. cerevisiae* CEN.PK2-1D(Δadh1::ldh, Δgpd1::ldh)

(2) Preparation of mhpF and EutE Gene Expression Strain (2.1) Preparation of *S. cerevisiae* CEN.PK2-1D(Δpdc1::ldh, Δcyb2::ldh, Δgpd1::ldh, Δadh1::ldh, mhpF)

(2.1.1) Preparation and Introduction of Vector for Insertion of mhpF

MhpF gene was inserted to enhance a conversion pathway from acetaldehyde to acetyl-CoA in *S. cerevisiae* CEN.PK2-1D(Δpdc1::ldh, Δcyb2::ldh, Δgpd1::ldh, Δadh1::ldh).

MhpF gene of pJ1214-mhpF and 'HIS3 cassette' were each linked to 'pUC19 vector'(NEB, N3041) by using SalI restriction enzyme to prepare pUC19-His-MhpF vector (SEQ ID NO: 59). HIS3 cassette was an amplification product obtained by PCR using pRS413 (ATCC8758) as a template and a primer set of SEQ ID NO: 62 and SEQ ID NO: 63. In pUC19-His-MhpF vector, mhpF is expressed in the presence of GPD promoter.

An mhpF introduction cassette was obtained by PCR using pUC19-His-MhpF vector as a template, and a primer set of SEQ ID NOS: 64 and 65 to which leu2 homologous recombination sequence and promoter were linked. leu2 is a site that is mutated in a parent strain and, thus, does not express a functional protein.

(2.1.2) Preparation of *S. cerevisiae CEN.PK*2-1D(Δpdc1::ldh, Δcyb2::ldh, Δgpd1::ldh, Δadh1::ldh, mhpF)

mhpF insertion cassette prepared in (2.1.1) was introduced to *S. cerevisiae* CEN.PK2-1D(Δpdc1::ldh, Δcyb2::ldh, Δgpd1::ldh, Δadh1::ldh). The introduction was performed by heat shock transformation, and after transduction, cells were cultured in a histidine drop out medium (6.7 g/L of Yeast nitrogen base without amino acids (Sigma-Aldrich: Cat. no. Y0626), and 1.9 g/L of Yeast synthetic drop-out without histidine (Sigma-Aldrich: Cat. no. Y1751), and 2 (w/v) % of glucose) to replace Leu2 ORF on chromosome with the cassette.

To verify the introduction of mhpF gene to Leu2 locus in the obtained strain, gene deletion and gene introduction were confirmed by PCR using the cell genome as a template and a primer set of SEQ ID NOS: 66 and 77. The strain was confirmed to be *S. cerevisiae* CEN.PK2-1D(Δpdc1::ldh, Δcyb2::ldh, Δgpd1::ldh, Δadh1::ldh, mhpF).

(2.2) Preparation of *S. cerevisiae* CEN.PK2-1D(Δpdc1::ldh, Δcyb2::ldh, Δgpd1::ldh, Δadh1::ldh, mhpF, Δald6)

(2.2.1) Preparation and Introduction of Vector for Deletion of ald6

Acetaldehyde dehydrogenase 6 (ald6) gene deletion cassette was amplified by PCR using pUC57-ura3HA deletion vector as a template and a primer set of SEQ ID NOS: 68 and 69 as a primer. The sequences of SEQ ID NOS: 68 and 69 include a site that is to be replaced with ald6 gene by recombination with a homologous sequence of chromosome of *S. cerevisiae*.

(2.2.2) Preparation of *S. cerevisiae CEN.PK*2-1D(Δpdc1::ldh, Δcyb2::ldh, Δgpd1::ldh, Δadh1::ldh, mhpF, Δald6) strain To delete ald6 gene from *S. cerevisiae* CEN.PK2-1D (Δadh1::ldh, mhpF, Δpdc1:ldh, Δcyb2:ldh, Δgpd1:ldh) strain, "ald6 deletion cassette" prepared in (2.2.1) was introduced to the strain by heat shock transformation, and after the heat shock, the result was cultured in Minimal Ura-drop out medium, which is a selective marker, at a temperature of 30° C. for 3 days to delete ald6 gene in chromosome. To analyze the genotype of the prepared strain, the deletion of ald6 gene was confirmed by PCR using the genome of the prepared strain as a template and a primer set of SEQ ID NOS: 70 and 71.

It was confirmed that the prepared strain was *S. cerevisiae* CEN.PK2-1D(Δadh1::ldh, mhpF, Δpdc1:ldh, Δcyb2:ldh, Δgpd1:ldh, Δald6).

(2.3) Preparation of *S. Cerevisiae CEN.PK*2-1D(Δpdc1::ldh, Δcyb2::ldh, Δgpd1::ldh, Δadh1::ldh, mhpF, Δald6, EutE)

(2.3.1) Preparation and Introduction of EutE Introduction Vector (2.3.1.1). Preparation of Enzyme Dual Function Overexpression Vector pCS-Ex1

689 bp of DNA fragment (GPD promoter) was obtained from pRS426GPD vector, which is widely used as a yeast overexpression vector, by PCR using a primer combination of SEQ ID NO: 72 and SEQ ID NO: 73. The DNA fragment was mixed with pCtB1 vector (Genbank Accession Number KJ922019) treated with KpnI, cloned by using In-fusion kit (Clonetech, cat. 639650), and then, introduced to TOP10 strain (Invitrogen, cat. C4040-06), which is an *Escherichia coli* strain for cloning. After the introduction, the strain was smeared on LB agar medium (10 g/L of Bacto Tryptone, 5 g/L of Yeast Extract, 10 g/L of NaCl, and 15 g/L of Bacto Agar) containing 50 ug/ml of kanamycin, and then cultured to form colonies. From among the colonies, plasmid DNA was separated, and the presence of a plasmid sequence of SEQ ID NO: 74 was confirmed. As a result, a pCS-Ex1 vector, which is a yeast dual function overexpression vector, was obtained. Herein, the term "dual function" indicates a function of gene expression after a gene is inserted into genome and a function of gene expression in vector.

(2.3.1.2) Preparation of Yeast Dual Function *Escherichia coli* eutE Gene Overexpression Vector 1447 bp of DNA fragment, that is, EutE gene was obtained from genome DNA of *Escherichia coli* MG1655 strain by PCR using a primer combination of SEQ ID NO: 75 and SEQ ID NO: B76. The DNA fragment was mixed with pCS-Ex1 vector treated with KpnI and SacI, cloned by using In-fusion kit (Clontech cat. 639650), and then introduced to TOP10 strain (Invitrogen cat. C4040-06), which is *Escherichia coli* strain for cloning. After the introduction, the strain was smeared on a LB agar medium containing 50 ug/ml of kanamycin, and cultured to form colonies. From among the colonies, plasmid DNA was separated and the presence of plasmid sequence of SEQ ID NO: 77 was confirmed. As a result, MD1040 vector, which is a yeast dual function *Escherichia coli* eutE gene overexpression vector, was obtained.

(2.3.2) Preparation of Yeast Having Overexpressed *Escherichia coli* eutE Gene

From the prepared MD1040 vector, 3985 bp of DNA fragment was obtained by PCR using a primer combination of SEQ ID NO: 78 and SEQ ID NO: 89. This fragment was introduced to *S. cerevisiae* CEN.PK2-1D(Δpdc1::ldh, Δcyb2::ldh, Δgpd1::ldh, Δadh1::ldh, mhpF, Δald6), and then smeared on SD-URA agar medium [6.7 g/L of Yeast nitrogen base without amino acids (Sigma-Aldrich: Cat. no. Y0626), 1.9 g/L of Yeast synthetic drop-out without uracil (Sigma-Aldrich: Cat. no. Y1501), 20 g/L of D-glucose, and 20 g/L of Bacto Agar], which is a uracil-free minimal medium. From among colonies formed from the fourth day after the smearing, a colony in which 4357 bp of DNA fragment was identified by PCR using a primer combination of SEQ ID NO: 80 and SEQ ID NO: 81 was screened out. In the case of genome DNA of wild-type strain, 2300 bp of DNA fragment is obtained by PCR using a primer combination of SEQ ID NO: 80 and SEQ ID NO: 81. The obtained clone was inoculated to YPD medium (20 g/L of Bacto Peptone, 10 g/L of Yeast Extract, and 20 g/L of D-glucose), and cultured by stirring at a temperature of 30° C. for 230 rpm, and then, smeared on a 5-FOA containing a reverse-selective medium (6.7 g/L of Yeast nitrogen base without amino acids (Sigma-Aldrich: Cat. no. Y0626), 1.9 g/L of Yeast synthetic drop-out without uracil (Sigma-Aldrich: Cat. no. Y1501), 0.1 g/L of Uracil, 20 g/L of D-glucose, 1 g/L of 5-fluoroorotic acid (5-FOA), and 20 g/L of Bacto Agar). From among colonies formed from the fourth day after the smearing, a colony in which 4357 bp of DNA fragment was able to be identified by PCR using a primer combination of SEQ ID NO: C3 and SEQ ID NO: C4 was screened out.

(3) Identification of Lactate Production Characteristics of Produced Strain

Each of *S. cerevisiae* strains prepared in (1) and (2) was cultured in a medium and production of lactate was confirmed. Fresh cells obtained from culture plate was inoculated to 5 wt % glucose-containing minimal medium (Minimal Ura drop-out media) [6.7 g/L of Yeast nitrogen base without amino acids (Sigma-Aldrich: Cat. no. Y0626) and 1.9 g/L of Yeast synthetic drop-out without uracil (Sigma-Aldrich: Cat. no. Y1501)] or YPD medium 50 ml in a 500 ml shake-flask such that $OD_{600}$ value was 1, and then, seed-cultured in aerobic conditions while stirring at 240 rpm and at a temperature of 30° C. for 10 hours. Next, the seed culture product was added to a 2 L bioreactor containing 1 L of the same medium such that $OD_{600}$ was 1.0, and cultured at a temperature of 30° C. for 40 hours while stirring at a speed of 350 rpm in microaerobic conditions in which air was provided at flow rate of 100 ml/min.

Acetaldehyde generated in culture was analyzed as follows: vaporized acetaldehyde was captured by using a cold-water trap and analyzed by using GS-MS (Agilent 7890/5973 GC-MS equipped with a 30 m length, 0.25 mm i.d., 0.25 um film thickness, fused silica capillary column (DB-5MS, Agilent)). Cell growth in culture was evaluated as $OD_{600}$ value measured by using a spectrophotometer. Culture supernatant obtained from flask culture and bioreactor was analyzed by high performance liquid chromatography (HPLC). The culture supernatant was filtered by using 0.45 um syringe filter, and then, L-lactate, glucose, acetate, glycerol, and ethanol of which were quantified by using a HPLC device (Waters e2695 Separation Module instrument equipped with a Waters 2414 Differential Refractometer and a Waters 2998 Photodiode Array Detector (Waters, Milford, Mass.)). HPLC column used herein was Aminex HPX-87H Organic Acid Analysis Column (300 mm×7.8 mm; Bio-Rad) which was equilibrated by using 2.5 mM $H_2SO_4$ in water at a flow rate of 0.5 mL/min at a temperature of 60° C.

For control test, wild-type *S. cerevisiae* CEN.PK2-1D, *S. cerevisiae* CEN.PK2-1D (Δadh1::ldh), and *S. cerevisiae* CEN.PK2-1D (Δpdc1::ldh, Δcyb2::ldh, Δgpd1::ldh) were used.

Table 1 shows amounts of lactate and acetaldehyde measured after 10 hours of aerobic culturing or 40 hours of microaerobic culturing the strain prepared in (1) in Minimal Ura drop-out media as seed culture. Cell concentration during measurement was 8.0 $OD_{600}$.

TABLE 1

| Strain | Lactate (g/l) | Acetaldehyde (g/l) |
| --- | --- | --- |
| Control | 42.1. | 3.76. |
| Control (+mhpF) | 48.9. | 2.47. |

In Table 1, Control indicates *S. cerevisiae* CEN.PK2-1D (Δadh1::ldh, Δpdc1::ldh, Δcyb2::ldh, Δgpd1::ldh). Referring to Table 1, *S. cerevisiae* including exogenous mhpF gene showed 16.5% increase in the production of lactate, compared to a strain (control) that did not include exogenous mhpF gene, and 34.3% decrease in the production of acetaldehyde, which is a toxic material. Accordingly, *S. cerevisiae* including exogenous mhpF gene unexpectedly showed a substantial increase in the lactate production compared to the strain (control) that did not include exogenous mhpF gene, so that *S. cerevisiae* including exogenous mhpF gene may be efficiently used in producing lactate.

Table 2 shows an amount of lactate measured after 10 hours of aerobic culturing or 40 hours of microaerobic culturing the strain prepared in (2) in YPD media as seed culture. Cell concentration during measurement was 8.0 $OD_{600}$.

TABLE 2

| Strain | Lactate (g/l) | Lactate yield (%) |
| --- | --- | --- |
| Control | 103. | 82.4. |
| Control (+mhpF) | 106. | 83.9. |
| Control (+mhpF, Δald6) | 113. | 86.0. |
| Control (+mhpF, Δald6, +EutE) | 136. | 90.8. |

In Table 2, Control indicates *S. cerevisiae* CEN.PK2-1D (Δadh1::ldh, Δpdc1::ldh, Δcyb2::ldh, Δgpd1::ldh). Referring to Table 2, *S. cerevisiae* including exogenous mhpF gene, ald6 gene-deleted *S. cerevisiae* including exogenous mhpF gene, and ald6 gene-deleted *S. cerevisiae* including exogenous mhpF gene and EutE gene respectively showed 2.9%, 9.7%, and 32% increase in the production of lactate, compared to the control. Accordingly, S. cerevisiae including exogenous mhpF gene and/or exogenous EutE gene unexpectedly showed a substantial increase in the lactate production compared to the strain (control) that did not include exogenous mhpF gene, so that S. cerevisiae may be efficiently used in producing lactate.

Figure 3:
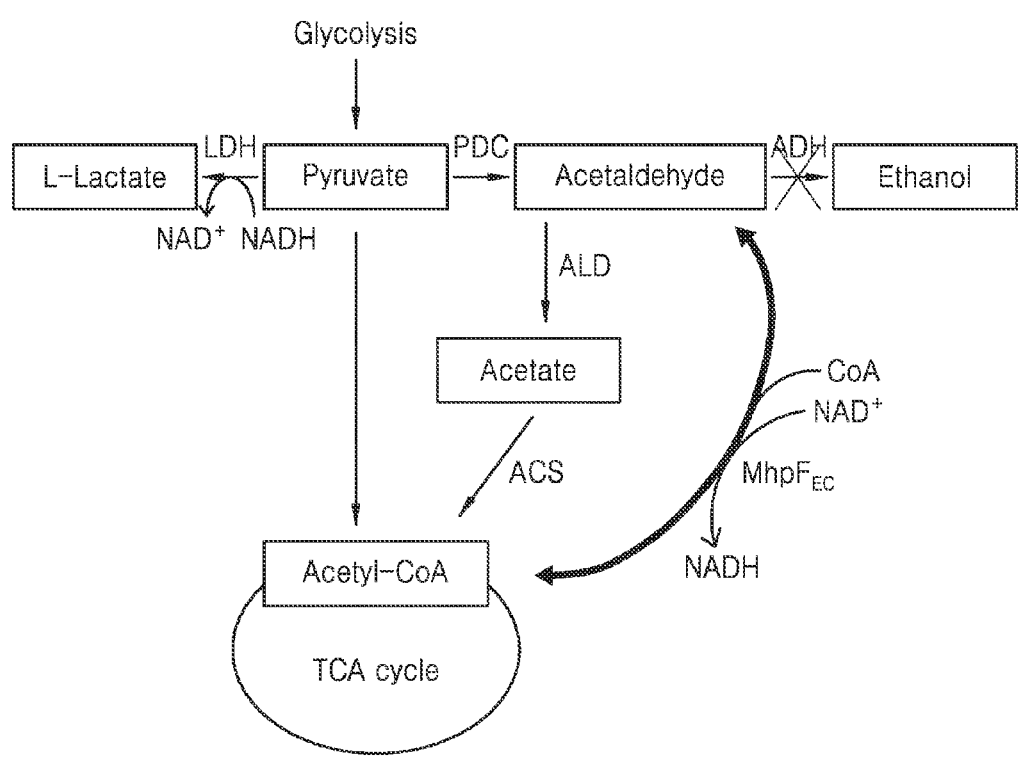
FIG. 3 shows a metabolic pathway associated with conversion of generated pyruvate into lactate.

FIG. 3 shows a metabolic pathway associated with conversion of generated pyruvate into lactate according to an embodiment. In FIG. 3, MhpF$_{EC}$ indicates E. coli (EC)-derived exogenous A-ALD All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A genetically engineered yeast cell comprising, an acylating acetaldehyde dehydrogenase enzyme of class EC 1.2.1.10 that catalyzes conversion of acetaldehyde to acetyl-CoA, and a lactate dehydrogenase enzyme of class 1.1.2.27 or EC 1.1.1.28 that catalyzes conversion of pyruvate to lactate,
wherein the activity of converting acetaldehyde to acetyl-CoA and converting pyruvate to lactate is increased in the genetically engineered yeast cell as compared to a parent cell of the genetically engineered yeast cell, and the genetically engineered yeast cell produces lactate, wherein the yeast cell is of the species *Saccharomyces cerevisiae*.

2. The genetically engineered yeast cell of claim 1, wherein the genetically engineered yeast cell exhibits decreased activity of an alcohol dehydrogenase (ADH) enzyme of class EC 1.1.1.1 that catalyzes conversion of acetaldehyde to ethanol compared to the parent cell.

3. The genetically engineered yeast cell of claim 1, wherein the cell does not include an exogenous enzyme of class EC 4.1.3.39.

4. The genetically engineered yeast cell of claim 1, wherein the enzyme that catalyzes conversion of acetaldehyde to acetyl-CoA has 95% or more sequence identity with SEQ ID NO: 1 or 54.

5. The genetically engineered yeast cell of claim 1, wherein the genetically engineered yeast cell comprises at least one of an exogenous gene that encodes the enzyme that catalyzes conversion of acetaldehyde to acetyl-CoA, or an exogenous gene that encodes the enzyme that catalyzes the conversion of pyruvate to lactate.

6. The genetically engineered yeast cell of claim 1, wherein an exogenous gene that encodes the enzyme that catalyzes conversion of acetaldehyde to acetyl-CoA is a gene encoding an amino acid sequence having 95% or more sequence identity with SEQ ID NO: 1 or 54.

7. The genetically engineered yeast cell of claim 1, wherein the enzyme that catalyzes conversion of pyruvate to lactate has 95% or more sequence identity with SEQ ID NO: 6, 37, 38, or 39.

8. The genetically engineered yeast cell of claim 5, wherein the exogenous gene that encodes the enzyme that catalyzes the conversion of pyruvate to lactate is a gene encoding an amino acid sequence having 95% or more sequence identity with SEQ ID NO: 6 or a gene having 95% or more sequence identity with SEQ ID NO: 7, 40, 41, or 42.

9. The genetically engineered yeast cell of claim 2, wherein a gene of the yeast cell that encodes an enzyme that catalyzes conversion of acetaldehyde into ethanol is disrupted.

10. The genetically engineered yeast cell of claim 1, wherein the genetically engineered yeast cell has decreased activity of an enzyme of class EC 4.1.1.1 that catalyzes conversion of pyruvate into acetaldehyde, an enzyme of class EC 1.1.2.4 or EC 1.1.2.3 that catalyzes conversion of lactate to pyruvate, an enzyme of class EC 1.1.1.8 that catalyzes conversion of dihydroxyacetone phosphate (DHAP) to glycerol-3-phosphate (G3P), an enzyme of class EC 3.1.3.21 that catalyzes conversion of glycerol-3-phosphate (G3P) to glycerol, an enzyme of class EC 1.2.1.4, EC 1.2.1.3, or EC 1.2.1.5 that catalyzes conversion of acetaldehyde to acetate, or combination thereof, as compared to a parent cell of the genetically engineered yeast cell.

11. The genetically engineered yeast cell of claim 10, wherein a gene that encodes the enzyme of class EC 4.1.1.1 that catalyzes conversion of pyruvate to acetaldehyde, a gene that encodes the enzyme of class EC 1.1.2.4 or EC 1.1.2.3 that catalyzes conversion of lactate to pyruvate, a gene that encodes the enzyme of class EC 1.1.1.8 that catalyzes conversion of dihydroxyacetone phosphate (DHAP) to glycerol-3-phosphate (G3P), a gene that encodes the enzyme of class EC 3.1.3.21 that catalyzes conversion of glycerol-3-phosphate to glycerol, a gene that encodes the enzyme of class EC 1.2.1.4, EC 1.2.1.3, or EC 1.2.1.5 that catalyzes conversion of acetaldehyde to acetate, or a combination thereof is disrupted in the genetically engineered yeast cell.

12. A method of producing a genetically engineered yeast cell of claim 1 that produces lactate, the method comprising:

introducing into a yeast cell a gene that encodes an acylating acetaldehyde dehydrogenase enzyme of class EC 1.2.1.10 that catalyzes conversion of acetaldehyde to acetyl-CoA, and a gene that encodes a lactate dehydrogenase enzyme of class 1.1.2.27 or EC 1.1.1.28 that catalyzes conversion of pyruvate to lactate; and disrupting in the yeast cell a gene that encodes an alcohol dehydrogenase (ADH) enzyme of class EC 1.1.1.1 that catalyzes conversion of acetaldehyde to ethanol.

13. The method of claim 12, further comprising disrupting in the yeast cell a gene that encodes an enzyme of class EC 4.1.1.1 that catalyzes conversion of pyruvate to acetaldehyde, a gene that encodes an enzyme of class EC 1.1.2.4 or EC 1.1.2.3 that catalyzes conversion of lactate to pyruvate, a gene that encodes an enzyme of class EC 1.1.1.8 that catalyzes conversion of dihydroxyacetone phosphate (DHAP) to glycerol-3-phosphate, a gene that encodes an enzyme of class EC 3.1.3.21 that catalyzes conversion of glycerol-3-phosphate to glycerol (G3P), a gene that encodes an enzyme of class EC 1.2.1.4, EC 1.2.1.3, or EC 1.2.1.5 that catalyzes conversion from acetaldehyde to acetate, or a combination thereof.

14. The genetically engineered yeast cell of claim 1, wherein the enzyme that catalyzes conversion of acetaldehyde to acetyl-CoA has 95% or more sequence identity with SEQ ID NO: 82.

15. The genetically engineered yeast cell of claim 1, wherein an exogenous gene that encodes the enzyme that catalyzes conversion of acetaldehyde to acetyl-CoA is a gene having 95% or more sequence identity with SEQ ID NO: 2, SEQ ID NO: 3, or SEQ ID NO: 53.

16. A method of producing lactate comprising culturing the genetically engineered yeast cell of claim 1 to produce lactate; and recovering the lactate from a culture product.

17. The method of claim 16, wherein the culturing is performed under microaerobic conditions.

\* \* \* \* \*